US005696696A

United States Patent [19]
Gunther et al.

[11] Patent Number: 5,696,696
[45] Date of Patent: Dec. 9, 1997

[54] APPARATUS AND METHOD FOR AUTOMATICALLY ACHIEVING AND MAINTAINING CONGRUENT CONTROL IN AN INDUSTRIAL BOILER

[75] Inventors: John C. Gunther, Bensalem, Pa.; Scott M. Boyette, Wilmington, Del.; Eric A. Thungstrom, Wyndmoor, Pa.; Norman B. Worrell, Feasterville, Pa.; Paul R. Burgmayer, Wayne, Pa.

[73] Assignee: BetzDearborn, Inc., Trevose, Pa.

[21] Appl. No.: 321,338

[22] Filed: Oct. 11, 1994

[51] Int. Cl.$^6$ .................................................. G01N 27/00
[52] U.S. Cl. .................... 364/500; 364/496; 364/499; 364/510; 395/907; 395/915
[58] Field of Search .................................. 364/496, 497, 364/499, 500, 502, 149, 150, 153, 164, 165, 148, 166, 509, 510, 578, 492, 468.1, 157, 132, 159, 478.08, 152, 151; 210/743, 742, 739, 96.1, 103, 69.6, 311–313.85; 422/62, 12, 14, 16, 110, 111, 81; 122/45 R, 451, 451.1, 2, 401; 395/906, 907, 914, 915; 436/55, 56, 50; 376/216, 217; 237/8 A

[56] References Cited

U.S. PATENT DOCUMENTS

| | | | |
|---|---|---|---|
| 2,842,311 | 7/1958 | Petrie | 364/150 |
| 3,011,709 | 12/1961 | Jacoby | 364/150 |
| 3,462,364 | 8/1969 | Carlson | 210/709 |
| 3,792,244 | 2/1974 | Wilke | 364/499 |
| 3,804,253 | 4/1974 | Wellman et al. | 210/85 |
| 3,891,836 | 6/1975 | Lee | 364/132 |
| 4,016,079 | 4/1977 | Severin | 210/96.1 |
| 4,033,871 | 7/1977 | Wall | 210/96.1 |
| 4,053,743 | 10/1977 | Niemi | 364/500 |
| 4,181,951 | 1/1980 | Boeke | 364/499 |
| 4,236,220 | 11/1980 | Kogami et al. | 376/217 |
| 4,239,493 | 12/1980 | Niemi et al. | 436/55 |
| 4,349,869 | 9/1982 | Prett et al. | 364/159 |
| 4,644,479 | 2/1987 | Heaper et al. | 364/492 |
| 4,659,459 | 4/1987 | O'Leary et al. | 210/87 |
| 4,736,316 | 4/1988 | Wallman | 364/149 |
| 4,770,843 | 9/1988 | Taleyarkham | 376/216 |

(List continued on next page.)

OTHER PUBLICATIONS

Brestel, L. O. Power Oct. 1987 61–65.
Rogers, et al. Corrosion 92 1992 Paper No. 413 (1–10).
Economy, et al. Sodium Phosphate Solutions at Boiler Condition: Solubility, Phase Equilibira, and interactions with Magnetite pp. 162–173.
Abstract—A Practical Approach to Real Time Data Acquisition and Automated Chemical Feed at a Fossil Fueled Cycling Duty Station.

*Primary Examiner*—Emanuel T. Voeltz
*Assistant Examiner*—Hal D. Wachsman
*Attorney, Agent, or Firm*—Caesar, Rivise, Bernstein, Cohen & Pokotilow, Ltd.

[57] ABSTRACT

A control system for automatically achieving and maintaining a desired sodium/phosphate ratio and phosphate concentration of the boiler water in an industrial boiler for minimizing corrosion. The system uses an adaptive controller that models the boiler which enables the system to predict boiler pH and phosphate concentrations at any future time given the feed rates, feed concentrations of high and low sodium/phosphate stocks, blowdown rate, mass of the boiler water, initial boiler phosphate concentration and initial pH. Once these future concentrations are determined, the controller then determines which feed rates will return the current boiler water state to, and then maintain the boiler water at, the desired sodium/phosphate congruency ratio in the least amount of time. Where the controller determines that it is not possible to move the current boiler water state to the desired congruency setpoint, the controller determines a feed rate program that will move the current boiler water state to the attainable steady state point closest to the desired setpoint. An alternative embodiment fixes the phosphate concentration by ratioing the phosphate feed with the blowdown rate while continuously monitoring blowdown pH. This arrangement allows for the control of sodium by switching between the high and low ratio sodium/phosphate stocks based on the measured pH with respect to the pH setpoint.

74 Claims, 22 Drawing Sheets

U.S. PATENT DOCUMENTS

| | | | |
|---|---|---|---|
| 4,833,622 | 5/1989 | Bart et al. | 364/496 |
| 4,897,797 | 1/1990 | Free, Jr. et al. | 364/500 |
| 5,038,270 | 8/1991 | Tozawa et al. | 364/148 |
| 5,040,725 | 8/1991 | Butler | 237/8 A |
| 5,057,229 | 10/1991 | Schuelenburg | 210/743 |
| 5,083,281 | 1/1992 | Rabindran et al. | 364/478.08 |
| 5,132,916 | 7/1992 | Gulaian et al. | 364/502 |
| 5,141,716 | 8/1992 | Muccitelli et al. | 422/16 |
| 5,152,252 | 10/1992 | Bolton et al. | 122/401 |
| 5,164,159 | 11/1992 | Hayashi et al. | 422/81 |
| 5,218,526 | 6/1993 | Mozzo | 364/152 |
| 5,248,577 | 9/1993 | Jerome | 430/30 |
| 5,262,963 | 11/1993 | Stana et al. | 364/500 |
| 5,288,713 | 2/1994 | Reese | 210/696 |
| 5,320,967 | 6/1994 | Avallone et al. | 436/50 |
| 5,347,446 | 9/1994 | Iino et al. | 364/149 |
| 5,424,942 | 6/1995 | Dong et al. | 364/164 |
| 5,455,763 | 10/1995 | Feingold | 364/149 |
| 5,486,995 | 1/1996 | Kmit et al. | 364/149 |
| 5,516,423 | 5/1996 | Conoby et al. | 210/85 |
| 5,519,605 | 5/1996 | Cawfield | 364/151 |
| 5,521,814 | 5/1996 | Teran et al. | 364/468.1 |
| 5,568,377 | 10/1996 | Seem et al. | 364/157 |
| 5,587,897 | 12/1996 | Iida | 364/148 |

| FIG.15A | FIG. 15B |

| FIG.18A | FIG.18B |
|---|---|
| | FIG.18C |

APPARATUS AND METHOD FOR AUTOMATICALLY ACHIEVING AND MAINTAINING CONGRUENT CONTROL IN AN INDUSTRIAL BOILER

SPECIFICATION

1. Field of the Invention

The invention pertains to automatic control systems for continuously stirred tank reactors (CSTRs). In particular, the invention pertains to automatic control systems for achieving and maintaining optimum congruency and phosphate concentration required to minimize corrosion in industrial high pressure boilers.

2. Background of Invention

Industrial boilers heat up highly purified feedwater to generate steam for power generation, heating, etc.

A natural consequence of steam production is the "cycling up" in concentration of chemicals which enter the boiler inadvertently (e.g., acid leaks) or intentionally (e.g., corrosion inhibitors). A small portion of the boiler water is "blown down" (i.e., removal of concentrated boiler water from the boiler) to keep the concentrations of non-volatile chemicals (i.e., chemicals that do not flow out with the steam but rather remain substantially in the boiler water) at acceptable levels. The rate of blowdown is defined by the "cycles of concentration." The term "cycles of concentration" is defined as the sum of the steam and blowdown flowrates divided by the blowdown flowrate. Cycles in high pressure boilers range from less than 10 to 100 or more. Thus a chemical added at a low concentration (e.g., 0.5 ppm) in the feedwater can cycle up to fairly high boiler concentrations (e.g., 30 ppm).

These boilers are susceptible to, among other things, corrosion. To minimize corrosion, one basic type of corrosion control program that is practiced in the United States within these boilers is phosphate control programs. Typically, in phosphate control programs, a sodium phosphate salt is fed into the solution in order to buffer the solution and to maintain that pH with sodium. The objective of these phosphate control programs is to maintain the measured variables, phosphate and pH, within certain stated guidelines, which are dependent upon boiler pressure by controlling the sodium, phosphate and resultant pH within the boiler water. See "Sodium phosphate Solutions at Boiler Conditions: Solubility, phase Equilibria, and Interactions with Magnetite," by G. Economy, A. J. Panson, Chia-tsun Liu, J. N. Esposito, and W. T. Lindsay, Jr., *Proc. Intl. Water Conf.*, 1975, pp. 161–173.

If the concentration of sodium within the boiler water (which is given by the pH, i.e., pH is proportional to effective sodium) is divided by the concentration of phosphate within the boiler water, there exists a range of optimum sodium-to-phosphate (Na/PO$_4$) ratios that, if achieved and maintained within the boiler water, will minimize corrosion. Where the boiler water is operated and maintained at a Na/PO$_4$ ratio that is below 3.0:1, the boiler is said to be operating with coordinated phosphate/pH control (also known as "captive alkalinity"). Where the boiler water is operated and maintained at a Na/PO$_4$ ratio that is between 2.2:1 and 2.8:1, the boiler is said to be operating with congruent control. Where the boiler is water is operated at a Na/PO$_4$ ratio that is above 3.0, a boiler is said to be operating with "equilibrium phosphate control." All three types of control can be attained and maintained with the instant invention.

With any of these corrosion control programs, the boiler uses phosphate as the major buffering agent. Additionally, sodium and phosphate concentrations are interdependent variables that must either be controlled simultaneously, or one subservient to the other. They cannot be controlled independently.

Furthermore, boiler systems are extremely slow systems because they comprise large volumes. As an example, a 280,000 pound water boiler having a blowdown rate of 3000 pounds/hour takes over three days to remove and replenish the boiler water. Many things can happen during that time that can alter the operator's initial guess at what concentrations should be added to manually correct control problems.

The applicants have found that conventional control schemes like Proportional Integral Derivative (PID) control are insufficient to provide practical, universally applicable automatic control of this boiler chemistry for a number of reasons. First, setpoint overshoot is a problem when attempting to control pH in a large volume system. Limitations in pumping capacity inherent in a real-life pumping scheme make "integral windup" a serious problem. Integral windup causes a control system to overshoot its setpoint. Overshoot is also a problem in controlling pH with PID control due to the asymmetric nature of pH control. Although this problem could potentially be avoided using blowdown flow controllers, these devices are expensive and difficult to maintain and calibrate.

Second, tuning such a PID loop is very difficult. Although tuning can be done in many ways, the methods generally require one of two sets of conditions be maintained, either of which are difficult to achieve in an operating boiler. In one general tuning method, the boiler chemistry must be held constant for multiples of the first order time constant defined by the volume of the boiler divided by its blowdown flow rate. In real-life applications, such a steady-state cannot be established for that length of time due to small perturbations in feedwater contaminants concentrations. In the other general tuning method, the boiler chemistry must be driven out of the region normally considered to be non-corrosive to derive the tuning constants. This negates the beneficial effect of the treatment. Since any change in blowdown flow rate (a normal part of boiler operations) will render the measured tuning constant invalid, tuning must be repeated for each blowdown flow setting.

There is one reference to sodium/phosphate control in the literature which demonstrates the difficulties of this method and its shortcomings. In "A Practical Approach to Real Time Data Acquisition and Automated Chemical Feed at a Fossil Fueled Cycling Duty Station", by C. E. Frederick presented at the International Conference on Cycle Chemistry in Fossil Plants, Jun. 4–6, 1991, the boiler system was tuned using a semi-empirical method to a specific boiler, rather than being adaptable to various types and sizes of industrial boilers. Furthermore, the system disclosed in that reference requires the use of phosphate analyzers which are expensive and require frequent re-calibrations and maintenance.

The closest art to automatically controlling the Na/PO$_4$ ratio in the water of an industrial boiler is in automated pH control systems. The control of pH is in itself a difficult task, as discussed in U.S. Pat. No. 5,132,916 (Gulaian et al.).

The following U.S. Patents disclose examples of automated pH control systems: U.S. Pat. Nos. 4,053,743 (Niemi), 4,239,493 (Niemi et al.), 4,181,951 (Boeke), 5,132,916 (Gulaian), 5,262,963 (Stana), 4,016,079 (Severin), 5,248,577 (Jerome), 4,033,871 (Wall) and 5,057,229 (Schulenberg).

The Niemi patent discloses an automatic system for controlling the pH and other concentration variables in a chemical reactor. However, use of that system would not be adaptable to an industrial boiler for the following reasons. The system utilizes a method that requires a steady state that is reached rapidly, which, as discussed previously, an industrial boiler does not exhibit. Consequently, the Niemi patent teaches controlling pH by use of a PID controller, which, as discussed previously, would be difficult to use in Corrosion Control Phosphate (CCP) programs described above.

The Niemi et al. patent discloses an automatic system for controlling the pH in a continuous flow vessel. However, this system is also not adaptable to industrial boilers for the following reasons. For boiler systems, the known tuning methods do not apply for the reasons described above. If the residence time distribution is known, then simulation of tuning methods requires a perfect match of a simulator and reality. The assumptions of linear processes of first order reactions is not applicable. Therefore, the method listed in Niemi et al. will only work for systems with small perturbations. Industrial boilers exhibit larger deviations. Furthermore, Niemi et al. identifies proportional, proportional-integral and proportional-integral-derivative controls along with an adjustable gain controller. Limitations on feed concentrations versus system volume will make any adjustable gain ineffective when bounded by limitations in a "pumpable region." Finally, the same pumpable limitations will make integral windup a serious problem in a large volume system.

The Boeke patent discloses an automatic control system for the adjustment of pH that is described using the term "on-off". However, this is not an ON/OFF controller. The series of solenoids that actuate flow across different size orifices produce a signal proportional to feedback. The series of solenoids provides proportional response that is discreet within a specific flow window. This is analogous to a stepwise integration of a continuous function.

The Gulaian patent discloses an automatic system for controlling pH and utilizing an estimation for a pH titration curve in the adaptive control of pH. However, this system is also relegated to short residence times and the use of proportional-integral control. Furthermore, the patent does not discuss limitations from integral windup.

The Stana patent discloses an automatic system for controlling a phosphoric acid plant. However, this system does not involve a model of the system but rather teaches a target feed where the system is compensated for its chemical deficit and then placed in steady state. The algorithm utilized by the system contains predetermined constants that are unique to a particular phosphoric acid plant, and are therefore, not readily adaptable to a variety of phosphoric acid plants (e.g., different plant volumes would require that new constants be calculated and inserted into the algorithm). Moreover, this system controls only sulfuric acid feed and does not try to control two interdependent variables.

The Severin patent discloses an automatic chlorine and pH control apparatus for swimming pools. The apparatus controls two variables, i.e., chlorine and pH, under the assumption that the two are not interrelated. Although chlorine affects pH, chlorine has a minor effect on pH and can be isolated and controlled separately. This is because in a swimming pool, chlorine is not the only buffering agent. Its contribution to the pH is masked by the high concentration of anions from the makeup water and atmosphere. This allows the pH to be controlled independent of the chlorine concentration. In contrast, as discussed earlier, a congruent controlled boiler uses phosphate as the major buffering agent, and the pH and phosphate are interdependent variables that must either be controlled simultaneously, or one subservient to the other. They cannot be controlled independently. In addition, the Severin apparatus also ignores the cycle time of a swimming pool and assumes that the control is constant through the system. It does not account for lag and residence time effects and probably cycles up and down drastically when in operation. Finally, the pH control range is anticipated as narrow, and works on the assumption that pH is linear in the chosen range.

The Wall patent discloses a system for continuously monitoring and controlling the pH and free halogen in swimming pool water. Although this patent mentions the concept of two-sided control (i.e., monitoring whether pH or halogen or both fall within or without predetermined ranges), the control of the pH of swimming pools and the control of pH in a boiler are not interchangeable, as described above.

The Schulenberg patent discloses an automatic system treatment of cooling circuit water. Although this system describes on/off pH control of a single component to provide one sided control and the system adds other components according to vaporous loss, the chemistry is different from that of a boiler. The chlorine in the Schulenberg patent is not the major buffer, and no attempt is made to maintain the $CO_2$ alkalinity. In addition, this system cannot control two interdependent variables. The corrosion inhibitor and the pH are not interdependent as are the phosphate (similar to a corrosion inhibitor) and pH.

The Jerome patent discloses a reactant concentration control method and apparatus for precipitation reactions. The system does base feed one reagent and adjusts the second. However, the method and apparatus assume that the system is near steady state at all times. The calculations are linearized and performed incrementally to make the calculations simpler. The model used in the method/apparatus is not a true continuously stirred tank reactor (as is the model for industrial boilers).

U.S. Pat. No. 5,141,716 (Muccitelli), which is owned by the same Assignee of the present patent application discloses a method of reducing corrosion in a boiler using coordinated phosphate control. However, this method calls for the administering of particular hydroxyethyl piperazines in specific ratios with phosphate, i.e., there is no automatic apparatus nor methods disclosed of conducting this feed.

Two other references which discuss coordinated phosphate control are: *Justification and Engineering Design for the On-Line Monitoring and Automation of a Congruent phosphate/pH Program*, by Michael E. Rogers, Ian Verhappen and Stephen Porter, Paper No. 413, The NACE Annual Conference and Corrosion Show 1992; *Expert System Helps Fine-Tune Boiler-Water Chemistry*, by Leyon O. Bretsel and Lon C. Brouse, Power Magazine 1987. In the former reference, although a proposal is discussed for controlling phosphate feed to the feedwater while controlling conductivity in the boiler water, there is no disclosure of any automatic simultaneous control of phosphate and congruency ($Na/PO_4$ ratio). With regard to the latter reference, although there is a discussion of providing the operator with chemical feed adjustments, there is no real-time, automatic control system that is disclosed for controlling the order to control congruency.

Therefore the prior art does not disclose an effective method for controlling two interdependent and non-volatile chemicals, e.g., sodium and phosphate, in a system that is rarely at steady state that is auto-tuning and does not require control of the blowdown flow. None of the above cited art have devised an apparatus nor a method for achieving an automatic coordinated sodium/phosphate control system for a variety of industrial boilers without the need for on-line phosphate analyzers.

OBJECTS OF THE INVENTION

Accordingly, it is the general object of this invention to provide an automatic system for coordinated, equilibrium and congruent sodium/phosphate control of an industrial boiler which improves upon and overcomes the disadvantages of the prior art.

It is another object of this invention to provide an automatic system for sodium/phosphate control that requires no tuning procedure.

It is still another object of the preferred embodiment of this invention to provide an automatic system for sodium/phosphate control that can be implemented universally, that is easily adapted to any particular boiler system.

It is still yet a further object of this invention to provide an automatic system for sodium/phosphate control where feed pumps are the only means available for control and, in particular, where blowdown controllers tied to the automatic system are not available.

It is yet another object of this invention to function as an advisory system, instructing the operator what to do, or to directly control congruency.

It is still yet another object of this invention to control any number of chemicals used in controlling congruency, e.g., polymer or chelant feeds as well as sodium and phosphate.

It is still yet a further object of this invention to control chemical concentrations when precipitation or volatilization is occurring.

It is still even a further object of this invention to control more than one boiler system simultaneously.

It is another object of this invention to provide an efficient method to achieve the congruency control (target) region while minimizing the time spent outside of this control region.

It is another objective of this invention to, once within the target region, provide an efficient method to achieve the congruent control ratio and phosphate setpoints and to remain within the target region.

It is still another object of this invention to provide an information database of the congruency control system for use in diagnostics.

It is yet a further object of this invention to provide an alternative means of determining blowdown without having to utilize expensive blowdown measurement equipment.

It is still yet a further object of this invention to provide an alternative means of determining the contribution to boiler water pH from ionic feedwater contaminant ingresses without having to use chemical analyzers and feedwater flow meters.

It is still a further object of this invention to provide a controller having a well-defined response for those situations where controllers using conventional general purpose equation solvers would simply conclude that there is no possible response.

It is further object of this invention to provide a chemical feed system which minimizes dead time while maximizing controllability.

It is yet another object of a second embodiment of this invention to provide an automatic congruent control system that utilizes a pumping scheme which fixes the phosphate concentration in the boiler water while permitting the sodium/phosphate ratio to be controlled.

SUMMARY OF THE INVENTION

These and other objects of the instant invention are achieved by providing an automatic control system for controlling at least two interdependent chemicals in the fluid of a continuously stirred tank reactor system having an effluent flow. The control system comprises input means for receipt of fluid parameters and control means responsive to the input means. The control means uses non-proportional control for automatically achieving and maintaining a setpoint of the at least two interdependent chemicals in the fluid without controlling the effluent flow.

In addition, a second embodiment is provided for controlling the sodium-to-phosphate ratio and the phosphate concentration of a boiler fluid in an industrial boiler having a blowdown flow. The system comprises input means for receipt of a boiler fluid parameter and a parameter indicative of the phosphate concentration. The system further comprises control means responsive to the input means for automatically achieving and maintaining a predetermined fixed phosphate concentration of the boiler fluid and for automatically achieving and maintaining a predetermined desired sodium-to-phosphate ratio of the boiler fluid without controlling the blowdown flow.

DESCRIPTION OF THE DRAWINGS

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Unless otherwise specified, all references to sodium or sodium-to-phosphate ratio (Na/PO$_4$) refer to that sodium which interacts with the phosphate to maintain the boiler water so as to inhibit corrosion. This is also referred to as "effective sodium" or the "effective sodium-to-phosphate ratio."

Figure 1:
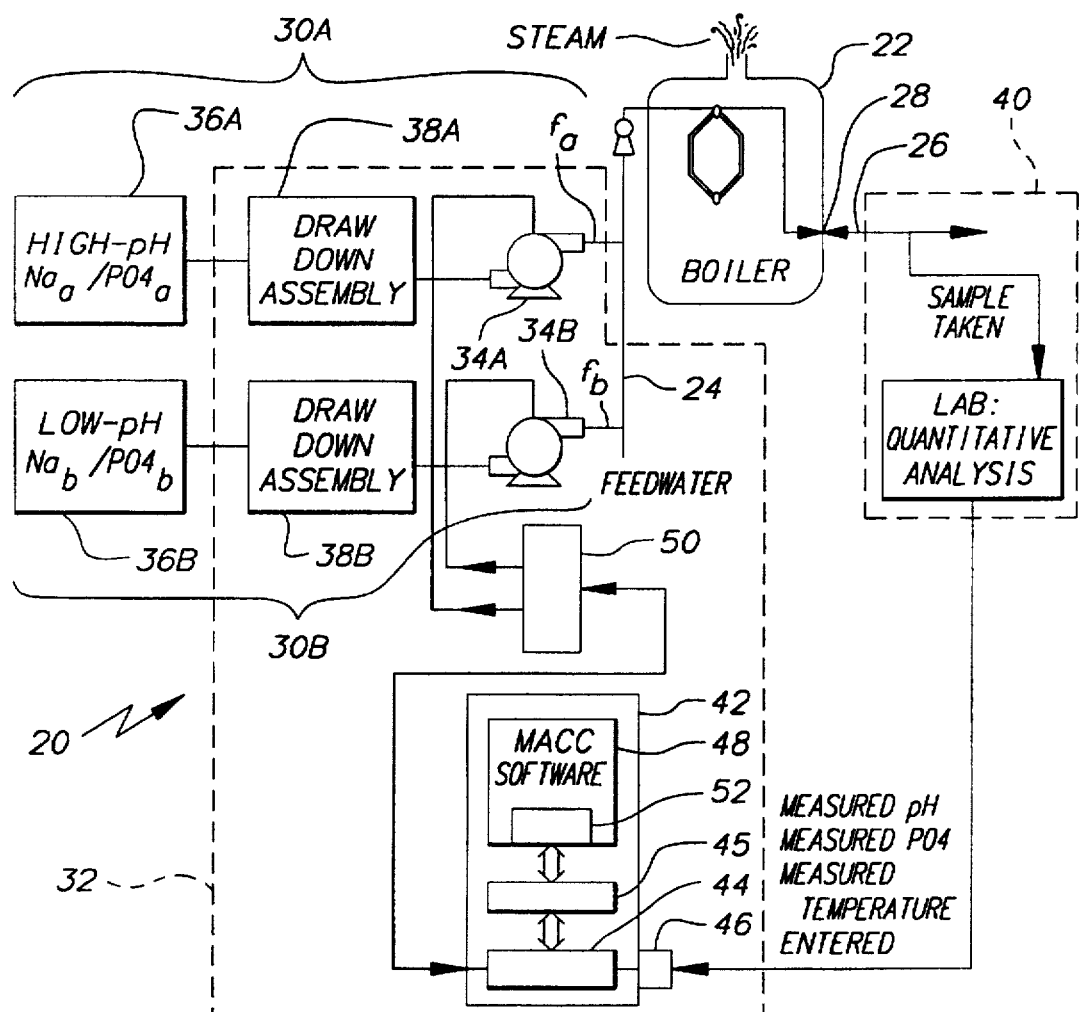
FIG. 1 is a block diagram of the Model Adaptive Corrosion Control (MACC) system.

Referring now in detail to the various figures of the drawing wherein like reference characters refer to like parts, there is shown at 20 in FIG. 1, the preferred embodiment of the model adaptive congruent controller system 20 of the present invention (hereinafter known as the MACC system). Generally, the MACC system 20 uses a model of an industrial boiler to predict the feed rates of particular mixtures of two chemicals, e.g., sodium and phosphate, to achieve and maintain an acceptable range of sodium-to-phosphate congruencies and phosphate concentrations where these congruencies are defined by the sodium-to-phosphate ratio being between high and low limits defined by the boiler operating conditions, and then checks itself against its prediction and adapts its model to improve its control. The check is provided for by a laboratory pH and PO$_4$ analysis, rather than with the use of any on-line pH analyzers or PO$_4$ analyzers. Hereinafter, the targeted range of congruency and phosphate is referred to as the target region and the specific congruency and phosphate desired is referred to as the setpoint, as will be discussed in detail later.

The MACC system 20 is arranged to control water treatment chemicals to be introduced into an industrial boiler 22 by way of the feedwater 24 to the boiler 22. The boiler 22 has an effluent flow (hereinafter known as blowdown flow 26) and a blowdown valve 28. The MACC system 20 does not control the blowdown flow 26 via the blowdown valve 28. In fact, one of the distinguishing features of the MACC system 20 over conventional boiler fluid control systems is that the blowdown flow 26 varies independently of the MACC system 20.

The MACC system 20 basically comprises a first chemical feedstream 30A, a second feedstream 30B, a control means 32 and an input means 34. The first chemical feedstream 30A and the second chemical feedstream 30B are each connected to the feedwater line 24. The first chemical feedstream 30A is arranged to deliver a first fluid treatment material or chemical, e.g., sodium phosphate mixture having a particular sodium-to-phosphate ratio, to the water in the boiler 22. Similarly, the second chemical feedstream 30B is arranged to deliver a second fluid treatment material or chemical, e.g., a sodium phosphate mixture having another particular sodium-to-phosphate ratio, to the water in the boiler 22. It is important to note at this juncture that the sodium-to-phosphate ratio in the first chemical feedstream 30A must be different from the sodium-to-phosphate ratio in the second chemical feedstream 30B. The particular sodium-to-phosphate ratio (Na/PO$_4$) determines a particular pH (high or low) for that fluid treatment material.

Sodium and phosphate are non-volatile chemicals in that they do not flow out with the steam but rather only leave the boiler water through the blowdown flow. Furthermore, these chemicals are interdependent in that they both must be controlled in order to achieve and maintain the desired sodium-to-phosphate ratio in the boiler water.

Each feedstream 30A and 30B includes electrically driven pumps 34A and 34B which are coupled to the outlet of respective chemical feed tanks 36A and 36B, via respective draw down assemblies 38A and 38B. The chemical feed tanks 36A and 36B contain high-pH and low-pH sodium phosphate fluid treatment materials, respectively. The draw down assemblies 38A and 38B act as accumulators for enabling precise control of the pumps 34A and 34B by the control means 32.

The control means 32 is arranged to precisely control the two chemical feedstreams 30A and 30B by controlling the operation of the pumps 34A and 34B in order to achieve and maintain a predetermined desired sodium-to-phosphate ratio in the boiler water.

The control means 32 basically comprises a computer-based control unit 42 such as that provided by Betz Laboratories, Inc. under the mark SMARTSCAN Plus and associated software/firmware 44 and a monitor/keyboard 46. The MACC system software 48 for effecting the operation of the control means 32 is set forth in Appendix A, along with an interface portion 45; the interface portion 45 interfaces the SMARTSCAN Plus software/firmware 44 with the MACC system software 48. The control means 32 also includes a feed pump controller 50 and the associated draw down assemblies 38A and 38B.

The feed pump controller 50 and the associated draw down assemblies 38A and 38B are constructed in accordance with the teachings of U.S. Pat. No. 4,897,797, assigned to the same assignee as this invention, namely Betz Laboratories, Inc., and whose disclosure is incorporated by reference herein.

As will be discussed in detail below, the feed pump controller 50 receives the optimum feed rates for both pumps 34A and 34B from the MACC software 48 via the computer 42.

The input means 40 basically comprises a lab analysis of a sample from the blowdown flow 26. The lab analysis provides, among other boiler water parameters, measured pH and measured PO$_4$ values which are then manually entered into the MACC software 48 via the computer 42.

Figure 2:
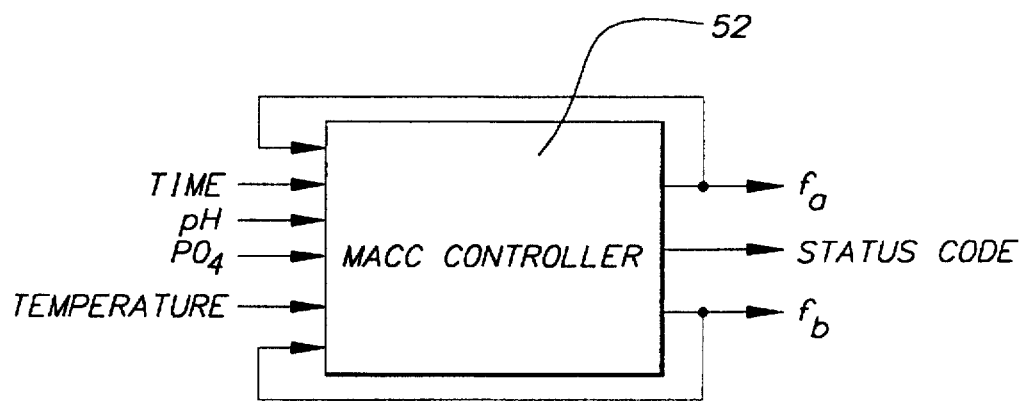
FIG. 2 is a block diagram of the input/output of the MACC controller.

The controller 52 of the MACC system 20 resides in the MACC software 48. As shown in FIG. 2, the controller 52 takes the external inputs of time, pH, PO$_4$ concentration and temperature, which are all measured using samples taken from the boiler blowdown line 26. The MACC system 20 is designed to perform well using only the once a day or once a shift sampling rates typical of manual congruent control. The operator makes these measurements on a blowdown sample, and then enters the results into the controller 52. By contrast, conventional control algorithms, such as PID, would require the much shorter sampling intervals typically associated with on-line pH and phosphate measurements. The controller 52 then utilizing the model equations, discussed below, provides the external outputs of the feed rate ($f_a$) of chemical pump 34A and the feed rate ($f_b$) Of chemical pump 34B to the feed pump controller 50 for precisely controlling pumps 34A and 34B at their respective feed rates. These controller 52-determined-feed rates are also fed back as input to the controller 52, for calculating future feed rates. A third external output, a status code (e.g., for setting alarms, error reporting, etc.) is included in the MACC software 48.

As mentioned earlier, the controller 52 contains model equations that enable the MACC system 20 to predict boiler pH and phosphate concentration at any future time, t, given the feed rates, feed concentrations, blowdown flow rate, mass of the boiler water, initial boiler phosphate concentration and initial pH.

The MACC controller 52 uses these equations, as will be discussed in more detail below, by first running the model equations backward for parameter estimation (i.e., to update the boiler model) and then running the equations forward to determine the optimal feed program.

Since future concentrations of Na and $PO_4$ depend upon blowdown rate, the model equations are used along with the previous and current phosphate samples, elapsed time between samples, and feed rates over the period to back-calculate the blowdown rate, B, required to account for the change in boiler phosphate concentration observed. This eliminates the need for a direct blowdown flow measurement apparatus which is typically a costly device. Similarly, the last two pH samples, elapsed time between samples, feed rates and the estimated blowdown rate (B) are used, in conjunction with the model, to back-calculate a "feedwater contaminant ingress (FCI)", L, into the boiler. This FCI represents a generic acid/base flow into the boiler that accounts for the difference between the pH that should be in the boiler, according to the model, and the measured pH. This flow represents the sum of sodium ions, and other positively charged ions, and negatively charged ions in the feedwater 24 (FIG. 1). Thus, it is possible that the sum of these ions can have a positive or negative sign associated with it. Again, this eliminates the need for a chemical analyzer and flow meter in the boiler feedwater stream.

Once the blowdown rate, B, and the feedwater contaminant ingress, L, are estimated, the model equations are run forward. In principle, all possible feed programs can be plugged into the model and the future boiler sodium/phosphate ratio and phosphate concentration predicted by the model compared with their control ranges and setpoints. As described below, more efficient and robust methods of determining this optimal feed program are employed. The optimal feed program, which will remain in effect until the next operator sample is entered, is the one that most rapidly brings the boiler $Na/PO_4$ ratio and phosphate concentration into their control limits (i.e., the target region, as will be discussed later), and once within the control limits, to the setpoint.

If a situation arose such that the chemical feed pumps 34A and 34B did not have the required pumping capacity to counteract an unusually large FCI, it would be impossible to bring the system into the control range. In that situation, the operator would be informed of the problem and the MACC controller 52 would deliver as much treatment as it could to counteract the FCI. In general, whenever a situation arises where the MACC controller 52 determines that the target region 60 (or setpoint 58, as will be described later) cannot be reached, the MACC controller 52 sets the feed rates, $f_a$ and $f_b$, so that the distance between the model predicted steady-state boiler Na and $PO_4$ concentrations and the target region 60 (or setpoint 58) is minimized.

Figure 3:
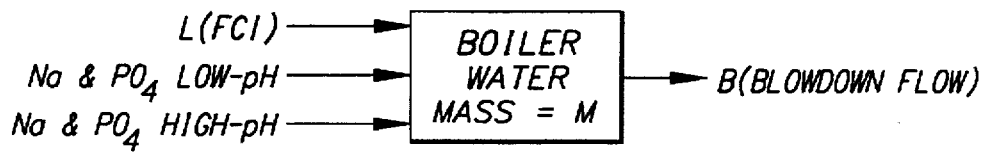
FIG. 3 is a diagram showing the boiler water influents/effluents used by the MACC controller boiler model.

The model equations are based on the fact that the MACC controller 52 assumes that only sodium and phosphate are present in the boiler 22 (FIG. 3). Since both sodium and phosphate are non-volatile, the boiler steaming rate does not impact upon sodium or phosphate mass balance around the boiler 22, and thus does not appear in FIG. 3. The FCI, L, is idealized as a constant moles/hr flow rate into the boiler 22. The mass, M, of the boiler is assumed constant. Furthermore, hereinafter use of the term "PO4" refers to total phosphate concentration, i.e., the sum of [$H_3 PO_4$] phosphoric acid, and the charged forms of $PO_4$: [$H_2PO_4^-$] monobasic phosphate, [$HPO_4^=$] dibasic phosphate and [$PO_4^{\equiv}$] tribasic phosphate.

To that end and based on the assumption that the boiler water concentrations are uniform (good mixing), the first model equation is given as:

$$M*d(PO4)/dt = f_a*PO4_a + f_b*PO4_b - PO4*B \qquad \text{(Equation \#1)}$$

where,

PO4=boiler (hence blowdown) phosphate concentration, moles/kg;

$f_a$=feed rate (kg/hr) for chemical pump 34A;

$f_b$=feed rate (kg/hr) for chemical pump 34B;

$PO4_a$=feed concentration (moles/kg) for phosphate from tank 36A;

$PO4_b$=feed concentration (moles/kg) for phosphate from tank 36B;

blowdown rate, in kgs/hr, B; and mass of boiler, in kgs, M.

Equation #1 states that the rate of change of the total phosphate in the boiler 22 equals the net flow rate of phosphate into/out of the boiler 22.

Solution of this first order differential equation under the assumption that M, $f_a$, $PO4_a$, $f_b$, $PO4_b$ and B remain fixed, yields the following chemical concentration functions:

$$PO_4(t) = ((f_a*PO4_a + f_b*PO4_b)/B)*(1-e^{(-t/\tau)}) + PO4(0)*e^{(-t/\tau)} \qquad \text{(Equation \#2)}$$

$$Na(t) = ((f_a*Na_a + f_b*Na_b + L)/B)*(1-e^{(-t/\tau)}) + Na(0)*e^{(-t/\tau)} \qquad \text{(Equation \#3)}$$

where $\tau$=first order time constant=M/B;

$Na_a$=feed concentration (moles/kg) for sodium from tank 36A;

$Na_b$=feed concentration (moles/kg) for sodium from tank 36B;

L=FCI (moles/hr) into boiler 22;

PO4(0)=initial phosphate concentration (moles/kg); and

Na(0)=initial sodium concentration.

Equation #3 follows by analogy with Equation #2 since the sodium and phosphate flows into/out of the boiler 22 are exactly analogous, except for the addition of the FCI, L, (also assumed constant) into the boiler 22.

It is apparent that unlike phosphate, which is directly measured by the operator, the sodium concentration is not directly measured. Therefore, the sodium concentration must be computed indirectly using measured pH corrected to 25° C. and measured $PO_4$. Using the previous assumption that only sodium and phosphate are active in determining congruency, the sodium concentration, Na, can be computed, assuming electroneutrality in the boiler water, using a charge balance equation.

Figure 4:
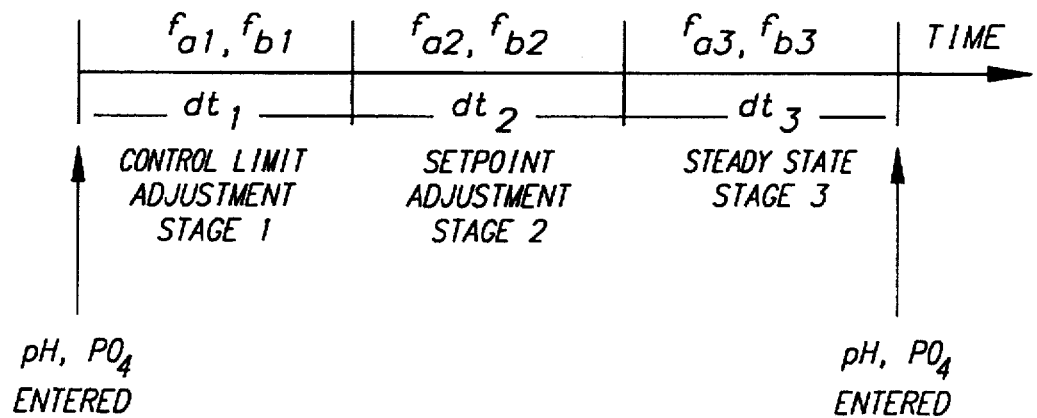
FIG. 4 is a time line diagram of the MACC feed program.

The MACC controller 52 feed program consists of three stages, as shown in FIG. 4. During the first stage, chemical pumps 34A and 34B are held at the constant feed rates, $f_{a1}$, $f_{b1}$ for a length of time, $dt_1$ so as to bring the $Na/PO_4$ ratio and phosphate within their control limits. Similarly, the pumps 34A and 34B are held at $f_{a2}$, $f_{b2}$ for time interval, $dt_2$, in order to bring the $Na/PO_4$ ratio and phosphate to their setpoints. Finally, once these setpoints are reached, the steady state feed rates, $f_{a3}$, $f_{b3}$ are used to maintain them. Each time a new pH, $PO_4$ measurement is entered by the operator, the feed program calculates these eight parameters ($dt_1$, $dt_2$, $f_{a1}$, $f_{b1}$, $f_{a2}$, $f_{b2}$, $f_{a3}$, and $f_{b3}$), as will be described later.

Figure 5:
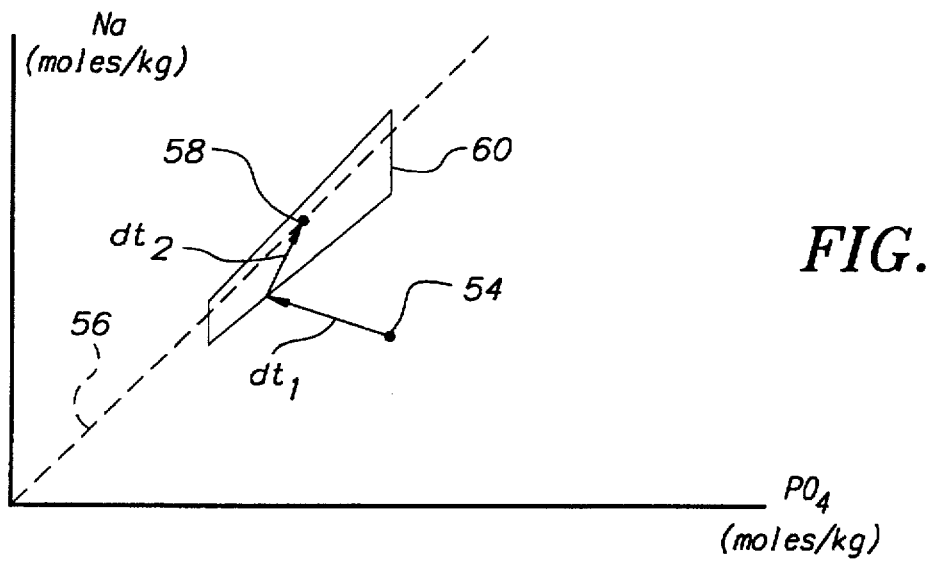
FIG. 5 is a diagram of the congruency line and target region.

The goal of the MACC system 20 is to choose the optimal feed program. As shown in FIG. 5, the optimal feed program can be defined as:

1) bringing the current boiler water Na/PO$_4$ ratio and phosphate concentrations (point 54) within their control limits as soon as possible (i.e., minimizing dt$_1$).
2) once within these control limits, bringing the Na/PO$_4$ ratio and the phosphate to the setpoint as soon as possible (minimizing dt$_2$).

Chemically correct congruent control is obtained by choosing a narrow control range around the setpoint for Na/PO$_4$ ratio, and choosing as wide a control range as acceptable for phosphate. This allows the algorithm to focus on getting the critical Na/PO$_4$ ratio correct initially, except when phosphate levels are so far off that they present an equally critical control problem. For this reason, by default, the MACC controller 52 automatically defines a narrow control range around the congruency setpoint, the width of which reflects the Na/PO$_4$ ratio variation associated with instrumental and operational pH variability. In particular, there is shown in FIG. 5, the desired congruency line 56 for sodium and phosphate and the ideal congruency setpoint 58. The pH and phosphate control limits define a target region 60 around the setpoint 58.

The first step in determining the optimal feed program is to estimate the blowdown flow rate, B, and the feedwater contaminant ingress, L. As shown in FIG. 4, the MACC controller 52 stores the previous as well as the currently entered PO$_4$ and pH entries, which are referred to as "lastPO4, lastpH, PO4 and pH", respectively.

Equation #2 is used along with the known feed program between samples (i.e., the previously estimated $f_{a1}$, $f_{b1}$, etc.) to back-calculate the blowdown flow rate, B. A blowdown flow rate is estimated and then Equation #2 is applied to each of the three feed stages in turn in order to predict what the concentration would have been had the estimated blowdown flow rate been the actual blowdown flow rate. In particular, Equation #2 is sequentially solved as follows:

$$PO41 = ((f_{a1}*PO4_a + f_{b1}*PO4_b)/B)*(1 - e^{(-dt1/\tau)}) + lastPO4*e^{(-dt1/\tau)} \quad \text{(Equation 2A)}$$

$$PO42 = ((f_{a2}*PO4_a + f_{b2}*PO4_b)/B)*(1 - e^{(-dt2/\tau)}) + PO41*e^{(-dt2/\tau)} \quad \text{(Equation 2B)}$$

$$PO43 = ((f_{a3}*PO4_a + f_{b3}*PO4_b)/B)*(1 - e^{(-dt3/\tau)}) + PO42*e^{(-dt3/\tau)} \quad \text{(Equation 2C)}$$

wherein the concentration at the end of stage 1 is substituted for the initial concentration at the beginning of stage 2, etc.

If the estimated blowdown flow rate is exactly right, then PO43 (the predicted concentration at the end of stage 3) will be equal to PO4, the measured phosphate in the boiler. If PO43 is less than PO4, the estimated blowdown flow rate, B, must be too high (i.e., it blows out too much phosphate). In other words, the greater the blowdown estimate, the smaller the predicted phosphate concentration. This uniform PO4 vs. blowdown response implies that a particularly simple and reliable method, known as bisection, can be used to find the blowdown estimate that is exactly correct.

As stated earlier, assuming electroneutrality of the boiler water, the current and preceding pH and PO4 measurements are used in a charge balance equation to calculate Na concentrations, in particular, "lastNa and Na". In a manner exactly analogous to the manner in which the blowdown was determined via phosphate, the feedwater contaminant ingress, L, is determined using Equation #3 sequentially and by comparing the Na predicted using an estimated L with actual Na estimated from pH and PO4.

The root finding process described above can fail in three ways. First, it may turn out that no reasonable blowdown flow rate is consistent with the starting and ending phosphate measurements. For example, if the blowdown valve 28 were completely turned off (B=0), the predicted phosphate at the end of stage 3 would be at its maximum. A PO4 entry greater than this maximum would be inconsistent with the model, since no possible adjustment of the blowdown could match the given data. Similarly, if successive pH entries that lead to outrageously large (physically impossible) FCIs (e.g., due to measurement error, data entry errors by the operator, erroneous model parameters, etc.), the MACC controller 52 sets particular error flags (E_INCONSISTENT_PO4 or E_INCONSISTENT_PH flags) in the MACC software 48 and then continues to use the previously estimated feed program.

The third way that the root finding can fail is that subjecting lastpH, lastPO4, pH, and PO4 to small changes consistent with their variability results in relatively large changes in the estimated steady state boiler concentrations. The user can specify both the expected variability in the inputs, and the acceptable percentage variation in the steady-state concentrations induced by this variability. If the expected variations in pH and phosphate lead to unacceptably large variations in estimated steady-state boiler concentrations, the E_INDETERMINATE flag is raised, and MACC controller 52 continues to use the previously estimated feed program. A common situation that raises the E_INDETERMINATE flag is when the interval between samples is much smaller than the boiler residence time.

Given any feed program (dt$_1$, dt$_2$, dt$_3$, $f_{a1}$, $f_{b1}$, $f_{a2}$, $f_{b2}$, $f_{a3}$, and $f_{b3}$), blowdown (B) and feedwater contaminant ingress (L), and the initial boiler phosphate concentration and pH, the Equations #2, #3 and the charge balance equation, can be used to predict Na and PO$_4$ concentrations for any time. In principle, all possible feed programs could be calculated and the one feed program that brought the boiler sodium and phosphate concentrations within the target region 60 (and, secondarily, to the setpoint 58) as quickly as possible, would be selected. However, such a brute force approach is impractical if not impossible. On the other hand, the MACC controller 52 eliminates the need to use such a brute force method by way of a series of easily solved geometrical problems using a boiler state space diagram, as discussed below.

In its two component forms, the boiler state space (FIG. 6) is visualized as a simple X-Y graph with PO$_4$ (boiler phosphate concentration) on the X axis and Na (boiler sodium concentration) on the Y axis. It is called a state space diagram because each possible state of the model boiler corresponds to a point in the X-Y "space". For any given chemical pump 34A feed rate ($f_a$), chemical pump 34B feed rate ($f_b$), FCI (L), and blowdown flow rate (B), the successive "states" (PO$_4$, Na concentrations) that the boiler can assume over time trace out a curve in this state space.

Generally, the boiler state space permits the visualization of both the phosphate exponential (Equation #2) and the sodium exponential (Equation #3) simultaneously depending on their respective current concentrations and the steady state concentrations.

In particular, the curves begin at the point representing the current PO$_4$ and Na boiler concentrations. Furthermore, according to Equations #2 and #3, the boiler concentrations must attain their steady state levels (t=∞), namely:

$$PO4(t=\infty) = (f_a*PO4_a + f_b*PO4_b)/B \quad \text{(Equation #4)}$$

$$Na(t=\infty) = (f_a*NA_a + f_b*Na_b + L)/B \quad \text{(Equation #5)}$$

Multiplication of both sides of the above equations by B shows that they simply state that, in equilibrium, the flow of PO$_4$ or Na into the boiler equals the flow out of it.

Hence, the curve is defined by a straight line between the initial point (PO4(0), Na(0)) and the final point (PO4(∞), Na(∞)). The reason for this is that in the time domain Equations #2 and #3 the same time constant,τ, (M/B), governs the exponential approach to the equilibrium concentration for both phosphate and sodium. Thus the fraction of the total difference between the starting and final concentrations after any time t is the same for both $PO_4$ and Na; changes in "y" (Na) are always in the same proportion to changes in "x" (PO4)—the definition of a straight line. Just as its x and y components are, likewise the exponential approach of the point itself (which is the superposition of these "x" and "y" components) to the equilibrium point in state space is also governed by this same time constant.

Note that, although the line traced out is straight, the rate at which the point moves along the line varies. In the beginning the point moves at the fastest rate; as it asymptotically approaches the final equilibrium point the velocity approaches zero (which corresponds with the exponential functions in the time domain, i.e., the derivative of each exponential yields its greatest velocity at the initial state and is zero at the equilibrium point). In fact, the time at which any fraction of the total distance along that line will be traversed is given by using Equations #2 and #4. The following equations provide the time that corresponds to a particular fraction of the total distance to the equilibrium point that remains to be traversed:

$$t=-(M/B)*\ln((PO4(t)-PO4(\infty))/(PO4(0)-PO4(\infty)))  \quad \text{Equation \#6}$$

and using Equations #3 and #5 for sodium, $$t=-(M/B)*\ln((Na(t)-Na(\infty))/(Na(0)-Na(\infty))) \quad \text{Equation \#7}$$

These simple, straight line, state space trajectories provide a method of considering the entire range of boiler concentrations that are attainable from a given starting point using a particular set of feed rates.

The possible "end points" of these straight lines (Equations #4 and #5) are defined by the range of the chemical feed pumps 34A and 34B:

$f_{amin}<=fa<=f_{amax}$ where $f_{amin}$ is usually 0;

$f_{bmin}<=fb<=f_{bmax}$ where $f_{bmin}$ is usually 0.

Recasting Equations #4 and #5 into a vector format, and in light of the above constraints, the set of all possible end points (steady state feed rates) forms a parallelogram (i.e., a linear combination of the two feed concentration vectors, $f_a$ and $f_b$) in the state space hereinafter known as the pumpable region 62:

$$\begin{pmatrix} PO4(\infty) \\ Na(\infty) \end{pmatrix} = f_a \begin{pmatrix} (PO4_a/B) \\ (Na_a/B) \end{pmatrix} + f_b \begin{pmatrix} (PO4_b/B) \\ (Na_b/B) \end{pmatrix} + \begin{pmatrix} (0) \\ (L/B) \end{pmatrix} \quad \text{(Equation \#8)}$$

Figure 6:
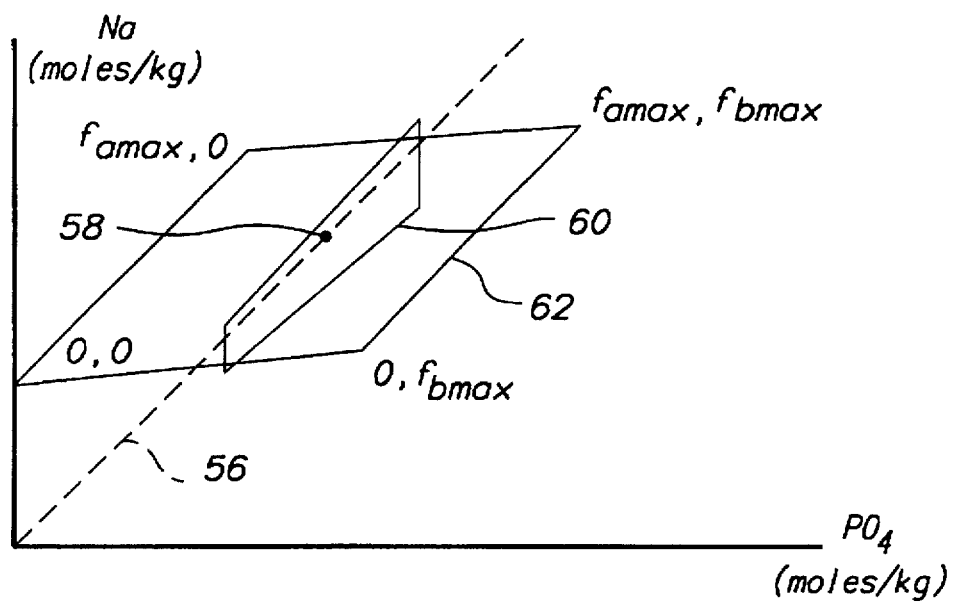
FIG. 6 is the boiler state space diagram.

This pumpable region 62 is shown in FIG. 6. Note that each point in the pumpable region 62 uniquely defines the feed rates ($f_a$, $f_b$) associated with the corresponding steady state boiler concentrations, provided only that the concentrations in chemical pumps 34A and 34B are linearly independent (in other words, $PO4_a*Na_b-PO4_b*Na_a$ must not be equal to 0). This is an important requirement of the MACC controller 52.

By holding the feed rates constant, the boiler state space point is moved along a straight line towards the final, steady-state, concentrations associated with those feed rates. Moreover, the time it takes to reach any intermediate point along this state space trajectory is given via Equations #6 and #7. Determining the pumpable region 62 by the MACC controller 52 is known as "scaling the map" and once this is completed, the controller 52 is ready to proceed with determining stage 1 of the feed program.

The objective of stage 1 of the feed program is to bring the boiler water concentrations into the target region 60 as quickly as possible, as discussed earlier with respect to FIG. 5. Thus, it is necessary for the MACC controller 52 to determine a state space trajectory 64 that begins at the current boiler water concentrations 54, and crosses into the target region 60, as shown in FIG. 6.

Figure 7:
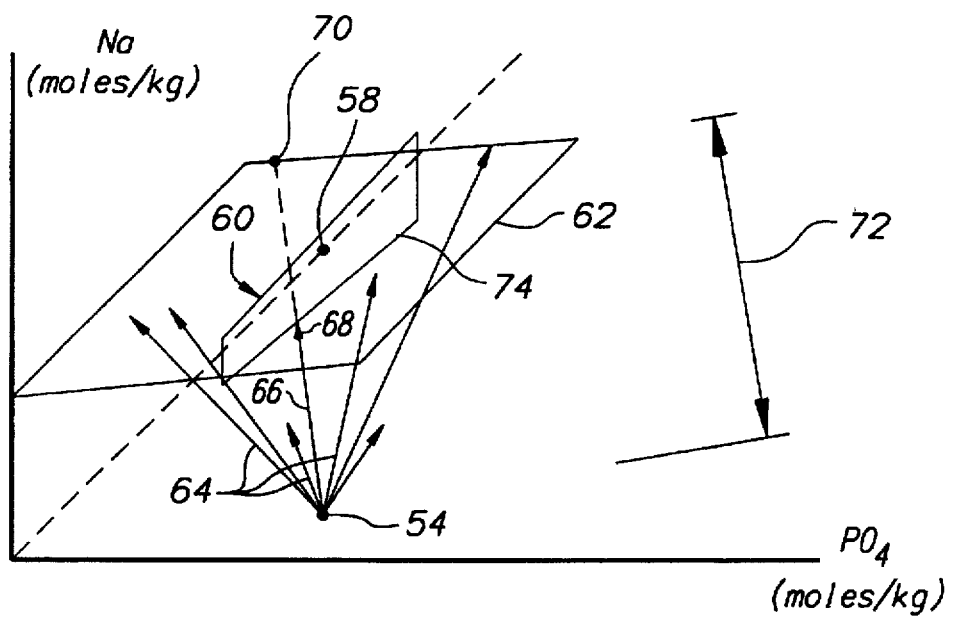
FIG. 7 is the boiler state space diagram depicting various feed programs.

However, the only state space trajectories 64 available are those that correspond to actual feed pump rates, in other words, line segments which begin at the current point 54 and end in the pumpable region 62. In general, some of these segments (FIG. 7) will cross into the target region 60, and some will not. In the special case in which none of these line segments cross into the target region 60, the flag E_BOXUNREACHABLE is set, and the MACC controller 52 uses those feed rates that will drive the current boiler fluid concentrations 54 towards the area of the pumpable region 62 that is closest to the target region 60.

Otherwise, at least one such segment/trajectory 66 crosses into the target region 60. By virtue of Equations #6 and #7, if the end point 68 of this trajectory 66 is not on the perimeter of the pumpable region 62, the time that it takes to reach the target region 60 can always be reduced by replacing this end point 68 by the point 70 on the pumpable region's 62 perimeter found by extending the line segment 66 beyond the original end point 68. Intuitively, by making the distance 66 to the target region 60 a smaller fraction of the entire trajectory 72, the time to reach the target region 60, which depends only on the fraction of the total trajectory that needs to be traversed, is reduced. Note that any such trajectory 66 will reach the perimeter of the target region 60 before it reaches the interior; thus "target region" and "target perimeter" are equivalent.

Figure 8:
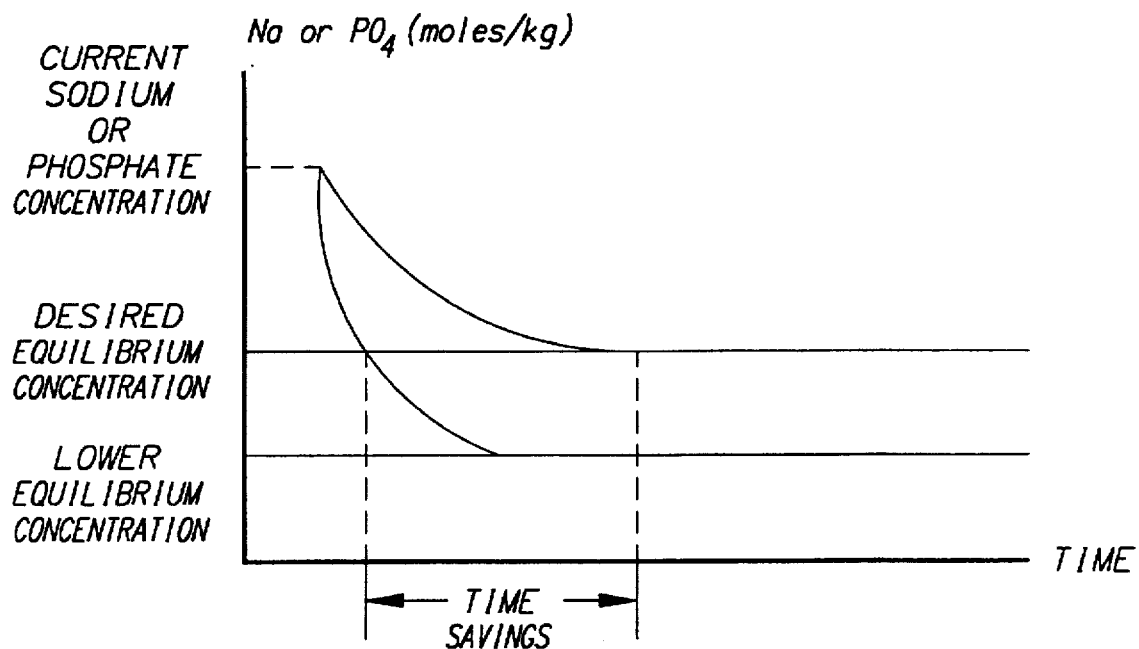
FIG. 8 is a time domain diagram depicting the minimization of the first stage period.

Alternately, when this "endpoint projection in the state space" is viewed in the time domain, by the MACC controller 52 selecting a feed rate combination that will yield equilibrium concentrations beyond the desired equilibrium concentrations, the exponential will reach the desired equilibrium concentrations in a shorter time than if the exact feed rate combination for the desired equilibrium concentration were used (FIG. 8).

Figure 9:
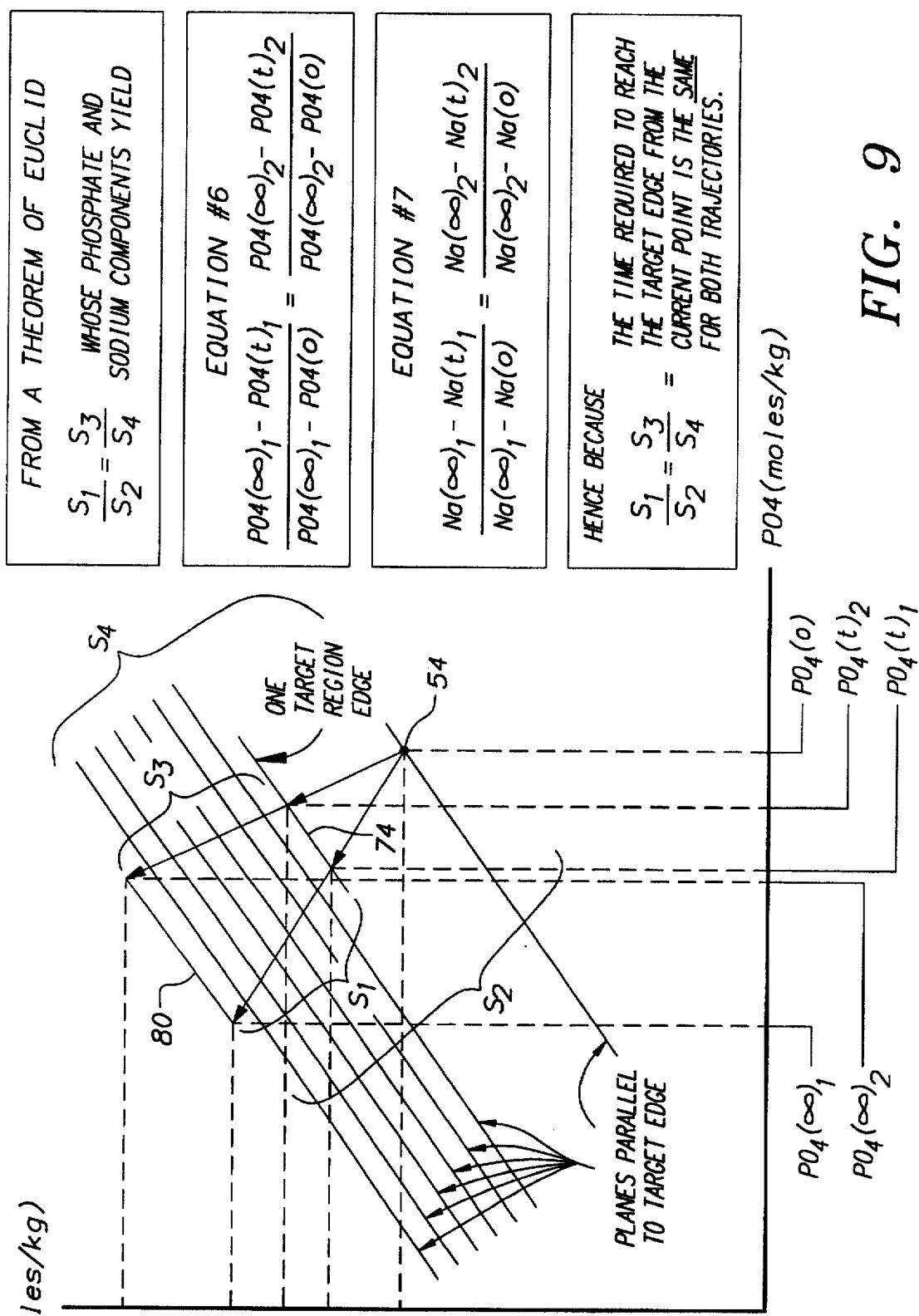
FIG. 9 is a diagram depicting two feed rate trajectories having similar time periods within the boiler state space diagram.

The next determination that the MACC controller 52 makes is to determine just which pumpable region perimeter point will enable the boiler state space point to reach the target region 60 perimeter in the fastest time. To accomplish this, the MACC controller 52 considers those trajectories that both cross a given edge 74 of the target region's 60 perimeter and end on points in the pumpable region 62 that lie on a line parallel to that edge 74. All such trajectories reach the given edge 74 in exactly the same time. To see this, recall the following theorem of Euclid: if two straight lines in a plane are cut by three parallel lines, the corresponding segments are proportional. As shown in FIG. 9, because of this theorem and Equations #6 and #7, the time required to reach the target edge 74 is the same for any two, and thus all such trajectories.

Figure 10:
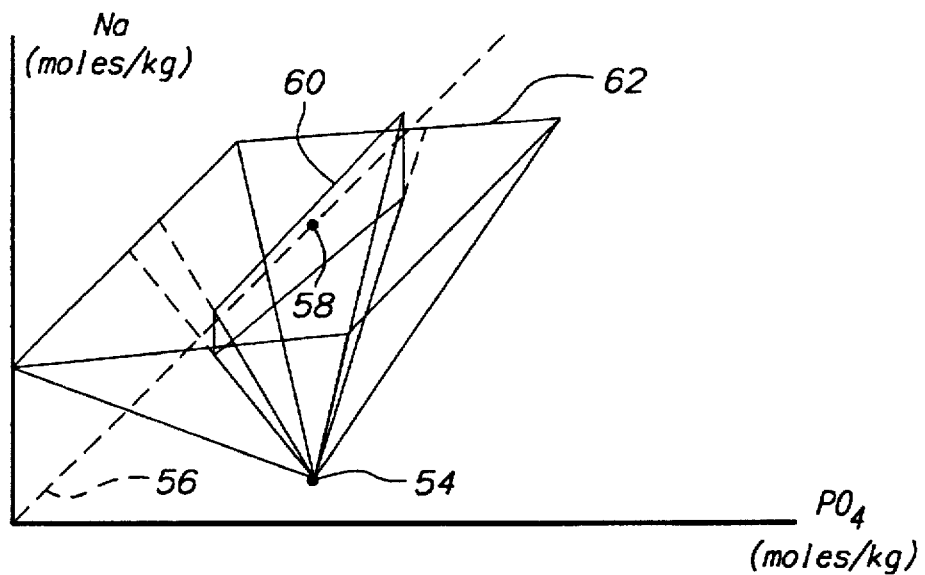
FIG. 10 is the boiler state space diagram depicting the shortest time feed programs.
Figure 10A:
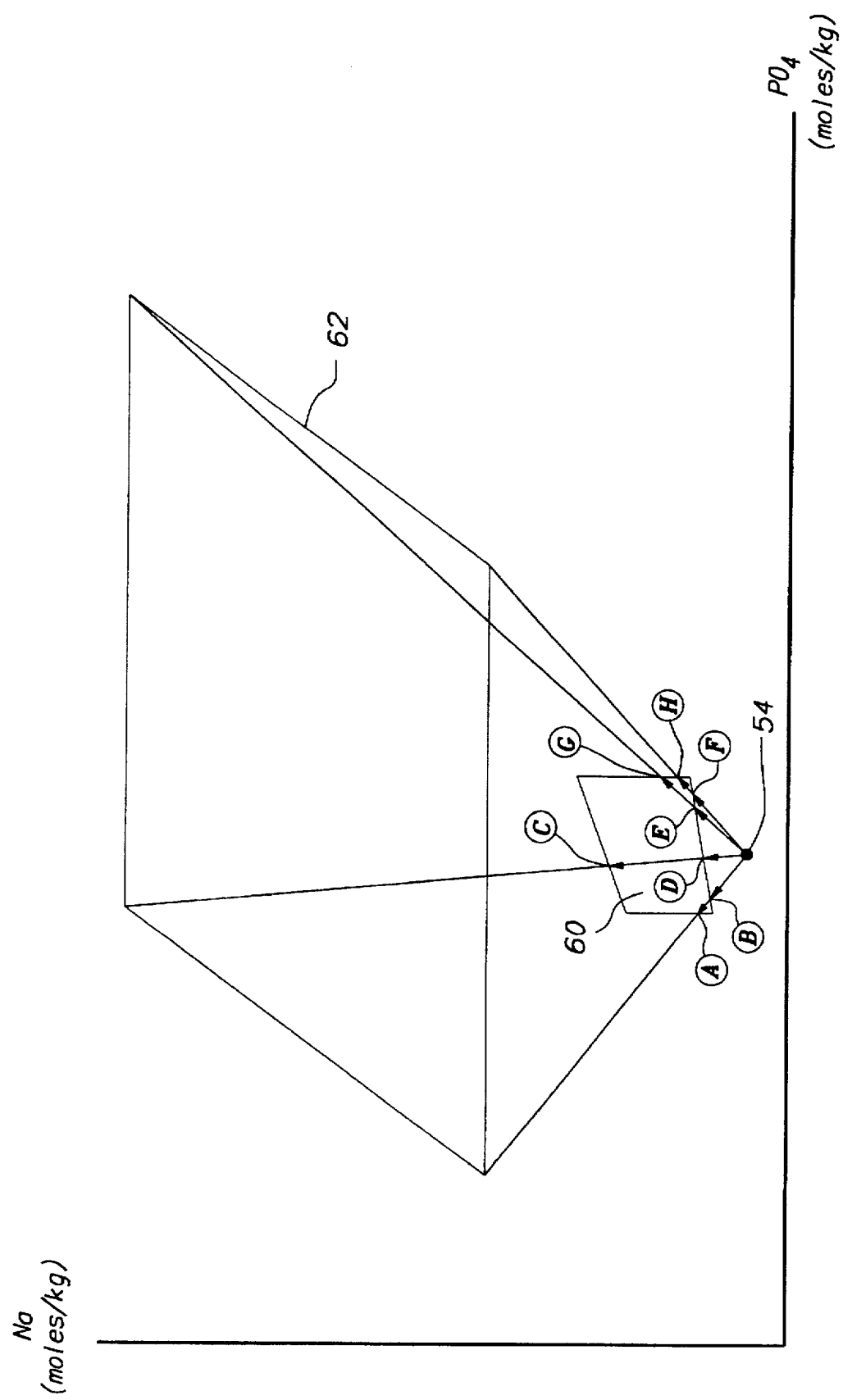
FIG. 10A is a diagram depicting a portion of the candidate shortest-time feed rate trajectories.
Figure 10B:
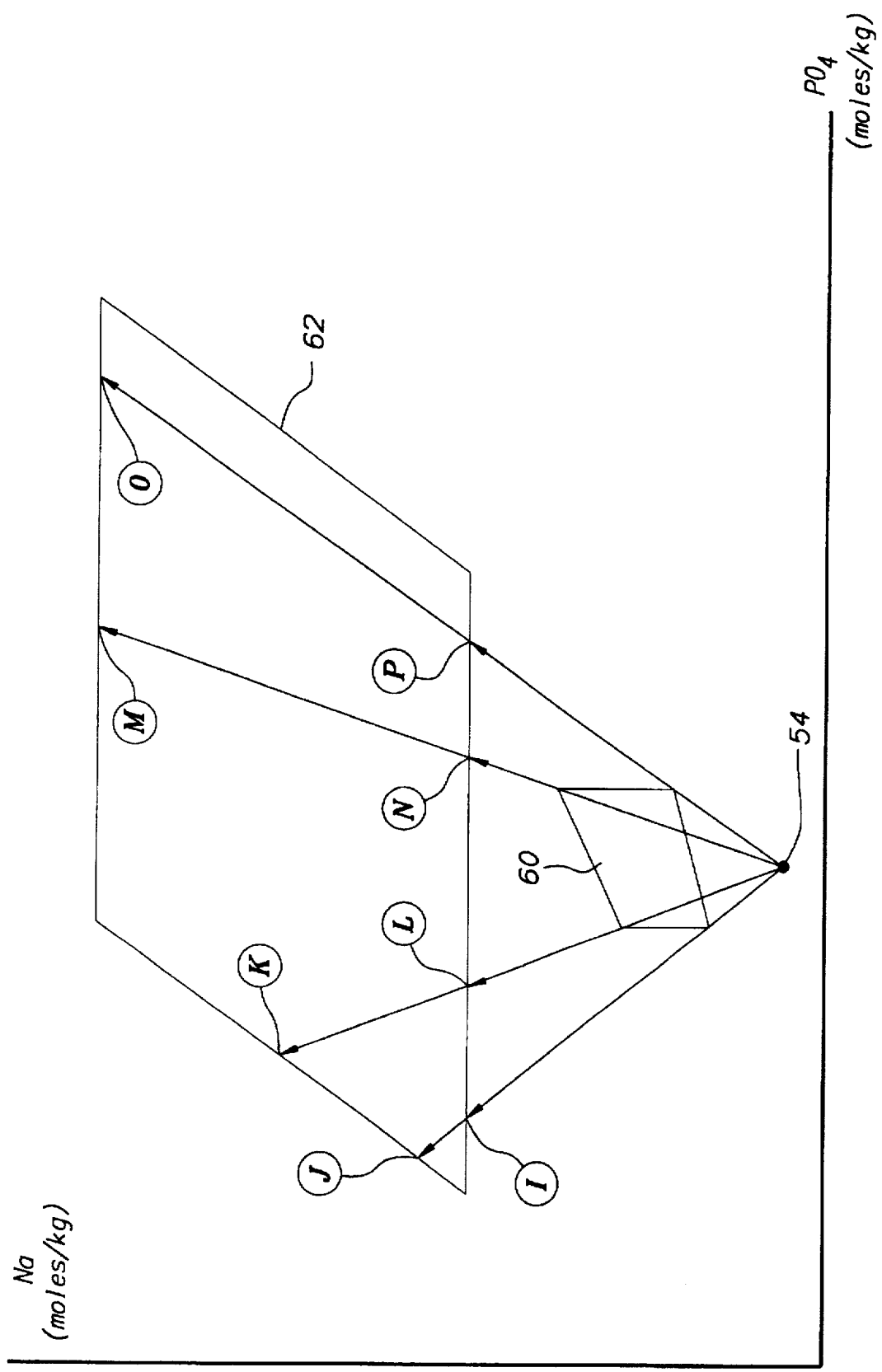
FIG. 10B is a diagram depicting the remainder of the candidate shortest-time feed rate trajectories.

This time can be minimized by choosing end points within the pumpable region that lie on lines parallel to the target edge 74 that are as far away as possible from the initial point (again, c.f. Equations #6 and #7). This implies that the end point of the shortest time trajectory either lies on a vertex of the pumpable region 62, or on one of the trajectories that passes through the endpoints of the target edge (FIG. 10). As can be seen in FIG. 10, there are eight line segments, each having two collinear trajectories that must be evaluated. The MACC controller 52 exploits this fact by checking each of the, no more than 16, such trajectory scenarios, and then using Equation #6 to select the one that reaches the target perimeter in the least time. The 16 candidate trajectory scenarios are established by this analysis being performed on all four target region 60 edges. The 16 candidate trajectories (indicated by letters A–P) can be more easily seen in FIGS. 10A and 10B where each indicated intersection point defines a particular candidate trajectory; the location of the target region 60 with respect to the pumpable region 62 has been altered for clarity.

The optimization problem and solution exploits the so-called fundamental theorem of linear programming; the function to be optimized in the linear programming problem—which, though non-linear,has the monotonicity (i.e., either continuously increasing or continuously decreasing) along straight lines in state space that the fundamental theorem of linear programming requires—is Equation #6 (or #7).

Figure 11:
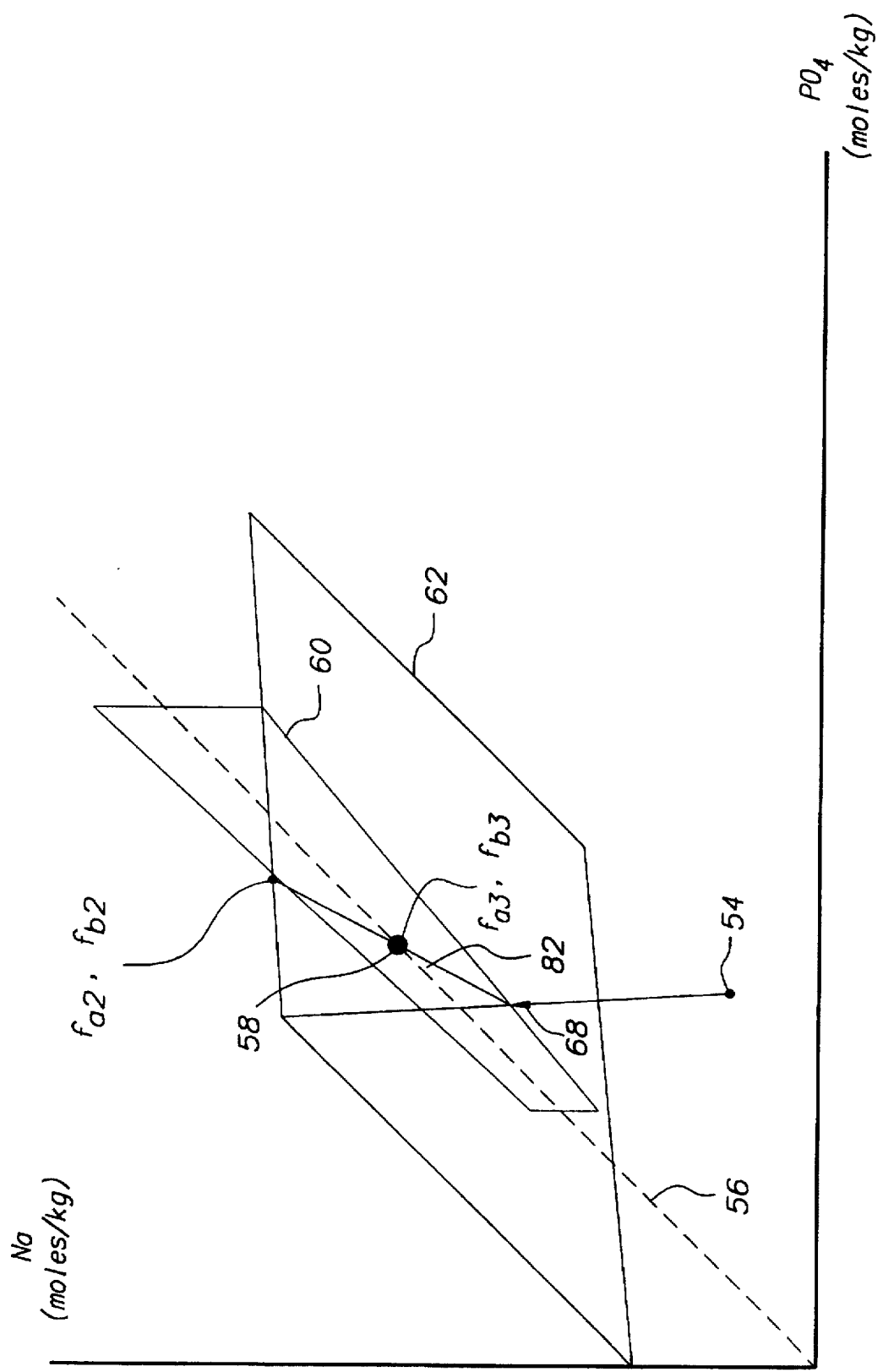
FIG. 11 is the boiler state space diagram for stage 2 and stage 3 of the feed program.

Compared to the complexities of stage 1 adjustment, stage 2 is easier. As shown in FIG. 11, first, the current point 54 is replaced with the point 68 on the target region 60 perimeter found via stage 2, which represents where the boiler concentrations will be at the end of stage 1. This new current point and the setpoint 58 determine a line segment 82; the point on the pumpable region's perimeter found by extending this line segment beyond the setpoint 58 must, by the argument given earlier, correspond to the feed rates ($f_{a2}$, $f_{b2}$) that reach the setpoint 58 in the least time. If there is no such point, the MACC controller 52 sets the E_POINTUNREACHABLE flag and uses the feed rates that correspond to the pumpable point within the target region 60 that is closest to the setpoint.

For stage 3, the MACC controller 52 simply feeds at the feed rates that correspond to the setpoint ($f_{a3}$, $f_{b3}$). Stage 3 remains in effect until the next sample comes in. The durations of stages 1 and 2 are determined via Equation #6 (or #7).

For some applications, it may be desirable to modify the MACC controller 52 algorithms, as discussed below.

Blowdown and FCI Calculation: The blowdown (B) and FCI (L) estimates are exact: they are the roots of equations that have at most one solution. This could introduce problems in boiler systems where the time between pH and $PO_4$ samples is much less than the boiler's residence time. Attempting to feed such data into the current MACC controller 52 will lead to a series of E_INDETERMINATE flags which, in effect, throw away the intermediate data points until enough time has elapsed so that a meaningful feed program determination can be made. Therefore, in boiler systems that utilize such smaller sampling times, it would be more efficient to fit the blowdown and FCI estimates to a series of phosphate and pH measurements; those blowdown and FCI estimates that came closest to the phosphate and pH sequences in a least squares sense could then be used. This change would give the MACC system 20 the desirable property that more frequent operator sampling would always result in better control.

Introduction of Dead Time: Another way that the MACC system 20 could be improved is by explicitly including dead time into the model. The MACC controller 52 currently assumes that the dead time is zero. Limited simulations suggest that this simplification will not degrade control much, provided that dead time is a small percentage of the boiler residence time. However, the impact of dead time depends on many factors; it is likely that at least some of the controlled boilers would experience significantly better MACC control than they would have otherwise obtained had dead time been not been included in the model. On the other hand, conventional congruent control does not explicitly incorporate dead time either.

Optimal Feed Program Determination: the linear programming-related-optimization of the MACC controller 52 feed program determination method could be generalized in a number of ways. Firstly, the setpoint of stage 2 could be replaced with a smaller target region, and then the same computation as in stage 1 could be performed to reach it. This would amount to putting a dead band around the setpoint. In particular, this would entail setting up a new target region around the setpoint and analyzing new feed rate trajectories between the new target region vertices/pumpable region vertices and the new boiler fluid chemical concentrations in a manner similar to that shown in FIGS. 10A and 10B. Once the new target region is achieved, the feed rates corresponding to the setpoint would be maintained. Secondly, there is also no reason to have just two such adjustment stages—there could be any number of target regions, each with its corresponding adjustment stage. Thirdly, there is no need to limit the application of this feed program optimization to just two dimensional state spaces. For example, assuming that polymer measurements were possible, one could introduce a three dimensional state space/target region; if such a system were still limited to two pumps, this would result in a planar pumpable region being embedded in a 3-D space.

Ammonia Correction: Boilers occasionally have ammonia returned to the boiler. Once in the boiler, ammonia masks the normal relationship between the pH and sodium that is used to control the congruency. Ammonia affects the pH. With ammonia present in the boiler water and with no ammonia correction as part of the MACC system 20, the sodium concentration calculated from the measured pH will be higher than is actually correct.

Thus, the following provides a method for correcting the measured pH for the effect of ammonia: an analytical determination of the ammonia in the boiler water is provided by any conventional ammonia measuring means (e.g., colorimetric, ion-selective electrode, ion chromatography) to the MACC controller 52. This ammonia concentration is incorporated into the electroneutrality equation mentioned above, thereby accounting for the ammonia charge contribution and, in particular, subtracting the effect of the ammonia ions from the calculated sodium. Use of the ammonia correcting method can be implemented as an option in the MACC system 20 that the operator can select so that when the pH and phosphate analysis data is inputted into the MACC system 20, the ammonia analysis data can also be entered.

On-Line Input Means: Many boiler operators desire having on-line instrumentation (pH meters/phosphate analyzers) for boiler water parameters rather than using manual data entry of these parameters. Although one of the novel aspects of the MACC system 20 is that it eliminates the need to have on-line instrumentation which is susceptible to breakdown and requires frequent calibration, the MACC system 20 is easily adaptable for such on-line instrumentation in the input means 40.

Three types of on-line measurements are suggested: (1) on-line blowdown flow measurements coupled with manual pH and phosphate concentration measurements (hereinafter referred to as OLBF) and (2) on-line blowdown flow coupled with on-line pH and/or on-line phosphate (hereinafter referred to as OLBF/pH or OLBF/$PO_4$) and, (3) on-line pH measurement coupled with manual phosphate (hereinafter referred to as OLpH). In the third type, blowdown is estimated rather than measured on-line.

In OLBF, the phosphate concentration and pH of the boiler water would still be manually entered every 8 to 24 hours. Between the $PO_4$ and pH entries, all blowdown flow measurements and the continuously varying feed rates resulting from the MACC system 20 calculations would be stored in arrays. These stored blowdown flow values would comprise appropriately filtered values chosen to average out short-term variation.

As discussed earlier, after each entry of pH and phosphate is made, the MACC system 20 estimates the blowdown flow and FCI. Using the blowdown flow measurements made over the interval between samples, the MACC controller 52 can use the successive manual phosphate entries to estimate a boiler phosphate mass imbalance in a manner analogous to the way in which the FCI is estimated. The boiler phosphate mass imbalance represents a measurement of any discrepancy between the expected boiler water phosphate mass and the measured boiler water phosphate mass. The principle difference would be that, for both the FCI and phosphate imbalance estimates, Equations #2A, #2B, and #2C would be expanded to included additional stages so as to incorporate changes in the measured blowdown flow into the model predicted boiler sodium and phosphate.

The feed program updates for the OLBF method occur much more frequently than for the manual method. With the manual method, this estimate will occur after each entry, every 8 to 24 hours. With the OLBF method, these feed program updates are made after every blowdown flow measurement using the current blowdown flow and the last set of manually entered pH and $PO_4$ values. Because there are N blowdown flow samples, where N is the number of distinct blowdown samples (and different feed rates) between pH and $PO_4$ samples, there will be N feed program updates between pH and $PO_4$ samples.

As with the MACC system 20, the optimized feed program would be computed using a state space diagram, except that the diagram would be scaled (c.f. Equation #8) using the currently measured blowdown rate. The initial phosphate and sodium concentrations to be used would be the boiler model-projected phosphate and sodium concentrations; the expanded form of Equations #2A, #2B and #2C (see above), incorporating the OLBF measurements, would be used to determine these projections. The resulting calculated feedrates would then be transmitted to the pumps by the control means 32.

As also discussed earlier, the MACC system 20 uses three stages to reach the setpoint 58. Due to the long time between samples, it is possible that all three stages may be reached in one sampling interval. However, using the OLBF method, there could be as many as 3*N stages; each time the state space and feed program are updated with a new OLBF measurement, three new stages would be generated. In reality, because the updates would be so frequent, the system 20 would rarely get beyond the current stage before another update arrived.

With OLBF/pH or OLBF/$PO_4$, the same steps discussed with OLBF would be carried out. Then, using the measured pH, the boiler water sodium concentration would be estimated. If an on-line $PO_4$ analyzer is used with the MACC system 20, the boiler water sodium concentration can be calculated as before using the charge balance equation. Otherwise, the last phosphate measurement, the on-line blowdown flow measurements and feed rates (obtained since that last phosphate measurement) are then used, along with the expanded form of Equations #2A, #2B, and #2C, to obtain a model-projected phosphate. Using the charge balance equation as before, this model-projected phosphate and the on-line temperature corrected pH measurement are used to estimate a boiler water sodium concentration. In either case, the resulting sequence of boiler phosphate concentrations and/or estimated boiler sodium concentrations are used, along with the differential mass balance equations shown below, to estimate $PO_4$ and/or FCIs.

$M*(d(Na(t))/dt = L\_Na(t) + f_a(t)*Na_a + f_b(t)*Na_b - B(t)*Na(t)$  Equation #9

$M*(d(PO4(t))/dt = L\_PO4(t) + f_a(t)*PO4_a + f_b(t)*PO4_b - B(t)*PO4(t)$  Equation #10

The above equations are solved for $L\_Na(t)$ and $L\_PO_4(t)$, and these instantaneous $L\_Na(t)$ and $L\_PO_4(t)$ estimates are averaged/filtered in such a manner so as to balance the competing goals of responding quickly to FCIs vs. estimating those FCIs accurately. If the FCIs are tracked closely, the upstream series ($f_a(t)$, $f_b(t)$) needs to be shifted to incorporate deadtime explicitly; otherwise, it is necessary to use averaged/filtered $L\_Na(t)$ and $L\_PO4(t)$ that are representative of time intervals large enough so that the impact of deadtime on these averaged/filtered estimates is negligible.

These averaged/filtered $L\_Na(t)$ and $L\_PO_4(t)$, and blowdown flow(t) are used, along with either the measured or model projected current boiler phosphate and sodium concentrations, to continuously update the MACC system 20 state space diagram and associated optimized feed program.

With the last option, OLpH, a similar set of calculations are conducted. The MACC system 20 model boiler parameters are updated as before whenever manual phosphate analyses are entered. The on-line pH and model-projected phosphate concentration are used to continuously update the FCI estimate and thereby the MACC system 20 feed program, in a manner analogous to OLBF/pH, but using estimated, rather than measured, blowdown flow rates.

It should be noted that with all of these on-line MACC system 20 options, control of the chemistry is subject to the normal deadtime constraints present with any automated control scheme.

Multiple Boiler Control: The MACC system 20 is readily adaptable to controlling multiple (e.g., ten) boilers 22 at a customer's facility. To that end, the particular boiler parameters (e.g., boiler size) can be manually entered into the MACC system 20 and the two feedstreams 30A and 30B can be controlled through a solenoid (not shown) that switches the feedstream flows to a particular boiler based on boiler water chemistry, i.e., the boiler water that is in the least desirable state will receive the MACC system 20 congruent control initially.

Note: the definition of the word "automatic" as used in this specification with respect to the MACC system 20 refers to all operations, actions, calculations, pumping and other determinations but excluding the manual removal of the blowdown sample from the blowdown flow, manual insertion of the sample into the analyzer, and operator entry of the chemical data into the computer 42. In other words, the presence of human intervention in one aspect of the invention does not negate the automatic operation based on a manually-entered input (e.g., measured phosphate concentration). In addition, operator response to automatically-generated error messages, alarms, etc. do not negate the automatic characteristics of the invention.

Figure 12:
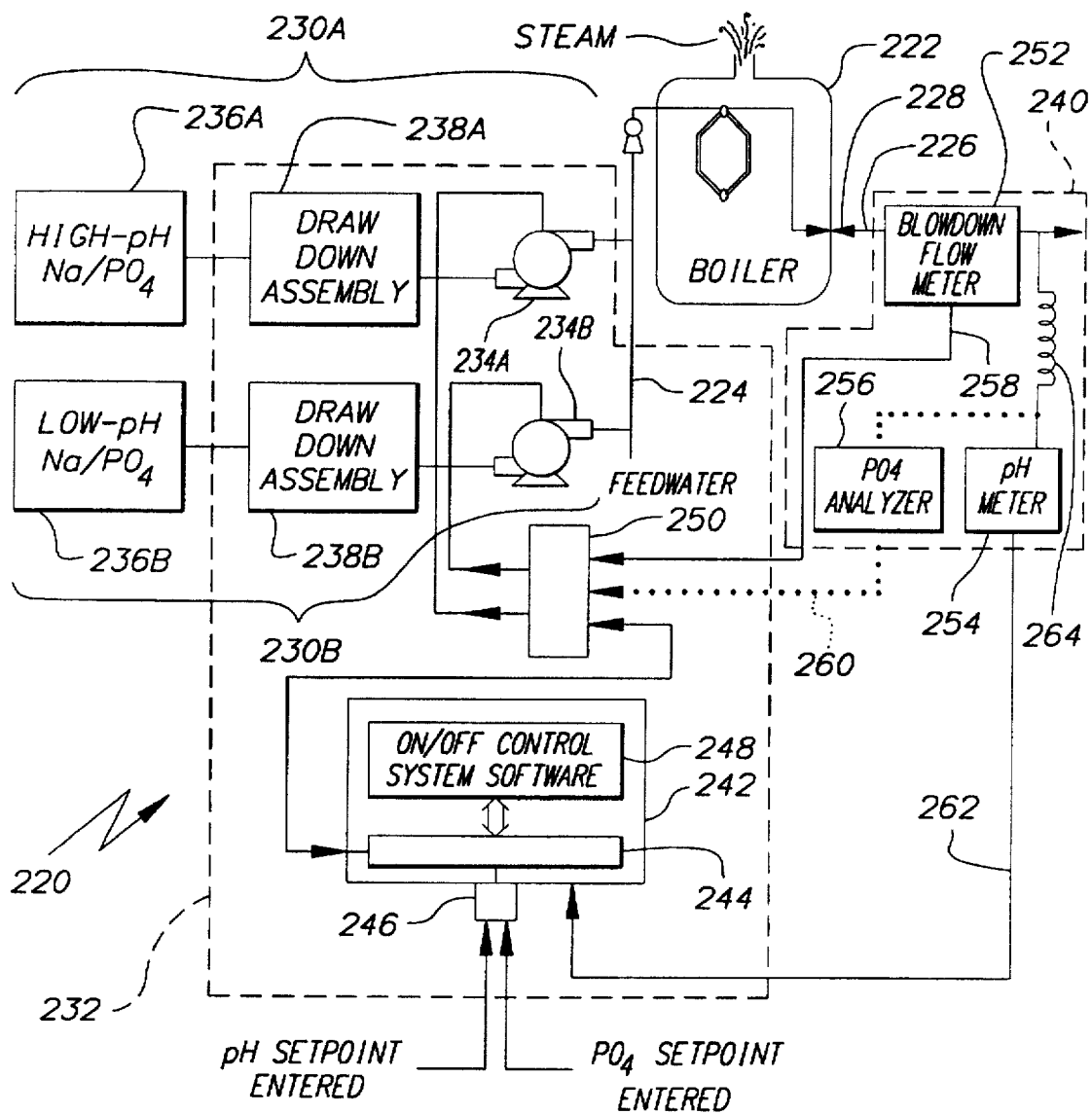
FIG. 12 is a block diagram of an alternative embodiment, the ON/OFF control system.

As shown in FIG. 12, there is shown a second embodiment of an automatic congruent controller system 220, hereinafter known as the ON/OFF control system 220. As with the MACC system 20, the ON/OFF control system 220 controls two interdependent variables, namely, phosphate and sodium, the latter by way of monitoring the pH.

As stated earlier with respect to the MACC system 20, all subsequent references to sodium and/or to the sodium-to-phosphate ratio (Na/PO$_4$) of the boiler water refers to that sodium which interacts with the phosphate to maintain the boiler water so as to inhibit corrosion. This is also referred to as the "effective sodium" or the "effective sodium-to-phosphate ratio."

The ON/OFF control system 220 is arranged to control water treatment chemicals to be introduced into an industrial boiler 222 by way of the feedwater 224 to the boiler 222. The boiler 222 has an effluent flow (hereinafter known as blowdown flow 226) and a blowdown valve 228. As stated previously regarding the MACC system 20, the ON/OFF control system 220 does not control the blowdown flow 226 via the blowdown valve 228. In fact, one of the distinguishing features of the ON/OFF control system 220 over conventional boiler fluid control systems is that the blowdown flow 226 varies independently of the ON/OFF control system 220.

Figure 13:
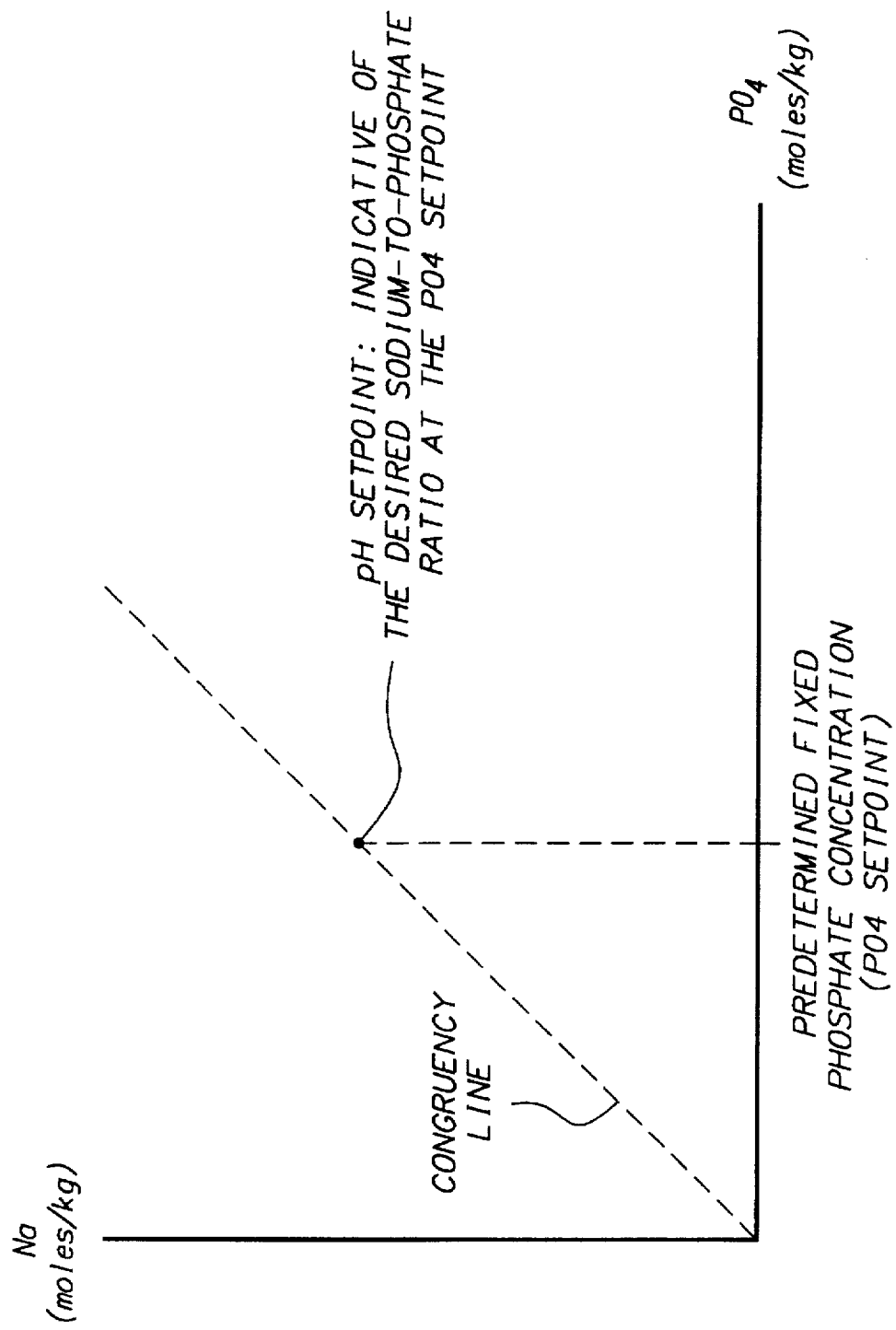
FIG. 13 is a diagram depicting the ON/OFF control system operation around the pH setpoint at a fixed phosphate concentration.
Figure 14A:
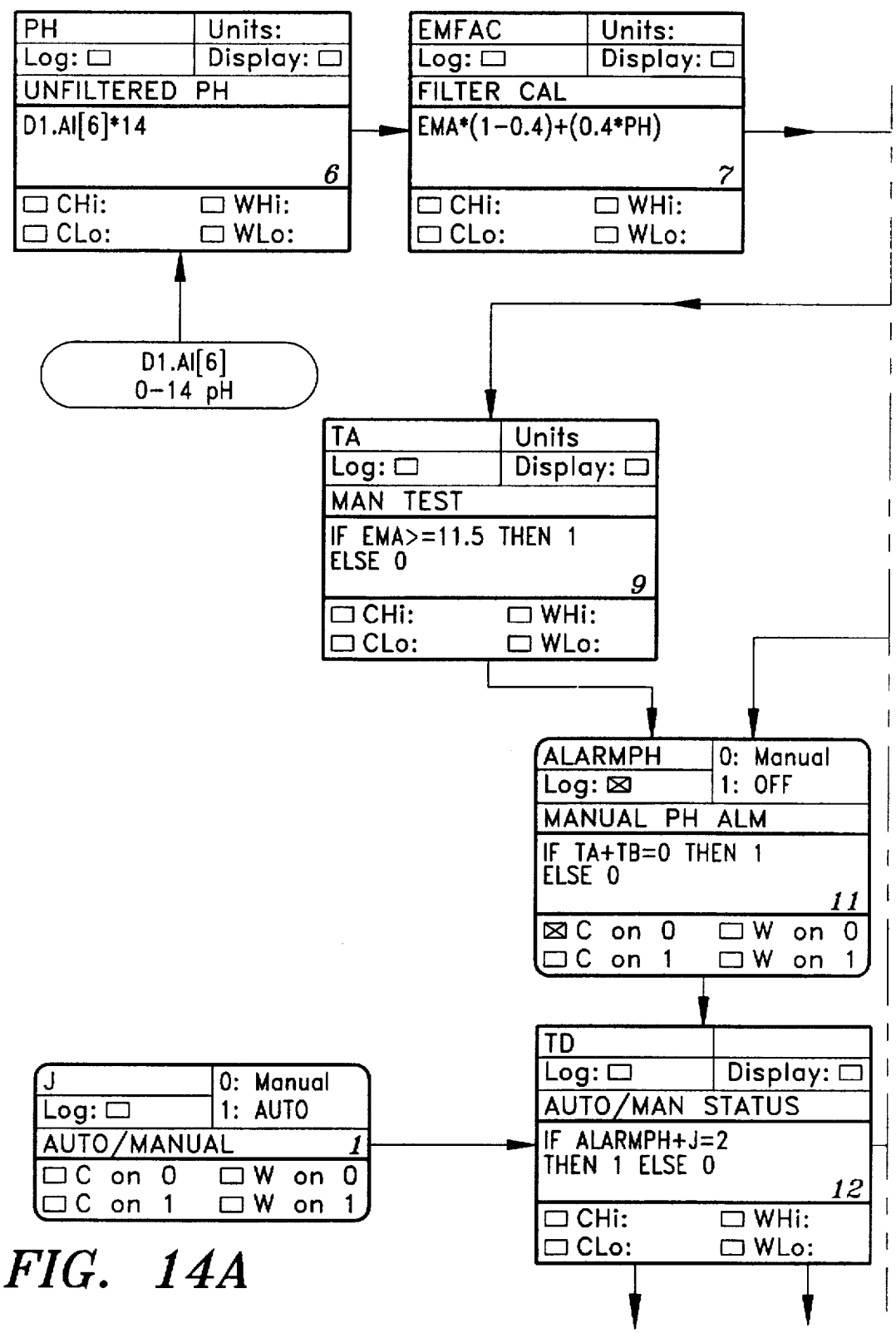
FIGS. 14A, 14B, 14C, 14D, 15A, 15B, 16A, 16B, 17, 18A, 18B, and 18C constitute a control block diagram for the software of the ON/OFF control system.
Figure 14B:
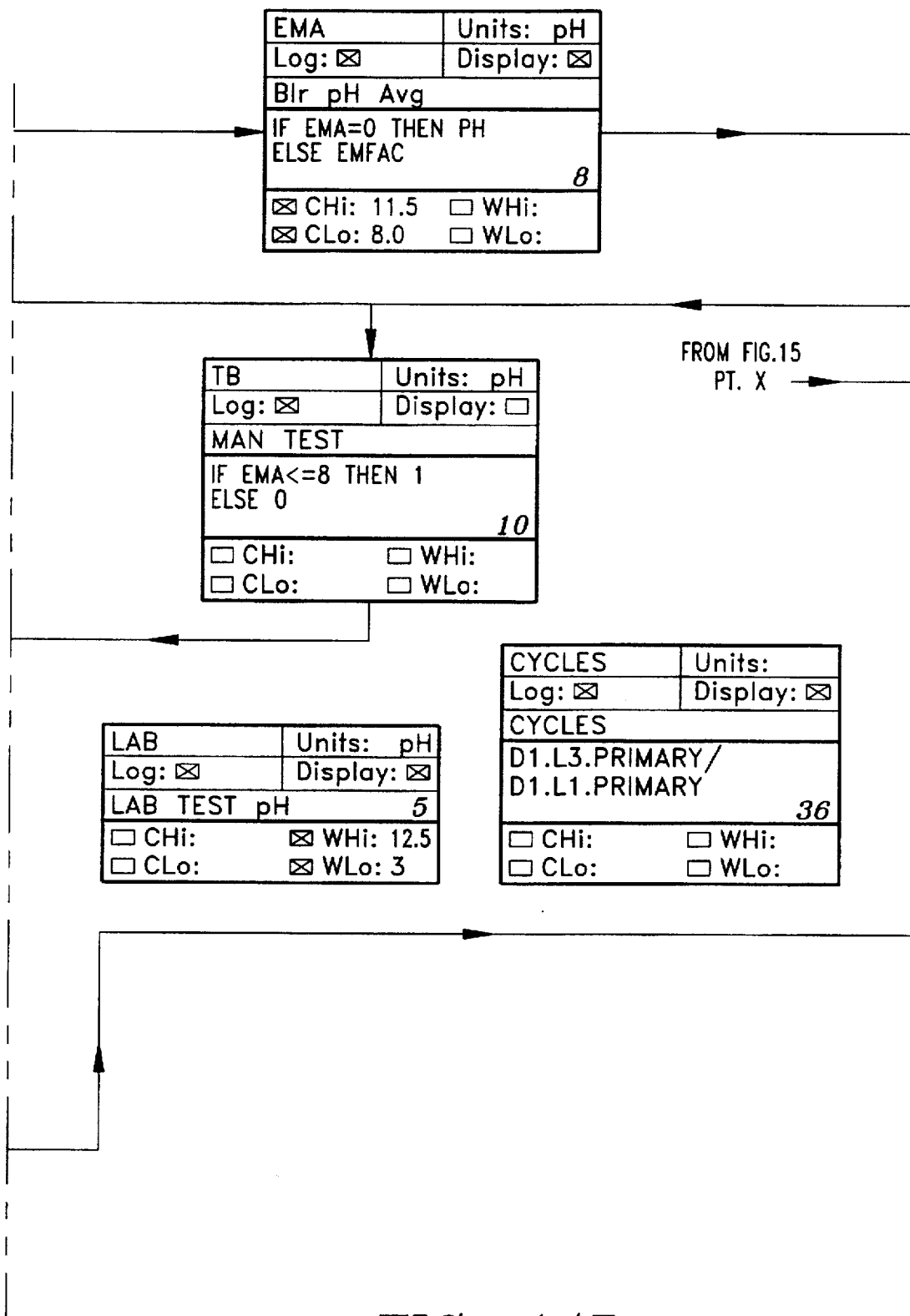
Figure 14C:
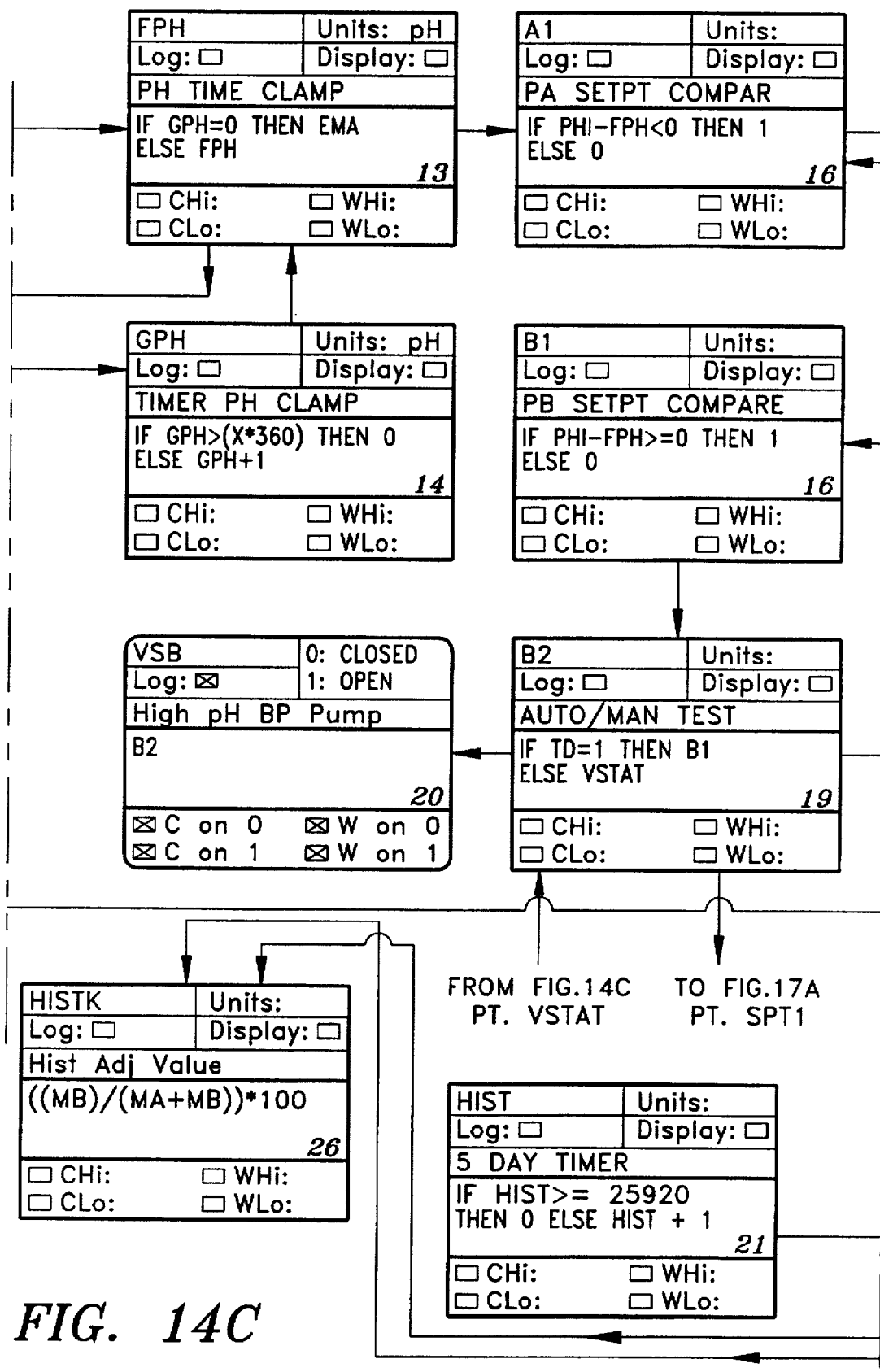
Figure 14D:
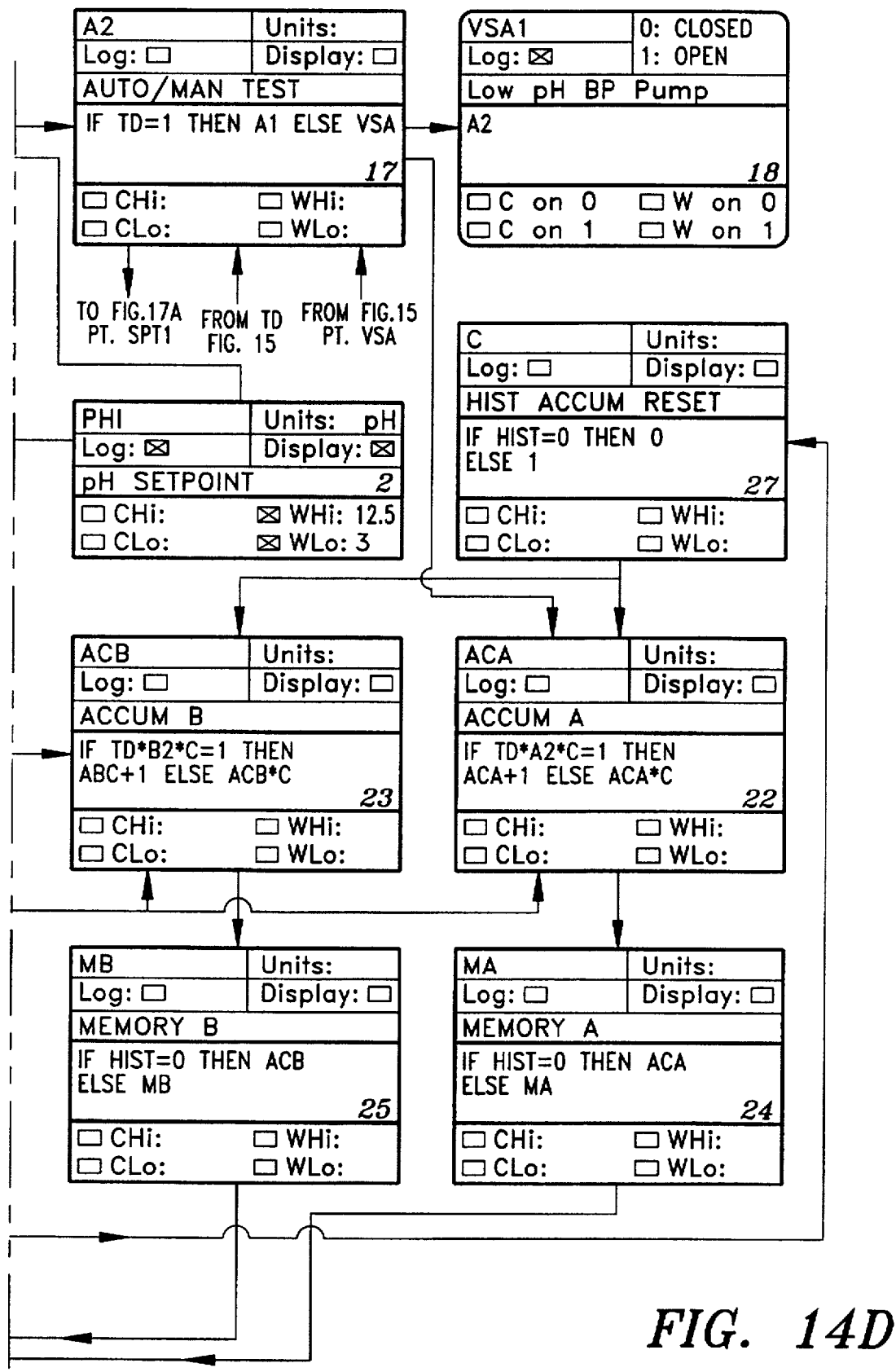
Figure 15A:
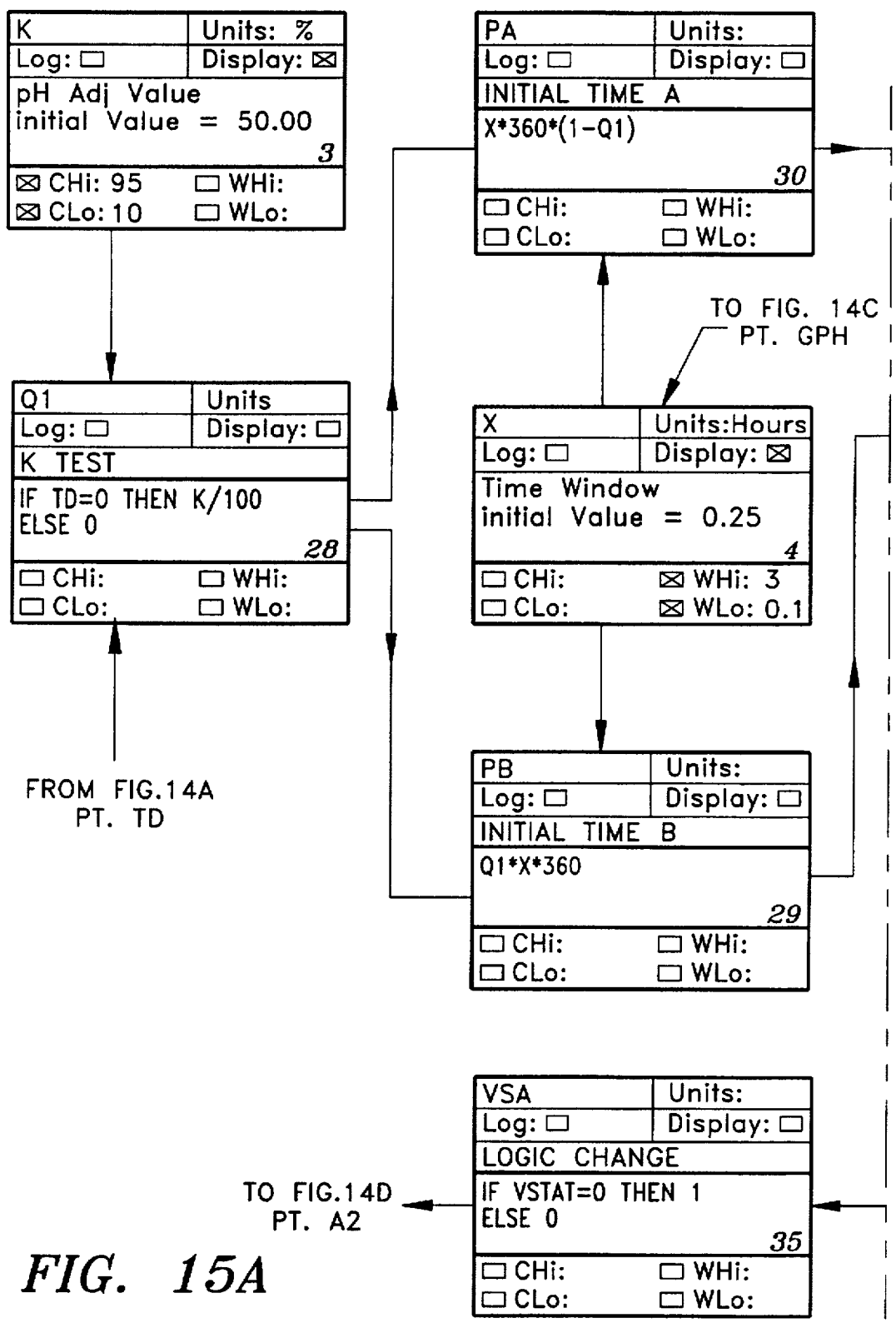
Figure 15B:
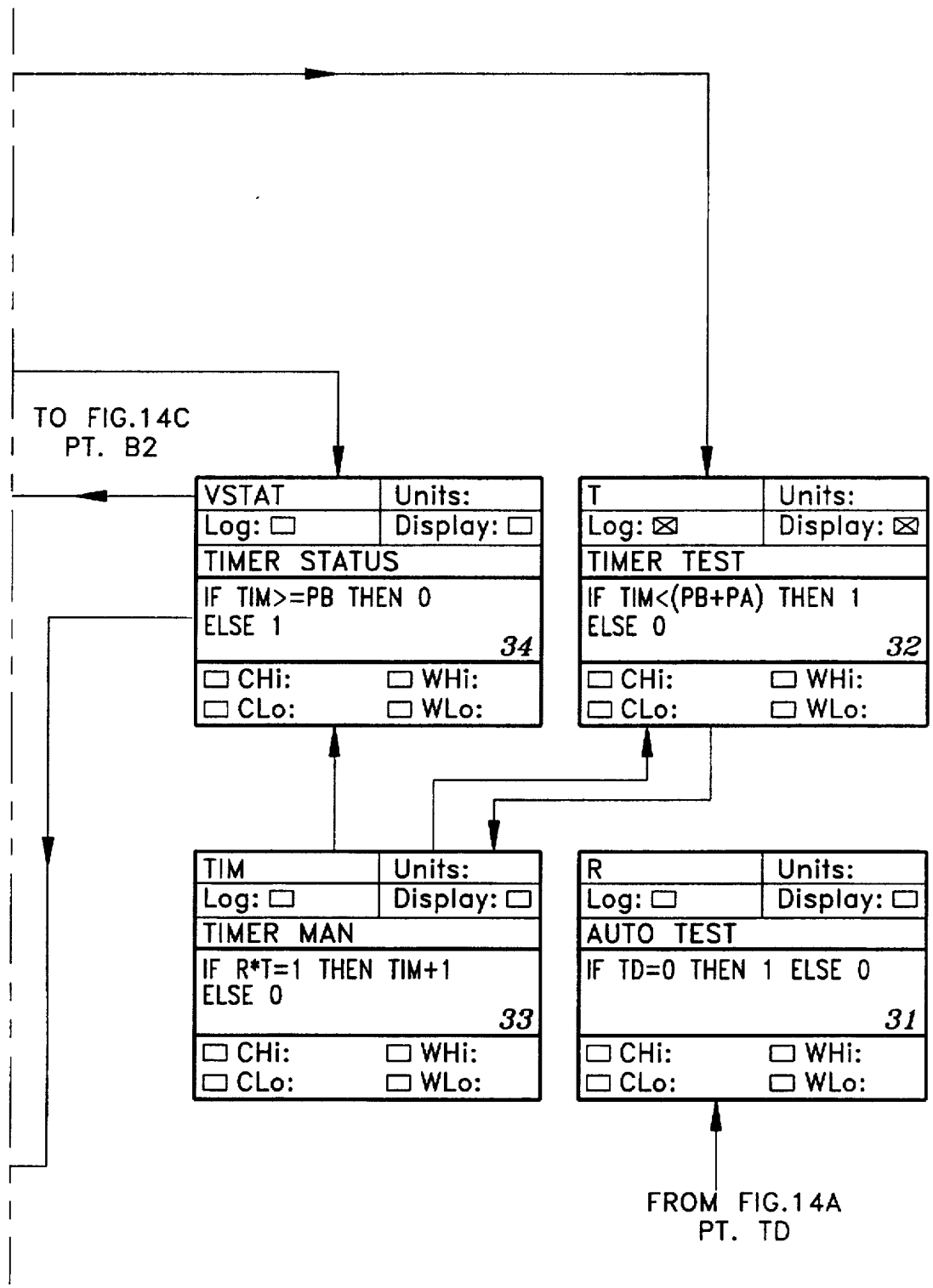
Figure 16A:
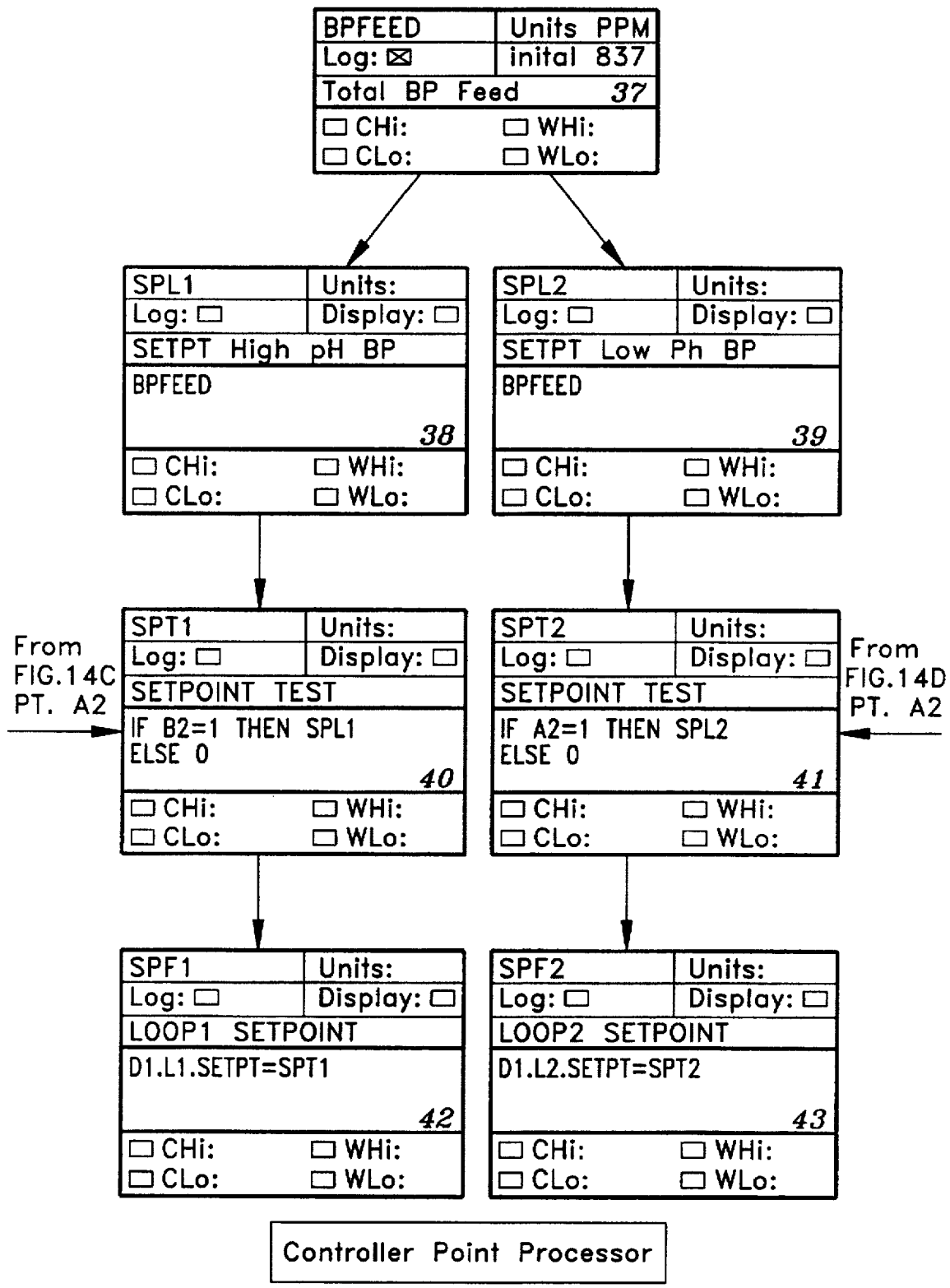
Figure 16B:
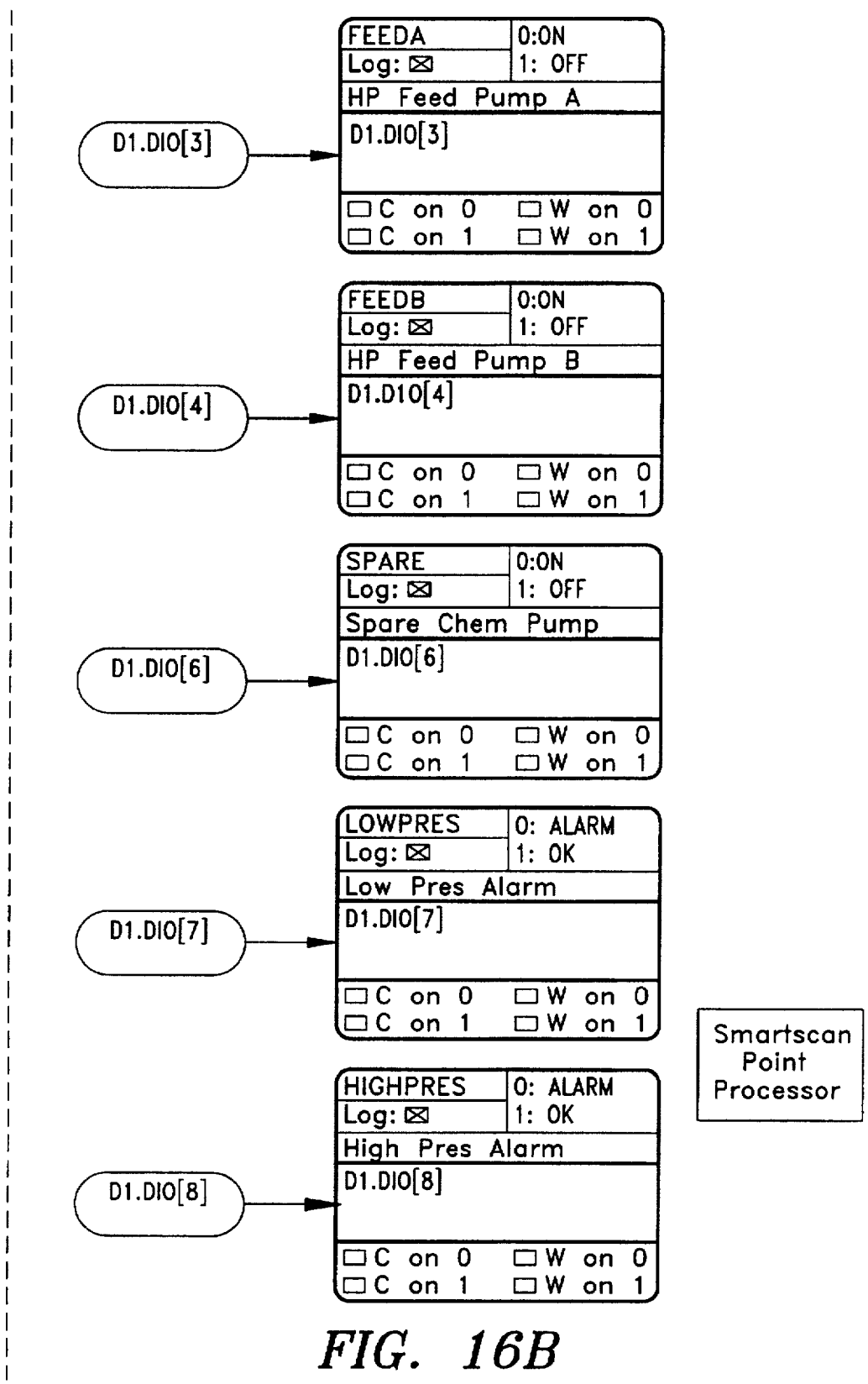
Figure 17:
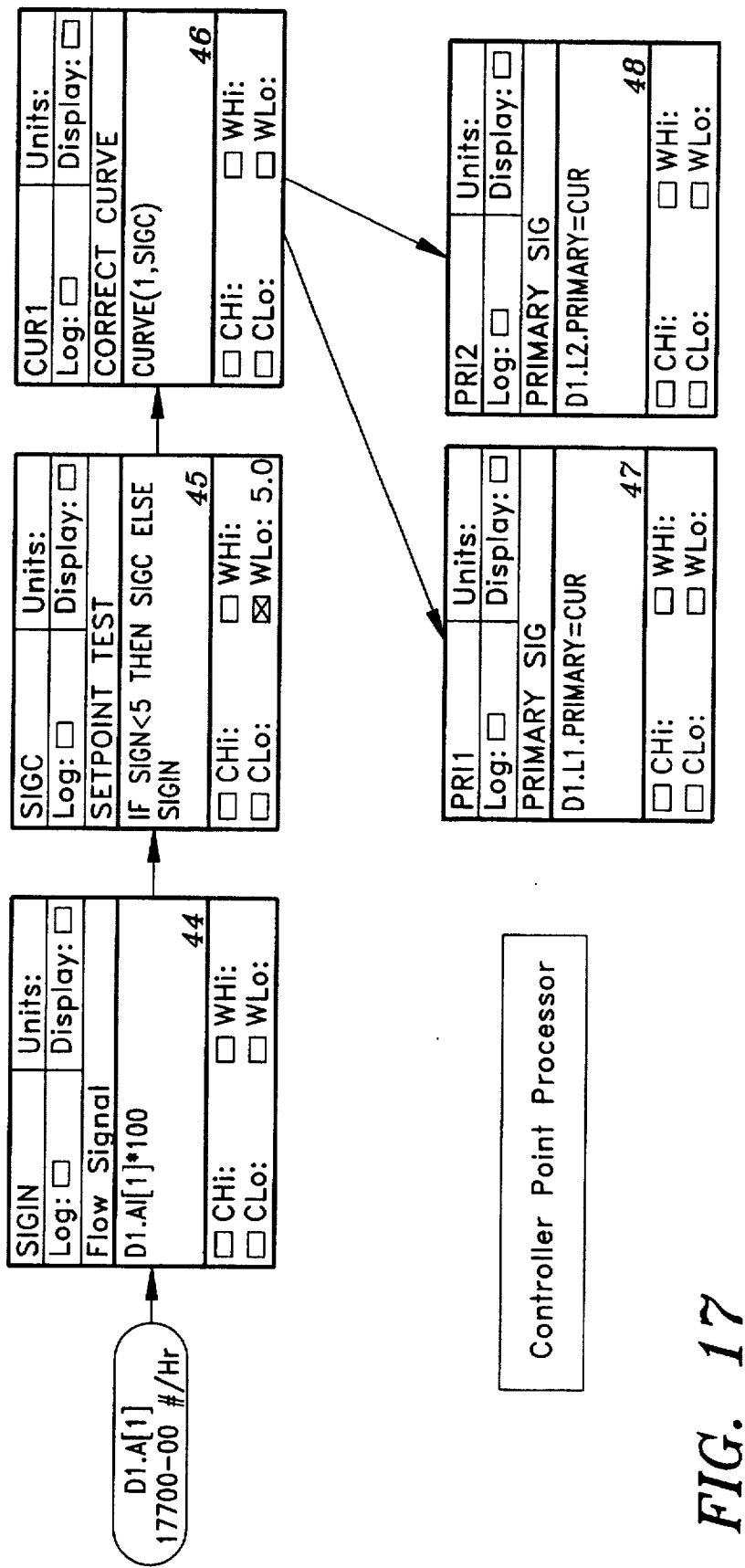
Figure 18A:
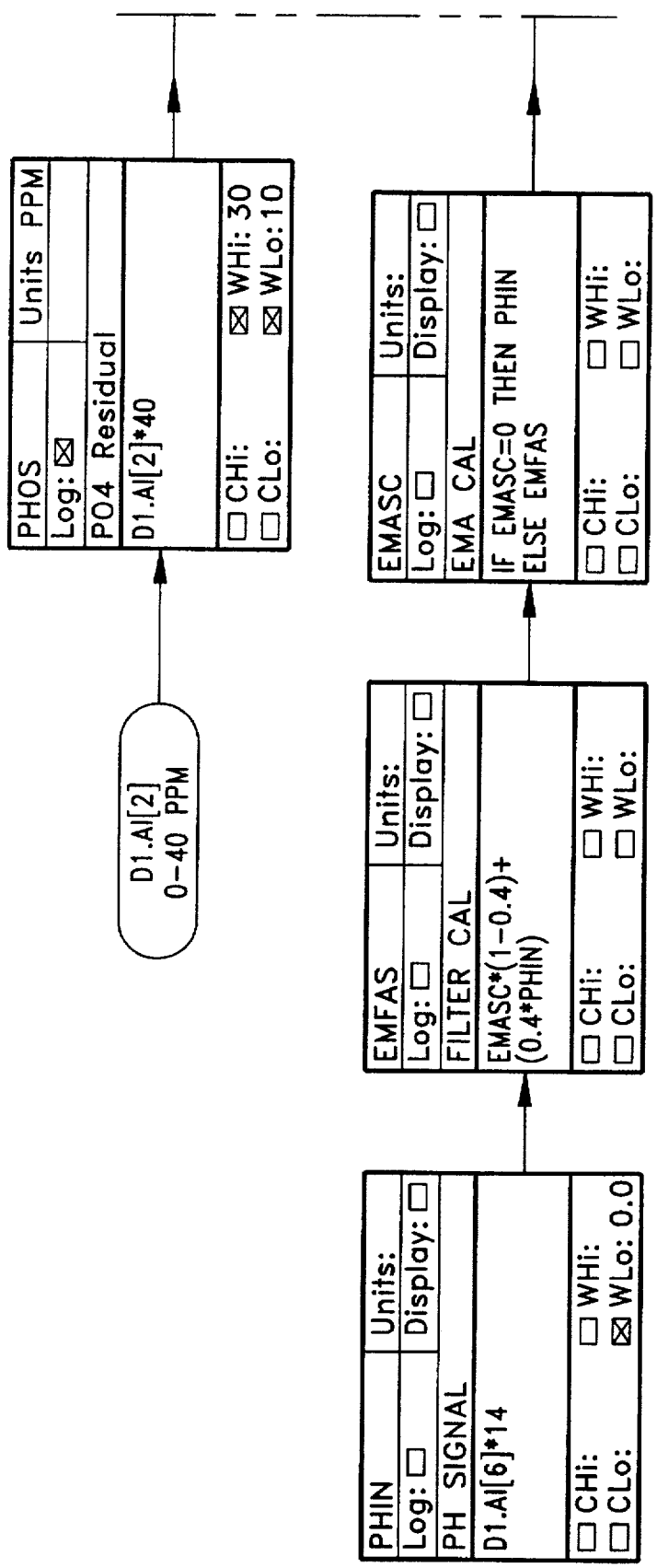
Figure 18B:
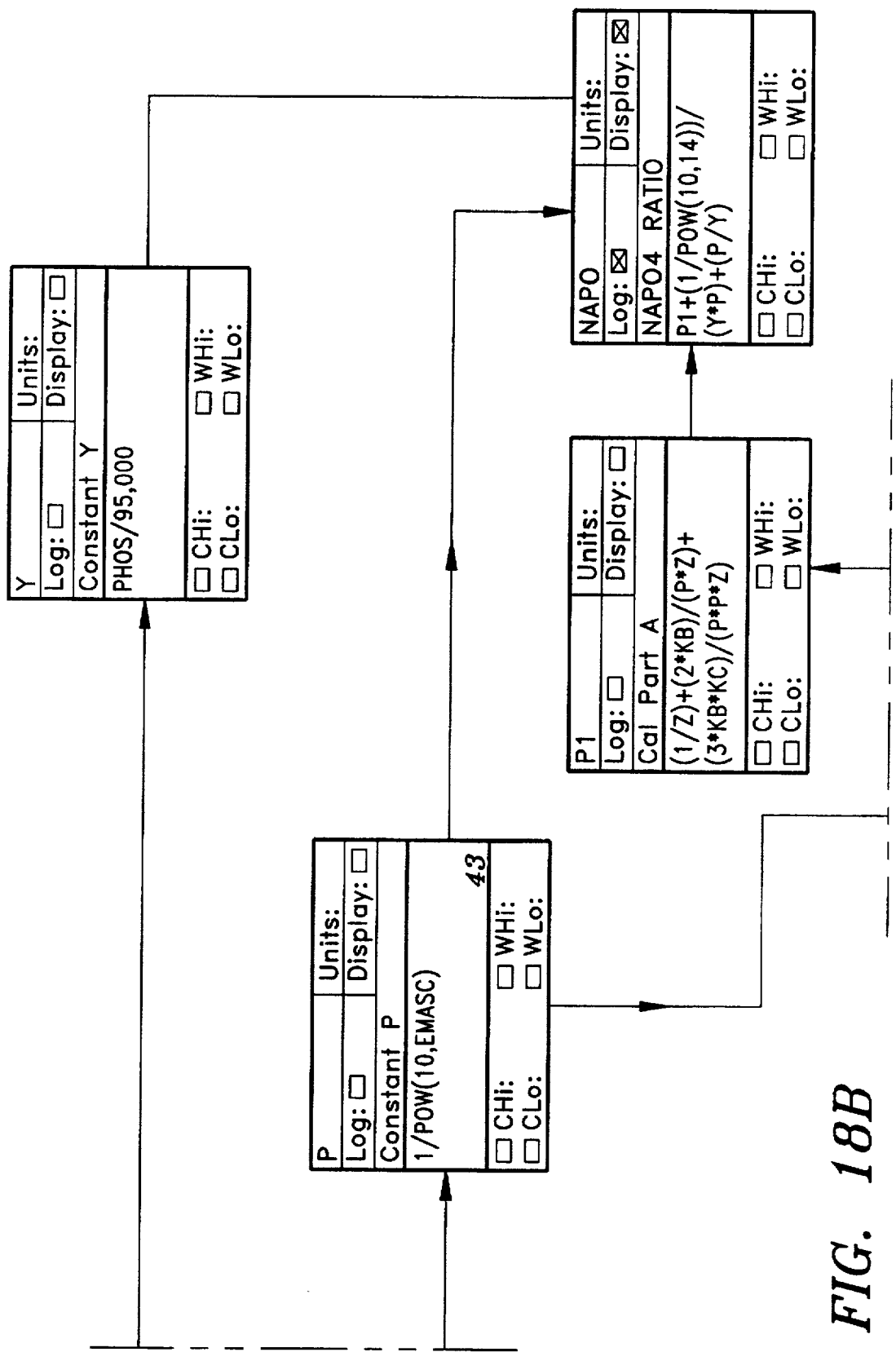
Figure 18C:
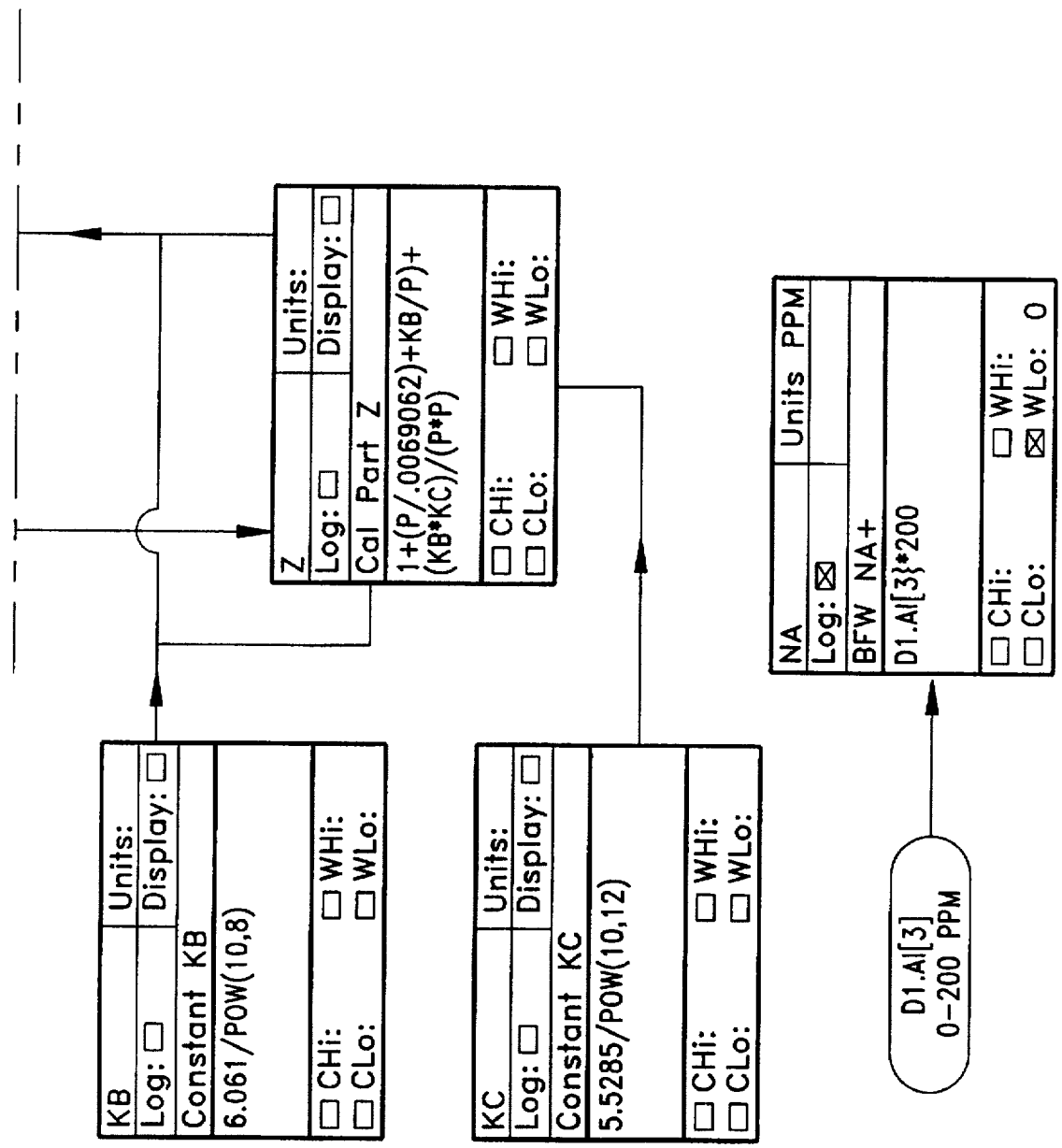

The system 220 basically comprises a first chemical feedstream 230A, a second chemical feedstream 230B, a control means 232 and an input means 240. The first chemical feedstream 230A and the second chemical feedstream 230B are each connected to the feedwater line 224. The first chemical feedstream 230A is arranged to deliver a first fluid treatment material or chemical, e.g., a sodium phosphate mixture having a particular sodium-to-phosphate ratio and a known phosphate concentration, to the water in the boiler 222. Similarly, the second chemical feedstream 230B is arranged to deliver a second fluid treatment material or chemical, e.g., a sodium phosphate mixture having a particular sodium-to-phosphate ratio and a known phosphate concentration to the water in the boiler 222. It is important to note at this juncture that the sodium-to-phosphate ratio in the first chemical feedstream 230A must be different from the sodium-to-phosphate ratio in the second chemical feedstream 230B while the respective known phosphate concentrations in the feedstreams can, in certain circumstances, be identical. The particular sodium-to-phosphate ratio (Na/PO$_4$) determines a particular pH for that fluid treatment material. Where the known phosphate concentration (PO$_4$) in both feedstreams is identical, then the different sodium concentrations (Na) in each feedstream determine the pH (high or low) of each fluid treatment material. The importance of the pH is that the pH of the boiler water, at a fixed phosphate concentration, is indicative of the sodium concentration in the boiler water. Thus, monitoring the pH of the boiler water provides an effective method of monitoring the sodium-to-phosphate ratio of the boiler water and then in determining which of the two feedstream sodium phosphate mixtures is to be fed to the boiler water to adjust the sodium-to-phosphate ratio of the boiler water, as will be described below. As shown in FIG. 13, by fixing the amount of phosphate in the boiler 222, varying the amount of sodium permits the sodium-to-phosphate ratio of the boiler water to be controlled.

Each feedstream 230A and 230B includes an electrically driven pump 234A and 234B which are coupled to the outlet of respective chemical feed tanks 236A and 236B, via respective draw down assemblies 238A and 238B. The chemical feed tanks 236A and 236B contain high-pH or low-pH sodium phosphate fluid treatment materials, respectively. The draw down assemblies 238A and 238B act as accumulators for enabling precise control of the pumps 234A and 234B by the control means 232.

The control means 232 is arranged to precisely control the two chemical feedstreams 230A and 230B by controlling the operation of the pumps 234A and 234B in order to achieve and maintain a predetermined desired sodium-to-phosphate ratio in the boiler water while maintaining a predetermined fixed phosphate concentration (PO$_4$ setpoint) in the boiler water. In particular, in response to the measurement of the boiler water pH provided by way of input means 240, the control means 232 adjusts the boiler water sodium-to-phosphate ratio by selecting one of the two feedstreams 230A or 230B to pump the appropriate sodium phosphate fluid treatment material while ensuring that the selected feedstream 230A or 230B pumps at a rate proportional to the blowdown flow 226 in order to maintain the fixed phosphate concentration.

The control means 232 basically comprises a computer-based control unit 242 such as that sold by Betz Laboratories, Inc. under the mark SMARTSCAN Plus and associated software/firmware 244 and a monitor/keyboard 246. The ON/OFF control system software 248 and SMARTSCAN Plus software 244 for effecting the operation of the control means 232 is set forth in FIGS. 14A, 14B, 14C, 14D, 15A,15B, 16A, 16B, 17, 18A, 18B, and 18C. The control means 232 also includes a feed pump controller 250 and the associated draw down assemblies 238A and 238B.

The feed pump controller 250 and the associated draw down assemblies 238A and 238B are constructed in accordance with the teachings of U.S. Pat. No. 4,897,797, assigned to the same assignee as this invention, namely Betz Laboratories, Inc., and whose disclosure is incorporated by reference herein.

As will be discussed in detail below, the ON/OFF control system software 248 evaluates the boiler water pH and compares that value to the pH setpoint that is entered into the computer 242 via the keyboard 246 by the operator. If the pH is above or below the pH setpoint, the ON/OFF control system software 248, via the computer 242 software/firmware, will command the feed pump controller 250 to drive the appropriate pump 234A or 234B to correctly feed the precise amount of chemicals that will achieve and maintain the desired phosphate concentration and the desired sodium-to-phosphate ratio.

The input means 240 basically comprises a blowdown flowmeter 252, a pH meter 254 and an optional phosphate analyzer 256. The blowdown flowmeter 252 measures the blowdown rate of the boiler 222 and provides a corresponding electrical signal on line 258 directly to the feed pump controller 250. As will be described later, the feed pump controller 250 uses this signal to ensure that whichever feedstream 230A or 230B is delivering its respective chemical mixture to the boiler 222, the chemical mixture feed is in proportion to the blowdown flow 226. In particular, the ON/OFF control system software 248 implements this proportion by the following equations:

Lo_Na_flow=PO4_setpoint*(BD_flow)/(Lo_PO4_conc)  (Equation #11)

Hi_Na_flow=PO4_setpoint*(BD_flow)/(Hi_PO4_conc)  (Equation #12)

where,

Hi_Na_flow: pump 234A pumping rate;

Lo_Na_flow: pump 234B pumping rate;

PO4_setpoint: predetermined fixed phosphate concentration

BD_flow: current blowdown flow measurement or exponential moving average of past n flow values;

Hi_PO4_conc: known phosphate concentration in tank 236A;

Lo_PO4_conc: known phosphate concentration in tank 236B;

The pH meter 254 monitors the pH of the blowdown flow 226 and provides a corresponding electrical signal on line 262 to the computer 242 for processing by the ON/OFF control system software 248. As is also well known, the pH of the blowdown flow 226 is indicative of the boiler water pH.

A cooling coil 264 is disposed between the blowdown flow 226 and the pH meter 254, as well as the optional phosphate analyzer 256 (if used), to protect these apparatus from damage due to the high temperature of the blowdown flow 226.

Control in this ON/OFF control system 220 resides in two places. The first area of control is by way of a maintenance means that maintains a fixed concentration of a chemical, e.g., phosphate, in the boiler water. In particular, the maintenance means for maintaining a fixed phosphate concentration in the boiler water comprises the feed pump controller 250, the two feedstreams 230A and 230B and the blowdown flowmeter 252. Since the phosphate concentration in each chemical feed tank 236A and 236B is known and the predetermined fixed phosphate concentration (PO$_4$ setpoint) has been entered into the computer 242 by the operator, the feed pump controller 250 uses the signal 258 to control the pumps 234A and 234B so that a precise amount of phosphate is delivered to the boiler water to feed the amount of phosphate needed to maintain the phosphate setpoint in steady state, in accordance with the previously discussed algorithm. In accordance with one preferred aspect of this invention, the ON/OFF control system 220 operates to ensure equal usage of tanks 236A and 236B, i.e., an even distribution of tank amount is used to avoid emptying one tank faster than the other.

The second area of control is through the switching between high-pH and low-pH sodium phosphate mixtures of the first chemical feedstream 230A and the second chemical feedstream 230B. This action is conducted by the control means 232. In particular, the ON/OFF control system software 246 may use, but is not required to use, an exponential moving average (EMA) of the pH (@25° C.) to minimize electronic noise from the pH meter 254 in providing the boiler water pH value. A pH adjustment is made at predetermined intervals, e.g., every 30 minutes. If the EMA pH value is above the pH setpoint, as determined by a comparator means in the ON/OFF control system software 248, the software 248 commands the feed pump controller 250, via the computer 242, to control the pump 234B to feed the low-pH sodium phosphate mixture in the second feedstream 230B at the proportioned rate (Equation #11) while turning off the other pump 234A in the first chemical feedstream 230A, thereby driving the boiler water pH value down to the pH setpoint. If the EMA pH value is below or equal to the pH setpoint as determined by the same comparator means in the ON/OFF control system software 248, software 248 commands the feed pump controller 250, via the computer 242, to control the pump 234A to feed the high-pH sodium phosphate mixture in the first feedstream 230A at the proportioned rate (Equation #12) while turning off the other pump 234B in the second chemical feedstream 230B, thereby driving the boiler water pH value up to the pH setpoint. In either situation, whichever feedstream is delivering its particular sodium phosphate mixture, the feed pump controller 250 maintains the fixed phosphate concentration in the boiler water by ratioing the active feedstream 230A or 230B to the blowdown rate. This alternate "on" and "off" feed control brings the boiler water sodium-to-phosphate ratio to the desired sodium-to-phosphate ratio at the predetermined fixed phosphate concentration and maintains that ratio at that phosphate concentration. In particular, the ON/OFF control system software 248 implements this switching by the following commands:

IF(pH >pH_setpoint) THEN
    Lo_Na_flow=PO4_setpoint * (BD_ flow)/(Lo_PO4_conc)
    Hi_Na_flow=0
ELSE
    Lo_Na_flow=0
    Hi_Na_flow=PO4_setpoint * (BD_ flow)/(Hi_PO4_conc)
where,
    pH: current pH value of boiler water or exponential weighted moving average of n past pH values;
    pH_setpoint: pH setpoint Should the first chemical feedstream 230A and the second feedstream 230B ever be utilized simultaneously so that both are delivering their respective sodium phosphate mixtures to the boiler water, rather than in alternation as in the ON/OFF control system 220, then the sum of the feedstream rates (Hi_Na_flow+Lo_Na_flow) would have to be in proportion to the blowdown flow 226 in order to maintain a fixed amount of phosphate in the boiler water.

The measurement of the blowdown pH can be a single measurement or can be the average pH value of a plurality of pH measurements.

In the ON/OFF control mode, it is assumed that the blowdown flow rate accurately maps the changes in boiler phosphate concentrations. It is possible that the expected and actual phosphate concentrations can start to diverge due to calibration problems, pump leaks, or actual leaks in the boiler. In that case, some means of monitoring the concentration and informing the operator that action to correct the boiler phosphate mass imbalance is desirable. One exemplary method of detecting the mass imbalance entails use of a phosphate analyzer 256. To that end, the analyzer 256 monitors the phosphate concentration in the boiler water and provides an electrical signal on line 260 to the feed pump controller 250 which, in turn, provides this electrical signal to the computer 242. The computer 242 provides the phosphate concentration to the ON/OFF control system software 248. The ON/OFF control system software 248 calculates the statistical variation in the desired phosphate concentration over time and alerts the operator to a boiler water phosphate mass imbalance. As an alternative to using the phosphate analyzer 256, the blowdown phosphate concentration could be manually measured and the measured phosphate concentration can be entered into the computer 242 at various time intervals.

Without further elaboration, the foregoing will so fully illustrate our invention that others may, by applying current or future knowledge, readily adopt the same for use under various conditions of service.

APPENDIX A

```
/* macc4.h: external interface for the macc4.c module */
/* May 29, 1994: added nh3, lastnh3, and b4lastnh3 to support ammonia
    correction to the pH -- JCG */ include <float.h>  /* uses only FLT_MAX */ define E_ENGINEERING_UNITS 1   /* 0=research units, 1=engineering units*/
define E_NAN (-1.0e37)         /* Not a number */
# define E_MINMINPO4 (1.0e-3/94.97)  /* 1   ppm in moles/kg */
# define E_MAXMAXPO4 (1.0e-1/94.97)  /* 100 ppm in moles/kg */
# define E_MINMINNAPO4RATIO 2.2
# define E_MAXMAXNAPO4RATIO 2.8
# define E_MAXBISECTIONS 100     /* aprox. 1 part in 1.26765e+30 */
# define E_NV 4    /* number of vertexes in feasable region, V */
define E_NW 4    /* number of vertexes in target region, W */ typedef enum e_logical { E_FALSE=0, E_TRUE=1 }    E_LOGICAL;

typedef struct e_vector { double po4; double na; } E_VECTOR;

typedef enum e_initstatus {     /* e_init() errors/alarms */
    E_INITOK=0,
    E_MISSING_T,
    E_MISSING_FAMIN,
    E_MISSING_FAMAX,
    E_MISSING_FADEF,
    E_MISSING_PO4A,
    E_MISSING_RATIOA,
    E_MISSING_FBMIN,
    E_MISSING_FBMAX,
    E_MISSING_FBDEF,
    E_MISSING_PO4B,
    E_MISSING_RATIOB,
    E_MISSING_PO4,
    E_MISSING_PH,
    E_MISSING_M,
    E_MISSING_BDTEMP,
    E_MISSING_PO4SETPOINT,
    E_MISSING_MINPO4,
    E_MISSING_MAXPO4,
    E_MISSING_RATIOSETPOINT,
    E_BDMAX_LT_BDMIN,
    E_NALEAKMAX_LT_NALEAKMIN,
```

```
    E_FAMAX_LE_FAMIN,
    E_FBMAX_LE_FBMIN,
    E_MINPO4_LT_MINMINPO4,
    E_MAXPO4_GT_MAXMAXPO4,
    E_PO4SETPOINT_LT_MINPO4,
    E_PO4SETPOINT_GT_MAXPO4,
    E_PO4A_LT_ZERO,
    E_PO4B_LT_ZERO,
    E_MINRATIO_LT_MINMINRATIO,
    E_MAXRATIO_GT_MAXMAXRATIO,
    E_RATIO_LT_MINRATIO,
    E_RATIO_GT_MAXRATIO,
    E_RATIOA_EQ_RATIOB,
    E_MISSING_SPGA,
    E_MISSING_SPGB,
}
E_INITSTATUS;

typedef enum e_updatestatus {       /* e_update() errors/alarms */
    E_UPDATEOK=0,
    E_INDETERMINATE=1,
    E_BOX_UNREACHABLE=2,
    E_OUTOFBOX_TOOLONG=4,
    E_POINT_UNREACHABLE=8,
    E_BOX_UNMAINTAINABLE=16,
    E_POINT_UNMAINTAINABLE=32,
    E_SAMPLEINTERVAL_TOOLONG=64,
    E_NOTUPDATED=128,
    E_INCONSISTENT_PO4=256,
    E_INCONSISTENT_PH=512
} E_UPDATESTATUS;

typedef struct e_boiler { /* public: */
    double t;                   /* time since start of run         */
    double famin,       /* pump a =>   mininum feed rate           */
           famax,       /*             maximum feed rate           */
           fadef,       /*             default (initial) feed rate */
           po4a,        /*             total PO4 (as ortho-PO4) concentration */
           ratioa,      /*             Na/PO4 ratio                */
           spga;        /*             specific gravity            */
    double fbmin,       /* pump b =>   mininum feed rate           */
           fbmax,       /*             maximum feed rate           */
           fbdef,       /*             default (initial) feed rate */
           po4b,        /*             total PO4 (as ortho-PO4) concentration */
           ratiob,      /*             Na/PO4 ratio                */
```

```
        spgb;                   /*              specific gravity */
    double m;                   /* boiler water mass */
    double bdtemp;              /* boiler blowdown temperature */
    double po4,                 /* boiler blowdown po4 => concentration */
         dpo4,                  /*                        variability */
         po4setpoint,           /*                        setpoint */
         minpo4,                /*                        lower control limit */
         maxpo4;                /*                        upper control limit */
    double nh3;                 /* boiler blowdown ammonia concentration */
    double ph,                  /* boiler blowdown pH => at temperature=bdtemp */
         dph,                   /*                       variability */
         phsetpoint,            /*                       setpoint (nh3=0.0;bdtemp=25C)*/
         dphsetpoint;           /*                       1/2 setpoint control range */
                                /* (control limits = phsetpoint +/- dphsetpoint)*/
    double napo4ratio,          /* alternative to phsetpoint */
         minnapo4ratio,         /* alternative to phsetpoint-dphsetpoint */
         maxnapo4ratio;         /* alternative to phsetpoint+dphsetpoint */
    double max_sample_interval; /* if time between samples is longer than*/
                                /* this, an updatestatus code is flagged */
    double max_outofbox_adjustment; /* if we cannot get into control ranges on */
                                /* pH and PO4 within this time, an */
                                /* updatestatus code is flagged */
    double max_relative_error;  /* largest allowed variation in estimated */
/* steady-state concentrations induced by the given variabilities, dpH and */
/* dPO4 before an E_INDETERMINATE status is flagged */
    double beps,                /* bisection (root finding) epsilon */
         bdmin,                 /* lower bound for blowdown bisection */
         bdmax,                 /* upper bound for blowdown bisection*/
         naleakmin,             /* lower bound for Na leak bisection */
         naleakmax;             /* upper bound for Na leak bisection */
/* (final errors on root finding due to truncation errors will be */
/*  beps*(|bdmax| + |bdmin|) and beps*(|naleakmin|+|naleakmax|) */
    double fdt;                 /* feed delta time (due to hardware truncation): */
/*                                 minimum time interval between pump changes */
?
/* private: */
    double lastt, lastbdtemp, lastpo4, lastnh3, lastph; /*last inputs... */
    double b4lastt,b4lastbdtemp,b4lastpo4,b4lastnh3, b4lastph;/* & before last */
    double bd, l;                /* blowdown, leak estimates */
    double lastbd, lastl;        /* prev blowdown, leak estimates */
    double dt[2], fb[3], fa[3];  /* current feed program */
    double lastdt[2], lastfb[3], lastfa[3]; /* previous feed program */
    E_VECTOR vV[E_NV+1], vW[E_NW+1]; /* pumpable, target regions */
    E_VECTOR vlastV[E_NV+1], vlastW[E_NW+1]; /* last pumpable, target regions */
    E_VECTOR vF[3];              /* steady-state concentrations of the feed program */
    E_VECTOR vlastF[3]; /* last steady-state concentrations of the feed program*/
```

55

```
    E_UPDATESTATUS updatestatus;       /* identifier for e_update() status*/
    E_UPDATESTATUS lastupdatestatus;   /* previous updatestatus */
    E_INITSTATUS initstatus;           /* identifier for e_init() errors*/
    E_LOGICAL undoable;                /* can last e_update be undone ? */
} E_BOILER;

const E_BOILER *e_undefined_boiler(void);
E_INITSTATUS e_init(E_BOILER *blr);
double e_afeed(E_BOILER *blr);
double e_bfeed(E_BOILER *blr);
E_UPDATESTATUS e_update(E_BOILER *blr);
E_LOGICAL e_undo(E_BOILER *blr);
double e_hmp2po4(double hmp);

double e_po4model(E_BOILER *blr);
double e_phmodel(E_BOILER *blr);
double e_nasetpoint(E_BOILER *blr);
double e_congruencyratio(E_BOILER *blr);
double e_fixNAN(double number, double forNAN);
```

```
/* macc4.c: module for model based coordinated phosphate/ph control */
/*
    April  4, 1994 : added lines near the end of e_update() to force
    feed rates within specified pumping lower and upper bounds.
    Roundoff error sometimes resulted in pump rates of -1.0e-10
    rather than 0.0; such negative numbers can often spook equipment
    which is sometimes set up to ignore such "meaningless" values - JCG April 10, 1994: fixed a parentheses error near the bottom of
    e_init(). Error was harmless for most usages but not for
    the way I was using e_init() in MACC4SSP. Error was on
    line the began blr->bd = fixNAN(...).
    Also removed two local variables that were never used in
    e_update() - JCG April 17th- fixed default blowdown calculation at bottom for e_init()
    - JCG same line as bugfix above.

May  2, 1994 - set updatestatus field to E_UPDATEOK in e_init()
    (so it is in a well defined state after each e_init() call).

May 29, 1994 - added support for an ammonia correction to the
    pH as per Scot Boyette's request.

June 3, 1994 - added an e_congruencyratio() exported function
    to support callers who want to see the Na:PO4 ratio of the
    entered pH, PO4, NH3, and temperature last entered.
*/
#include "macc4.h"
#include <math.h>

/* These macros provide for on-the-fly units conversion from
    engineering units to the research units used in MACC4's internal
    calculations. Rather than blr->famin we write FAMIN(blr), and these
    macros guarantee that the resulting value will be in research units,
    even though the value stored in blr->famin is in engineering units.
*/ define E_LITERS_PER_GALLON (3.785)
define E_MW_PO4 (94.97)
# define E_MW_NH3 (17.0)
# define E_ZERO_K_IN_F (-459.67)
```

57

```
# define E_GPD_TO_KGPERHR(gpd,spg) ((E_LITERS_PER_GALLON/24.0)*(spg)*(gpd))
# define E_PPM_TO_MOLESPERKG(ppm,mw) ((ppm)*1.0e-3/(mw))
# define E_MOLESPERKG_TO_PPM(mpk,mw) ((mpk)*1.0e+3*(mw))
# define E_PERCENT_TO_MOLESPERKG(percent,mw) ((percent)*1.0e+1/(mw))
# define E_LB_TO_KG(lb) ((lb)*0.45359)
# define E_KG_TO_LB(kg) ((kg)/0.45359)
# define E_F2KELVIN(f) ((5.0/9.0)*((f) - E_ZERO_K_IN_F))
# define K_DEFAULT_TEMP 298.15   /*room temperature in degrees K */
# define K_DEFAULT_NH3 0.0       /*for Na:PO4 ratio setpoints, in moles/kg */
# define K_DEFAULT_RHO 0.997047 /*room temperature density of saturated H2O*/
?
#if E_ENGINEERING_UNITS    /* this compilation switch is set in macc4.h */

/* Conversions require to obtain MACC4's internal units: */
/* flows:            gallons/day       ==> kg/hr       */
/* PO4 boiler conc:  ppm as ortho PO4  ==> moles/kg    */
/* PO4 fwws conc:    % as ortho PO4    ==> moles/kg    */
/* Boiler mass:      lbs               ==> kgs         */ define FAMIN(blr) E_GPD_TO_KGPERHR((blr)->famin,(blr)->spga)
define FAMAX(blr) E_GPD_TO_KGPERHR((blr)->famax,(blr)->spga)
# define FADEF(blr) E_GPD_TO_KGPERHR((blr)->fadef,(blr)->spga)
# define PO4A(blr)  E_PERCENT_TO_MOLESPERKG((blr)->po4a, E_MW_PO4)
# define NAA(blr)   ((blr)->ratioa*PO4A(blr))
# define FBMIN(blr) E_GPD_TO_KGPERHR((blr)->fbmin,(blr)->spgb)
# define FBMAX(blr) E_GPD_TO_KGPERHR((blr)->fbmax,(blr)->spgb)
# define FBDEF(blr) E_GPD_TO_KGPERHR((blr)->fbdef,(blr)->spgb)
# define PO4B(blr)  E_PERCENT_TO_MOLESPERKG((blr)->po4b, E_MW_PO4)
# define NAB(blr)   ((blr)->ratiob*PO4B(blr))
# define FDT(blr)   ((blr)->fdt)
# define USERPO4(po4) E_MOLESPERKG_TO_PPM(po4, E_MW_PO4)
# define PO4(blr) E_PPM_TO_MOLESPERKG((blr)->po4, E_MW_PO4)
# define LASTPO4(blr) E_PPM_TO_MOLESPERKG((blr)->lastpo4, E_MW_PO4)
# define DPO4(blr) E_PPM_TO_MOLESPERKG((blr)->dpo4, E_MW_PO4)
# define MINPO4(blr) E_PPM_TO_MOLESPERKG((blr)->minpo4, E_MW_PO4)
# define MAXPO4(blr) E_PPM_TO_MOLESPERKG((blr)->maxpo4, E_MW_PO4)
# define PO4SETPOINT(blr) E_PPM_TO_MOLESPERKG((blr)->po4setpoint, E_MW_PO4)
# define NH3(blr) \
  E_PPM_TO_MOLESPERKG(e_fixNAN((blr)->nh3,K_DEFAULT_NH3), E_MW_NH3)
# define LASTNH3(blr) \
  E_PPM_TO_MOLESPERKG(e_fixNAN((blr)->lastnh3,K_DEFAULT_NH3), E_MW_NH3)
# define LASTPH(blr) ((blr)->lastph)
# define PH(blr) ((blr)->ph)
# define DPH(blr) ((blr)->dph)
```

```
#  define PHSETPOINT(blr) ((blr)->phsetpoint)
#  define DPHSETPOINT(blr) ((blr)->dphsetpoint)
#  define LASTT(blr) ((blr)->lastt)
#  define T(blr) ((blr)->t)
#  define M(blr) E_LB_TO_KG((blr)->m)
#  define BDTEMP(blr) E_F2KELVIN(blr->bdtemp)
#  define LASTBDTEMP(blr) E_F2KELVIN(blr->lastbdtemp)
# define MAX_SAMPLE_INTERVAL(blr) ((blr)->max_sample_interval)
# define MAX_OUTOFBOX_ADJUSTMENT(blr) ((blr)->max_outofbox_adjustment)
#  define BEPS(blr) ((blr)->beps)
#  define NALEAKMIN(blr) ((blr)->naleakmin)
#  define BDMIN(blr) E_LB_TO_KG((blr)->bdmin)
#  define NALEAKMAX(blr) ((blr)->naleakmax)
#  define USERBD(bd) E_KG_TO_LB(bd)
#  define BDMAX(blr) E_LB_TO_KG((blr)->bdmax)
#  define MAX_RELATIVE_ERROR(blr) (((blr)->max_relative_error)/100.0)
#  define BD(blr) E_LB_TO_KG((blr)->bd)
#  define L(blr) ((blr)->l)
#  define DT(blr,n) ((blr)->dt[n])
#  define FA(blr,n) E_GPD_TO_KGPERHR((blr)->fa[n], (blr)->spga)
#  define FB(blr,n) E_GPD_TO_KGPERHR((blr)->fb[n], (blr)->spgb)
#  define DEFAULT_DPO4 0.5
#  define DEFAULT_DPH  0.05
#  define DEFAULT_DPHSETPOINT  0.025
# define DEFAULT_MAX_OUTOFBOX_ADJUSTMENT (24.0*7.0) /* seven days */
# define DEFAULT_MAX_RELATIVE_ERROR 20.0 /*20% error allowed by default*/
#  define DEFAULT_MAX_SAMPLE_INTERVAL (24.0*7.0)
define DEFAULT_BEPS 1.0e-12 else   /* research units */
define FAMIN(blr) ((blr)->famin)
#  define FAMAX(blr) ((blr)->famax)
#  define FADEF(blr) ((blr)->fadef)
#  define PO4A(blr) ((blr)->po4a)
#  define NAA(blr) ((blr)->ratioa*PO4A(blr))
#  define FBMIN(blr) ((blr)->fbmin)
#  define FBMAX(blr) ((blr)->fbmax)
#  define FBDEF(blr) ((blr)->fbdef)
#  define PO4B(blr) ((blr)->po4b)
#  define NAB(blr) ((blr)->ratiob*PO4B(blr))
#  define FDT(blr) ((blr)->fdt)
#  define LASTPO4(blr) ((blr)->lastpo4)
#  define USERPO4(po4) (po4)
#  define PO4(blr) ((blr)->po4)
#  define DPO4(blr) ((blr)->dpo4)
```

59

```
# define MINPO4(blr)    ((blr)->minpo4)
# define MAXPO4(blr)    ((blr)->maxpo4)
# define PO4SETPOINT(blr)    ((blr)->po4setpoint)
# define LASTNH3(blr)    (e_fixNAN((blr)->lastnh3, K_DEFAULT_NH3))
# define NH3(blr)    (e_fixNAN((blr)->nh3, K_DEFAULT_NH3))
# define LASTPH(blr)    ((blr)->lastph)
# define PH(blr)    ((blr)->ph)
# define DPH(blr)    ((blr)->dph)
# define PHSETPOINT(blr)    ((blr)->phsetpoint)
# define DPHSETPOINT(blr)    ((blr)->dphsetpoint)
# define LASTT(blr)    ((blr)->lastt)
# define T(blr)    ((blr)->t)
# define M(blr)    ((blr)->m)
# define BDTEMP(blr)    (273.15 + (blr)->bdtemp)
# define LASTBDTEMP(blr)    (273.15+(blr)->lastbdtemp)
# define BLRTEMP(blr)    (273.15+(blr)->blrtemp)
# define MAX_SAMPLE_INTERVAL(blr)    ((blr)->max_sample_interval)
# define MAX_OUTOFBOX_ADJUSTMENT(blr)    ((blr)->max_outofbox_adjustment)
# define BEPS(blr)    ((blr)->beps)
# define NALEAKMIN(blr)    ((blr)->naleakmin)
# define USERBD(bd)    (bd)
# define BDMIN(blr)    ((blr)->bdmin)
# define NALEAKMAX(blr)    ((blr)->naleakmax)
# define BDMAX(blr)    ((blr)->bdmax)
# define MAX_RELATIVE_ERROR(blr)    ((blr)->max_relative_error)
# define BD(blr)    ((blr)->bd)
# define L(blr)    ((blr)->l)
# define DT(blr,n)    ((blr)->dt[n])
# define FA(blr,n)    ((blr)->fa[n])
# define FB(blr,n)    ((blr)->fb[n])
# define DEFAULT_DPO4 E_PPM_TO_MOLESPERKG(0.5,E_MW_PO4)
# define DEFAULT_DPH    0.05
# define DEFAULT_DPHSETPOINT    0.025
# define DEFAULT_MAX_OUTOFBOX_ADJUSTMENT (24.0*7.0) /* seven days */
# define DEFAULT_MAX_RELATIVE_ERROR 0.2 /*20% error allowed by default*/
# define DEFAULT_MAX_SAMPLE_INTERVAL (24.0*7.0)
define DEFAULT_BEPS 1.0e-12
endif define ROUNDED_DT(blr,n) (e_round_down(DT(blr,n), FDT(blr)))

?
/* Misc. Functions */ double e_round_down(double x, double dx) { /* round x down to multiple of dx */
    return ( x - ((dx <= 0.0) ? 0.0 : fmod(x,dx)));
```

```
}
double e_min(double x, double y) {        /* minimum of 2 numbers */
    return((x < y) ? x : y);
}
double e_max(double x, double y) {        /* maximum of 2 numbers */
    return((x > y) ? x : y);
} double e_forceinrange(double x, double low, double high) {/*force low<=x<=high*/
    if ( x <= low)
        return(low);
    else if ( x >= high)
        return(high);
    else
        return(x);
}

/* use fabs(x) for |x|, log(x) for ln(x) */

/* Basic Vector Operations */
#define VBUF 100
E_VECTOR *e_vec(double po4, double na) {  /* convert 2 components to vec*/
    static E_VECTOR v[VBUF]={{0.0,0.0}};/*uses circular buffer;callers must not*/
    static int ibuf = VBUF-1;    /* depend upon this memory since is will be */
    ibuf = (ibuf+1) % VBUF;      /* reused every VBUFth call */
    v[ibuf].po4 = po4;           /* (for example, expressions with more than */
    v[ibuf].na = na;             /* VBUF e_vec() calls will have problems)*/
    return(&v[ibuf]);            /* Approach needed to work around an MS-C bug*/
}                                /* when passing structures to/from functions*/ double e_dot(E_VECTOR *v1, E_VECTOR *v2) { /* inner (dot) product of 2 vecs*/
    return(v1->po4*v2->po4 + v1->na*v2->na);
} double e_norm(E_VECTOR *v) {              /* magnitude (norm) of vector */
    return(sqrt(e_dot(v,v)));
} double e_norm2(E_VECTOR *v) {    /* magnitude (norm) of vector, squared */
    return(e_dot(v,v));
}

/*e_sXv: multiply ("X") a scalar, s, times a vector, v */
E_VECTOR *e_sXv(double s, E_VECTOR *v) {
```

61

```
    return(e_vec(s*v->po4,s*v->na));
}

E_VECTOR *e_vDs(E_VECTOR *v, double s) {   /* divide a vector by a scalar */
    return(e_sXv(1.0/s, v));
}
/* e_vPv: add ("P") two vectors */
E_VECTOR *e_vPv(E_VECTOR *v1, E_VECTOR *v2)
{
    return(e_vec(v1->po4 + v2->po4,v1->na + v2->na));
}

/* e_vSv: Subtract ("S") two vectors (v1 - v2)*/

E_VECTOR *e_vSv(E_VECTOR *v1, E_VECTOR *v2) {
    return(e_vPv(v1, e_sXv(-1.0, v2)));
}
/* e_vEv: Are two vectors approximately equal, within machine precision ? */

E_LOGICAL e_vEv(E_VECTOR *v1, E_VECTOR *v2) {
    return ( (e_norm(e_vSv(v1,v2)) <= DBL_EPSILON*(e_norm(v1)+e_norm(v2))) ?
                    E_TRUE : E_FALSE);
}
/* Vector Functions */

E_VECTOR *e_rot90(E_VECTOR *v) {/*rotate vector counterclockwise 90 degrees */
    return(e_vec(- v->na, v->po4));
}

/* e_between: given three co-linear points, is <B> between <A> and <C> ? */

E_LOGICAL e_between(E_VECTOR *vA, E_VECTOR *vB, E_VECTOR *vC) {
    return( (e_norm(e_vSv(vA,vB)) <= e_norm(e_vSv(vA,vC)) &&
             e_norm(e_vSv(vB,vC)) <= e_norm(e_vSv(vA,vC))) ? E_TRUE : E_FALSE);
}

/* e_decompose: decomposes a given vector into the given "coordinate system".
    Specifically, computes alpha and beta such that:

<A>  =  <Origin>  +  alpha*<XX>  +  beta*<YY>.

Here <A>, <Origin>, <XX>, and <YY> are vectors, alpha and beta are scalars.
```

62

```
Note: <XX> and <YY> must be linearly independent and non-zero,
      or divide by 0 errors will occur (macc4 prevents
      such a possibility by various up front checks).
*/ void e_decompose(E_VECTOR *vA, E_VECTOR *vOrigin, E_VECTOR *vXX, E_VECTOR *vYY,
                 double *alpha, double *beta)

E_VECTOR *vx, *vu, *vuperpx, *vYYperpx;
    vx = e_vDs(vXX,e_norm(vXX));
    vu = e_vSv(vA,vOrigin);
    vuperpx = e_vSv(vu, e_sXv(e_dot(vu,vx), vx));
    vYYperpx = e_vSv(vYY, e_sXv(e_dot(vYY,vx),vx));
    *beta = e_dot(vuperpx,vYYperpx)/e_dot(vYYperpx,vYYperpx);
    *alpha = e_dot(vx, e_vSv(vu, e_sXv(*beta,vYY)))/e_norm(vXX);

/* Functions for ph to na Conversion */

/* db_rho: density of water along the saturation line ("psat") */
/* (included from CMS 2.0 module db2.c) */
/* Scott Boyette provided; original source Journal of Physical and
   Chemical Reference Data, Vol 10, No. 2, 1981 p 295. W. L. Marshal
   and E. U. Franck.
*/ double db_rho(double t)  { /* t in degrees K */
    static double a[] = {-0.735396, 0.015695, -1.153587E-5,
                         -8.157489E-8, 2.121698E-10, -1.590221E-13 };
    int i = sizeof(a)/sizeof(a[0]);
    double rho = a[--i];  /* compute "sum over i of a[i]*t**i" */ if (fabs(K_DEFAULT_TEMP-t) <= K_DEFAULT_TEMP*DBL_EPSILON)
                          /* to avoid "fit of a fit" errors */
        return(K_DEFAULT_RHO);  /* for special case of room temp values*/
                          /* use the exact value (as per S. Boyette)*/ do {
        rho *= t;
        rho += a[--i];
    } while (i > 0);

rho /= (1.0 + 0.003582*t);
    return(rho);
```

}

```
/* e_na: Back calculates an "equivalent na" in the boiler, using
    the charge balance equation and measured po4 and ph in the boiler.

po4, na concentrations are in moles/kg. Temperature in Kelvin. Activity is
        assumed 1.0 for simplicity (no ionic strength correction).

See CMS (Condensate Modelling System) 2.0 module db2.c for equilibrium
    constants and the algebraic expression used for the charge balance equation.

May 29, 1994: added nh3 parameter to account for ammonia
*/ double e_na(double po4, double ph, double t, double nh3) {
    double Ti  = 1.0/t;
    double rho = db_rho(t);
    double H   = pow(10.0, -ph)/rho;
    double K1  = pow(10.0, - (-3.900391 + 0.01216*t + 725.804792/t));
    double K2  = pow(10.0, - (-2.654013+0.01534*t+1579.171467/t));
    double K3  = pow(10.0, - (-3.399999E-3*t + 12.44871));
    double Kw  = pow (10.0,
        - 4.098 + Ti*(-3245.2 + Ti*(2.2362e5 - Ti*3.984e7)) +
              log10(rho)*(13.957 + Ti*(-1262.3 + Ti*8.5641e5)));
    double K1nh3 = pow(10.0, - (12.423779 + 6.202054E-4*t +
                                2188.435335/t - 4.325705*log10(t)));

return(Kw/H - H - nh3*(H/K1nh3)/(1.0 + H/K1nh3) +
          + po4*(K1/H + 2.0*(K1/H)*(K2/H) + 3.0*(K1/H)*(K2/H)*(K3/H))/
              (1.0 + (K1/H) + (K1/H)*(K2/H) + (K1/H)*(K2/H)*(K3/H)));
}

/*e_congruencyratio: exported congruency Na:PO4 ratio calculation */ double e_congruencyratio(E_BOILER *blr) {
    if (E_NAN == blr->po4 ||
        0.0 >= PO4(blr) ||
        E_NAN == blr->ph  )
      return(E_NAN);
    else
      return(e_na(PO4(blr),
                  PH(blr),
                  e_fixNAN(BDTEMP(blr), K_DEFAULT_TEMP),
```

```c
                    e_fixNAN(NH3(blr), K_DEFAULT_NH3)
            ) / PO4(blr)
        );
}
?
double e_napo4ratio(E_BOILER *blr) { /* napo4ratio setpoint for boiler */
    return ((blr->napo4ratio != E_NAN) ? (blr->napo4ratio) :
        (e_na(PO4SETPOINT(blr), PHSETPOINT(blr), K_DEFAULT_TEMP, K_DEFAULT_NH3)/
            PO4SETPOINT(blr)) );
}
double e_minnapo4ratio(E_BOILER *blr) { /*min napo4ratio setpoint for boiler */
    return ((blr->minnapo4ratio != E_NAN) ? (blr->minnapo4ratio) :
        e_max(E_MINMINNAPO4RATIO,
            e_na(PO4SETPOINT(blr),PHSETPOINT(blr)-DPHSETPOINT(blr),
                K_DEFAULT_TEMP, K_DEFAULT_NH3)
            / PO4SETPOINT(blr)) );
}
double e_maxnapo4ratio(E_BOILER *blr) { /*max napo4ratio setpoint for boiler */
    return ((blr->maxnapo4ratio != E_NAN) ? (blr->maxnapo4ratio) :
        e_min(E_MAXMAXNAPO4RATIO,
            e_na(PO4SETPOINT(blr),PHSETPOINT(blr)+DPHSETPOINT(blr),
                K_DEFAULT_TEMP,K_DEFAULT_NH3)
            / PO4SETPOINT(blr)) );
}

/* e_fixNAN: replace E_NAN's (not a number) with a given value */ double e_fixNAN(double number, double forNAN) {
    return (number == E_NAN ? forNAN : number);
}
?
/* Main Functions */

/* e_init: check that required constants of macc4 are properly specified*/
/* should be used in conjunction with e_undefined_boiler() as defined in
    macc4.h, e.g.:

# include "macc4.h"
    E_BOILER b1 = *e_undefined_boiler(); (sets all fields to E_NAN (undefined)
    b1.famin = famin;  b1.famax = ... etc. (define the fields)
        if (e_init(&b1) != E_INITOK)
            error();

*/
```

```
E_INITSTATUS e_init(E_BOILER *blr)
{
   blr->initstatus  = E_INITOK;    /* clear initstatus flag */
   blr->undoable    = E_FALSE;
   blr->updatestatus = E_UPDATEOK;

if      (blr->t     == E_NAN)  blr->initstatus = E_MISSING_T;
   else if (blr->famin == E_NAN) blr->initstatus = E_MISSING_FAMIN;
   else if (blr->famax == E_NAN) blr->initstatus = E_MISSING_FAMAX;
   else if (blr->fadef == E_NAN) blr->initstatus = E_MISSING_FADEF;
   else if (blr->po4a  == E_NAN) blr->initstatus = E_MISSING_PO4A;
   else if (blr->ratioa== E_NAN) blr->initstatus = E_MISSING_RATIOA;
   else if (blr->fbmin == E_NAN) blr->initstatus = E_MISSING_FBMIN;
   else if (blr->fbmax == E_NAN) blr->initstatus = E_MISSING_FBMAX;
   else if (blr->fbdef == E_NAN) blr->initstatus = E_MISSING_FBDEF;
   else if (blr->po4b  == E_NAN) blr->initstatus = E_MISSING_PO4B;
   else if (blr->ratiob== E_NAN) blr->initstatus = E_MISSING_RATIOB;
   else if (blr->po4   == E_NAN) blr->initstatus = E_MISSING_PO4;
   else if (blr->ph    == E_NAN) blr->initstatus = E_MISSING_PH;
   else if (blr->m     == E_NAN) blr->initstatus = E_MISSING_M;
   else if (blr->bdtemp== E_NAN) blr->initstatus = E_MISSING_BDTEMP;
   else if (blr->po4setpoint
                       == E_NAN) blr->initstatus = E_MISSING_PO4SETPOINT;
   else if (blr->minpo4== E_NAN) blr->initstatus = E_MISSING_MINPO4;
   else if (blr->maxpo4== E_NAN) blr->initstatus = E_MISSING_MAXPO4;
   else if (blr->phsetpoint
                       == E_NAN &&
            blr->napo4ratio
                       ==E_NAN) blr->initstatus = E_MISSING_RATIOSETPOINT;
#if E_ENGINEERING_UNITS
   else if (blr->spga == E_NAN) blr->initstatus = E_MISSING_SPGA;
   else if (blr->spgb == E_NAN) blr->initstatus = E_MISSING_SPGB;
#endif
?
   else {  /* if we got this far, all required fields have been specified */

/* define initial feed program as feeding the default feed rates */ blr->dt[0] = blr->dt[1] = 0.0;
      blr->fa[0] = blr->fa[1] = blr->fa[2] = blr->fadef;
      blr->fb[0] = blr->fb[1] = blr->fb[2] = blr->fbdef;

blr->lastt = blr->t;        /* set origin of time, po4, and ph */
   blr->lastbdtemp = blr->bdtemp;
```

```
        blr->lastpo4 =  blr->po4;
        blr->lastnh3 =  blr->nh3;
        blr->lastph  =  blr->ph;

/* provide defaults for the optional parameters if they are undefined */ blr->fdt = e_fixNAN(blr->fdt, 0.0); /*assume instantaneous pump changes*/
        blr->dpo4 = e_fixNAN(blr->dpo4, DEFAULT_DPO4);
        blr->dph = e_fixNAN(blr->dph, DEFAULT_DPH);
        blr->dphsetpoint = e_fixNAN(blr->dphsetpoint, DEFAULT_DPHSETPOINT);
        blr->max_sample_interval = e_fixNAN(blr->max_sample_interval,
                DEFAULT_MAX_SAMPLE_INTERVAL);
        blr->max_outofbox_adjustment =
        e_fixNAN(blr->max_outofbox_adjustment, DEFAULT_MAX_OUTOFBOX_ADJUSTMENT);
        blr->beps = e_fixNAN(blr->beps, DEFAULT_BEPS);
        blr->naleakmax = e_fixNAN(blr->naleakmax,
            1.0e3 * (FAMAX(blr)*fabs(NAA(blr)) + FBMAX(blr)*fabs(NAB(blr)) +
                    FAMAX(blr)*fabs(PO4A(blr)) + FBMAX(blr)*fabs(PO4B(blr))));
        blr->naleakmin = e_fixNAN(blr->naleakmin, - blr->naleakmax);
        blr->bdmax = e_fixNAN(blr->bdmax, blr->m/1.0);
/*default bdmax empties boiler in 1 hr*/
        blr->bdmin = e_fixNAN(blr->bdmin, 1.0e-6*blr->m/1.0);
/* defaultf bdmin is blowdown rate needed for a time constant of 1e6 hours */
        blr->max_relative_error = e_fixNAN(blr->max_relative_error,
                                        DEFAULT_MAX_RELATIVE_ERROR);
?
/* apply consistency checks to the constants of the macc4 model */
        if (BDMAX(blr) < BDMIN(blr))
            blr->initstatus = E_BDMAX_LT_BDMIN;
        else if (NALEAKMAX(blr) < NALEAKMIN(blr))
            blr->initstatus = E_NALEAKMAX_LT_NALEAKMIN;
        else if (FAMAX(blr) - FAMIN(blr) <=
                DBL_EPSILON * (fabs(FAMAX(blr))+fabs(FAMIN(blr))))
        blr->initstatus = E_FAMAX_LE_FAMIN;   /* max pump rates less than min */
        else if (FBMAX(blr) - FBMIN(blr) <=
            DBL_EPSILON*fabs(fabs(FBMAX(blr))+fabs(FBMIN(blr))))
        blr->initstatus = E_FBMAX_LE_FBMIN;   /* max pump rates less than min */
        else if (MINPO4(blr) < E_MINMINPO4)
            blr->initstatus = E_MINPO4_LT_MINMINPO4;
        else if (MAXPO4(blr) > E_MAXMAXPO4)
            blr->initstatus = E_MAXPO4_GT_MAXMAXPO4;
        else if (PO4SETPOINT(blr) < MINPO4(blr))
            blr->initstatus = E_PO4SETPOINT_LT_MINPO4;
        else if (PO4SETPOINT(blr) > MAXPO4(blr))
```

```
            blr->initstatus = E_PO4SETPOINT_GT_MAXPO4;
        else if (PO4A(blr) < 0.0)
            blr->initstatus = E_PO4A_LT_ZERO;
        else if (PO4B(blr) < 0.0)
            blr->initstatus = E_PO4B_LT_ZERO;
        else if (e_minnapo4ratio(blr) < E_MINMINNAPO4RATIO)
            blr->initstatus = E_MINRATIO_LT_MINMINRATIO;
        else if (e_maxnapo4ratio(blr) > E_MAXMAXNAPO4RATIO)
            blr->initstatus = E_MAXRATIO_GT_MAXMAXRATIO;
        else if (e_napo4ratio(blr) < e_minnapo4ratio(blr))
            blr->initstatus = E_RATIO_LT_MINRATIO;
        else if (e_napo4ratio(blr) > e_maxnapo4ratio(blr))
            blr->initstatus = E_RATIO_GT_MAXRATIO;
        else if (fabs(NAA(blr)*PO4B(blr) - NAB(blr)*PO4A(blr)) <=
            DBL_EPSILON * (fabs(NAA(blr)*PO4B(blr)) + fabs(NAB(blr)*PO4A(blr))))
            blr->initstatus = E_RATIOA_EQ_RATIOB;  /* both tanks have same na/po4 ratio*/
        else {/*initial blowdown, leak only used for testing--reasonable defaults*/
            blr->l = e_fixNAN(blr->l, 0.0);
            blr->bd = e_fixNAN(blr->bd,
USERBD((FADEF(blr)*PO4A(blr) + FBDEF(blr)*PO4B(blr))/PO4SETPOINT(blr)));
        }
    }
    return(blr->initstatus);
}

/* e_getfeed: retrieves feed rates for pumps a or b for a given time */ double e_getfeed(E_BOILER *blr, double *f) { double deltat = T(blr) - LASTT(blr);
    if (deltat < ROUNDED_DT(blr,0))/*use appropriate part of feed program */
        return(f[0]);
    else if (deltat < ROUNDED_DT(blr,0) + ROUNDED_DT(blr,1))
        return(f[1]);
    else
        return(f[2]);
}
double e_afeed(E_BOILER *blr) {          /* retrieves pump a feed rate */
    return(e_getfeed(blr, blr->fa));
}
double e_bfeed(E_BOILER *blr) {          /* retrieves pump b feed rate */
    return(e_getfeed(blr, blr->fb));
}

/*e_po4pred: predicted po4 concentration   */
```

```
double e_po4pred(E_BOILER *blr) {
        double po4 = LASTPO4(blr);
        double deltatime = T(blr) - LASTT(blr);
        int i = 0;
        double deltat[3];
        deltat[0] = e_min(deltatime,ROUNDED_DT(blr,0));
     deltat[1] = e_min(deltatime - deltat[0], ROUNDED_DT(blr,1));
        deltat[2] = deltatime - deltat[0] - deltat[1];
        for (i = 0; i < 3; i++) {
          po4 = ((FA(blr,i)*PO4A(blr)+FB(blr,i)*PO4B(blr))/BD(blr)) *
  (1.0-exp(- deltat[i]*BD(blr)/M(blr))) +
                    po4*exp( - deltat[i]*BD(blr)/M(blr));
        }
        return(po4);
}
}
/* e_estimate_bd: estimate blowdown (B) via bisection */ double e_estimate_bd(E_BOILER *blr) {
        int bisections = E_MAXBISECTIONS;
        double Blow  = blr->bdmin;
        double Bhigh = blr->bdmax;
        blr->bd = 0.5 * (Blow + Bhigh);
        while (bisections-- && (Bhigh - Blow) >
             blr->beps*(fabs(blr->bdmax) + fabs(blr->bdmin))) {
          if (e_po4pred(blr) > PO4(blr))
            Blow = blr->bd;   /* estimated po4 too high - Blowdown too low */
          else
            Bhigh = blr->bd;  /* estimated po4 too low - Blowdown too high */
          blr->bd = 0.5 * (Blow + Bhigh);
        }
/* flag if the final low, high don't actually bracket the root */
        blr->bd = Blow;
     if (e_po4pred(blr) < PO4(blr)) blr->updatestatus |= E_INCONSISTENT_PO4;
        blr->bd = Bhigh;
     if (e_po4pred(blr) > PO4(blr)) blr->updatestatus |= E_INCONSISTENT_PO4;
        return(blr->bd = 0.5 * (Blow + Bhigh));
}

/*e_napred: predicted na concentration */ double e_napred(E_BOILER *blr) {
        double na = e_na(LASTPO4(blr), LASTPH(blr), LASTBDTEMP(blr),
                                     LASTNH3(blr));
        double deltatime = T(blr) - LASTT(blr);
```

```
        int i = 0;
        double deltat[3];
        deltat[0] = e_min(deltatime,ROUNDED_DT(blr,0));
    deltat[1] = e_min(deltatime - deltat[0], ROUNDED_DT(blr,1));
        deltat[2] = deltatime - deltat[0] - deltat[1];
        for (i=0; i < 3; i++) {
        na = ((FA(blr,i)*NAA(blr) + FB(blr,i)*NAB(blr)+L(blr))/BD(blr)) *
    (1.0-exp( - deltat[i]*BD(blr)/M(blr))) +
            na*exp( - deltat[i]*BD(blr)/M(blr));
        }
        return(na);
}
?
/* e_estimate_l: estimate na "leak" (L) via bisection */ double e_estimate_l(E_BOILER *blr) {
        int bisections = E_MAXBISECTIONS;
     double na     = e_na(PO4(blr), PH(blr), BDTEMP(blr), NH3(blr));
        double Llow  = blr->naleakmin;
        double Lhigh = blr->naleakmax;
        blr->l = 0.5*(Llow+Lhigh);
        while (bisections-- && (Lhigh - Llow) >
        blr->beps*(fabs(blr->naleakmax) + fabs(blr->naleakmin))) {
        if (e_napred(blr) > na) /* estimated na too high - na Leak too high */
            Lhigh = blr->l;
        else          /* estimated na too low - na leak too low */
            Llow = blr->l;
        blr->l = 0.5*(Llow+Lhigh);
        }
/* flag if the final low, high don't actually bracket the root */
        blr->l = Llow;
    if (e_napred(blr) > na) blr->updatestatus |= E_INCONSISTENT_PH;
        blr->l = Lhigh;
    if (e_napred(blr) < na) blr->updatestatus |= E_INCONSISTENT_PH;
        return(blr->l = 0.5*(Llow+Lhigh));
}

/* e_phmodel: computes the current model predicted pH for given boiler.*/
#define LOGBASE2OFRELATIVEPHERROR 64 /*works out to less than 1e-16 pH units*/
double e_phmodel(E_BOILER *blr) {
    double minph = 1.0;
    double maxph = 14.0;
    double ph = 0.5*(minph + maxph);
    double po4 = e_po4pred(blr);
    double na  = e_napred(blr);
```

```
    int i = 0;
    for (i=0; i < LOGBASE2OFRELATIVEPHERROR; i++) {
      if (e_na(po4,ph,BDTEMP(blr), NH3(blr)) > na)
        maxph = ph;
      else
        minph = ph;
      ph = 0.5*(minph + maxph);
    }
    return(ph);
}

/*e_po4model: computes the current model predicted po4 for given boiler*/ double e_po4model(E_BOILER *blr) {
    return (USERPO4(e_po4pred(blr)));
}
?
/* Note on our representation of convex polygon regions:

Convex polygon regions with N vertexes, p1, p2, ... pn are represented by
    N+1 points, R[0], R[1], ..., R[N] as follows:

R[0] = p1;  R[1] = p2; .... R[N-1] = pn; R[N] = p1;

Here p1,p2; p2,p3; ... pn,p1 form the edges of the convex polygon region.

We pass the array, R and number of vertexes, N, when passing a
    convex polygon region to a function; note that it takes an array of
    N+1 points to represent a convex polygon region with N distinct
    vertexes. (You can think of the last point as a delimeter, just like
    the 0 at the end of strings).  */

/* e_perimetercrossings: determines points where a given line
    intersects the perimeter of a given convex polygon region; returns
    number of intersection points */ int e_perimetercrossings(E_VECTOR *vX,  /* 2 element array of intersection pts*/
                         E_VECTOR *vV,  /* V[i],V[i+1] are edges; V[NV]==V[0]*/
                         int NV,        /* number of vertexes in region */
                         E_VECTOR *vP1,/* line that (may) intersect region */
                         E_VECTOR *vP2)/* P1 <> P2 is required ! */
{
    int i = 0, N = 0;
```

```
        double lastalpha, lastbeta, alpha, beta;
        e_decompose(&vV[0], vP1, e_vSv(vP2,vP1), e_rot90(e_vSv(vP2,vP1)),
              &lastalpha, &lastbeta);
        for (i=0; i < NV; i++) {
           e_decompose(&vV[i+1], vP1, e_vSv(vP2,vP1), e_rot90(e_vSv(vP2,vP1)),
              &alpha, &beta);
           if (lastbeta*beta <= 0.0 &&    /* does edge crosses given line ? */
               (fabs(lastbeta) > 0.0 || fabs(beta) > 0.0 ) ) {
              E_VECTOR *X = e_vPv(&vV[i],
                   e_sXv(fabs(lastbeta)/(fabs(lastbeta)+fabs(beta)),
                       e_vSv(&vV[i+1],&vV[i])));
              if (N < 2)
                 vX[N++] = *X;
              else if (e_between(&vX[1], &vX[0], X))
                 vX[0] = *X;
              else if (e_between(&vX[0], &vX[1], X))
                 vX[1] = *X;
           /* else first 2 intersection points are already the furthest apart */
           }
           lastbeta = beta;
        }
        return(N);
    }
}

/* e_within_region: is the given point within (or on perimeter of) region ? */

E_LOGICAL e_within_region(E_VECTOR *vP, E_VECTOR *vR, int N) {
    E_VECTOR vX[2];
    if ( e_vEv(vP, &vR[0]) )
       return(E_TRUE);
    else if (e_perimetercrossings(vX, vR, N, vP, &vR[0]) > 1 &&
               E_TRUE == e_between(&vX[0], vP, &vX[1]) )
       return(E_TRUE);
    else
       return(E_FALSE);
}

/*
    e_clip_region: clips the part of the convex polygon region, R,
    that is to your left if you are standing at P1 and walking towards P2
    (or walking backwards from P2 towards P1). Assumes P1 <> P2.
*/ int e_clip_region(E_VECTOR *vC,  /* clipped region (output) */
                  E_VECTOR *vR,  /* original region (input) */
```

```
                    int N,        /* number of distinct points on perimeter */
                    E_VECTOR *vP1, E_VECTOR *vP2) { /* clipping line */
    double alpha, beta, lastbeta;
    int i = 0, j = 0;

e_decompose(&vR[0], vP1, e_vSv(vP2, vP1), e_rot90(e_vSv(vP2, vP1)),
                    &alpha, &beta);
    for (i=0; i < N; i++) {
        if (beta <= 0)  /* to the right of, or on, the clipping line through P1,P2*/
            vC[j++] = vR[i];
        lastbeta = beta;
        e_decompose(&vR[i+1], vP1, e_vSv(vP2,vP1), e_rot90(e_vSv(vP2, vP1)),
                    &alpha, &beta);
        if (lastbeta*beta < 0.0)  /* Segment R[i],R[i+1] crosses clipping line: */
            vC[j++] = *e_vPv(&vR[i], /*add point where it crosses to clipped region*/
                    e_sXv(fabs(lastbeta)/(fabs(lastbeta)+fabs(beta)),
                    e_vSv(&vR[i+1], &vR[i])));
    } vC[j] = vC[0];    /* "close the loop" to form the convex polygon region */
    return (j);

}
?
/*
    e_intersect_regions: determines the region, AB, which is the
    intersection of the two given convex polygon regions, A and B. The
    first region, A, must be oriented such that moving from vertex A[i]
    to vertex A[i+1] places the outside of the region to one's left (in
    other words, you are moving clockwise around the perimeter).

IMPORTANT: AB[] MUST contain at least NA+NB+1 elements, which is
    the maximum possible number of points needed to define the region of
    intersection, or memory will be trashed. Function returns the number
        of distinct vertexes in the resulting, intersecting, region.

For more information, see section 3.14.1, "The Sutherland-Hodgman
    Polygon-Clipping Algorithm", of the second edition of Foley, et. al's
        "Computer Graphics" 1990, Addison-Wesley.
*/ int e_intersect_regions(E_VECTOR *vAB, /* intersecting region (returns NAB) */
                    E_VECTOR *vA,   /* points representing the 1st region */
                    int NA,         /* number of vertexes in 1st region */
                    E_VECTOR *vB,   /* points representing the 2nd region */
                    int NB) {       /* number of vertexes in 2nd region */
```

```
        int i = 0, j = 0, N = NB;
        for (i = 0; i < NA; i++) {
            for (j = N; j >= 0; j--) { /* copy/move region to be clipped to end of AB*/
                vAB[NA+NB-N+j] = (i==0) ? vB[j] : vAB[j];/*AB[] MUST have NA+NB+1 elems*/
            }
            N = e_clip_region(vAB, vAB+NA+NB-N, N, &vA[i], &vA[i+1]);
        }
        return(N);
    }

/* e_point2chord: return point on the chord (line-segment) closest to P */

E_VECTOR *e_point2chord(E_VECTOR *vP, E_VECTOR *vL1, E_VECTOR *vL2) { if (e_vEv(vL1, vL2))
            return(vL1);
        else {
            double alpha, beta;
            e_decompose(vP, vL1, e_vSv(vL2, vL1), e_rot90(e_vSv(vL2, vL1)),
                        &alpha, &beta);
            return(e_vPv(vL1, e_sXv(e_max(0.0, e_min(1.0, alpha)), e_vSv(vL2, vL1))));
        }
    }

/* e_region2region: given 2 non-intersecting convex polygon regions, returns
       the point on region A that is closest to (the perimeter of) region B */

E_VECTOR *e_region2region(E_VECTOR *vA, int NA, E_VECTOR *vB, int NB) {
        E_VECTOR vminA = vA[0], vminB = vB[0], vX;
        int i = 0, j = 0;
        for (i=0; i < NA; i++) {
            for (j = 0; j < NB; j++) {
                vX = *e_point2chord(&vA[i], &vB[j], &vB[j+1]);
                if (e_norm(e_vSv(&vA[i], &vX)) < e_norm(e_vSv(&vminA, &vminB))) {
                    vminA = vA[i];
                    vminB = vX;
                }
            }
        }
        for (i=0; i < NB; i++) {
            for (j = 0; j < NA; j++) {
                vX = *e_point2chord(&vB[i], &vA[j], &vA[j+1]);
                if (e_norm(e_vSv(&vX, &vB[i])) < e_norm(e_vSv(&vminA, &vminB))) {
```

```
            vminA = vX;
            vminB = vB[i];
         }
      }
   }
   return(e_vec(vminA.po4,vminA.na));
} define E_REPS 5   /* number of replicates for sensitivity analysis */

/* e_pertubate: perturbs field in boiler structure for sensitivity analysis */ void e_perturbate(E_BOILER *blr, int index, double multiplier) {
   switch(index) {
      case 0: blr->lastpo4  += (multiplier*blr->dpo4);
              break;
      case 1: blr->lastph   += (multiplier*blr->dph);
              break;
      case 2: blr->po4      += (multiplier*blr->dpo4);
              break;
      case 3: blr->ph       += (multiplier*blr->dph);
              break;
      default: break;
   }
}

/* e_backup: stores E_BOILER's current state for later use by e_undo */ void e_backup(E_BOILER *blr) {
   int i = 0;
   for (i=0; i < 2; i++) blr->lastdt[i] = blr->dt[i];
   for (i=0; i < 3; i++) {
      blr->lastfa[i] = blr->fa[i];
      blr->lastfb[i] = blr->fb[i];
   }
   blr->b4lastt        = blr->lastt;
   blr->b4lastbdtemp   = blr->lastbdtemp;
   blr->b4lastpo4      = blr->lastpo4;
   blr->b4lastnh3      = blr->lastnh3;
   blr->b4lastph       = blr->lastph;

blr->lastbd         = blr->bd;
   blr->lastl          = blr->l;
   for (i=0; i < E_NV+1; i++)  blr->vlastV[i] = blr->vV[i];
   for (i=0; i < E_NW+1; i++)  blr->vlastW[i] = blr->vW[i];
   for (i=0; i < 3; i++)       blr->vlastF[i] = blr->vF[i];
```

75

```
        blr->lastupdatestatus = blr->updatestatus;

blr->undoable = E_TRUE;  /* since we are backed up, an undo is now possible */

}
     /* e_undo: undoes the effect of the last e_update(); 1 update can be undone. */

E_LOGICAL e_undo(E_BOILER *blr) {
    if (E_FALSE == blr->undoable)
       return(E_FALSE);
    else {
       int i = 0;
       for (i=0; i < 2; i++) blr->dt[i] = blr->lastdt[i];
       for (i = 0; i < 3; i++) {
          blr->fa[i] = blr->lastfa[i];
          blr->fb[i] = blr->lastfb[i];
       } blr->lastt        = blr->b4lastt;
       blr->lastbdtemp   = blr->b4lastbdtemp;
       blr->lastpo4      = blr->b4lastpo4;
       blr->lastnh3      = blr->b4lastnh3;
       blr->lastph       = blr->b4lastph;

blr->bd           = blr->lastbd;
       blr->l            = blr->lastl;
       for (i=0; i < E_NV+1; i++)  blr->vV[i] = blr->vlastV[i];
       for (i=0; i < E_NW+1; i++)  blr->vW[i] = blr->vlastW[i];
       for (i=0; i < 3; i++)       blr->vF[i] = blr->vlastF[i];
       blr->updatestatus = blr->lastupdatestatus;

blr->undoable = E_FALSE;  /* no more than 1 undo between updates */
       return(E_TRUE);
    }
}
?
/* e_update: update the feed program associated with a boiler */

E_UPDATESTATUS e_update(E_BOILER *blr)
{
    int i = 0, i0 = 0, NV = E_NV, NW = E_NW, NVW = 0;
    E_VECTOR vfamin, vfamax, vfbmin, vfbmax, vL;
    E_VECTOR *vV=blr->vV, vminV, *vW=blr->vW, vminW, vVW[E_NV+E_NW+1];
    E_VECTOR vP, vT, vSS;
    E_VECTOR *vF = blr->vF, vX[2];
    double fa[E_REPS], fb[E_REPS];
```

```
        double ssq = 0.0;

e_backup(blr);    /* backup the current state for undo purposes */
    blr->updatestatus = E_UPDATEOK;      /* clear any previous status */
/*define the target wedge (the "box" in coordinated phosphate/ph lingo)... */
/*N.B: the region described by vW must be oriented in
    the clockwise direction, c.f. comment at top of e_intersect_regions() */
    vW[0]    = *e_vec(MINPO4(blr), MINPO4(blr)*e_minnapo4ratio(blr));
    vW[1]    = *e_vec(MINPO4(blr), MINPO4(blr)*e_maxnapo4ratio(blr));
    vW[2]    = *e_vec(MAXPO4(blr), MAXPO4(blr)*e_maxnapo4ratio(blr));
    vW[3]    = *e_vec(MAXPO4(blr), MAXPO4(blr)*e_minnapo4ratio(blr));
    vW[4]    = vW[0];
/* ... and target point */
    vT = *e_vec(PO4SETPOINT(blr), PO4SETPOINT(blr)*e_napo4ratio(blr));

/* Estimate the steady-state boiler concentration variability due to */
/* the given variability of PO4 (dpo4) and pH (dph), via a propagation */
/* of errors calculation. We assume that the impacts of the errors in  */
/* lastpo4, lastph, po4, and ph on steady state boiler concentrations */
/* are independent; since this is not strictly true, the calculation */
/* below will tend to overestimate the resulting error on steady state */
/* boiler concentrations. But it should be a reasonable estimate. */ i0 = ((DPO4(blr)<=0.0 && DPH(blr) <= 0.0) ? (E_REPS-1) : 0);
    for (i = i0; i < E_REPS; e_perturbate(blr, i++, -1.0)) {
/* this loop evaluates steady-state feed rates using pertubated inputs */
        e_perturbate(blr, i, 1.0);    /* varies one of: lastpo4,lastph,po4,ph */
        blr->bd = e_estimate_bd(blr); /* (if i = E_REPS-1 then it varies nothing)*/
        blr->l  = e_estimate_l(blr);

vfamin = *e_vec(FAMIN(blr)*PO4A(blr)/BD(blr),
                        FAMIN(blr)*NAA(blr)/BD(blr));
        vfbmin = *e_vec(FBMIN(blr)*PO4B(blr)/BD(blr),
                        FBMIN(blr)*NAB(blr)/BD(blr));
        vfamax = *e_vec(FAMAX(blr)*PO4A(blr)/BD(blr),
                        FAMAX(blr)*NAA(blr)/BD(blr));
        vfbmax = *e_vec(FBMAX(blr)*PO4B(blr)/BD(blr),
                        FBMAX(blr)*NAB(blr)/BD(blr));
        vL     = *e_vec(0.0, L(blr)/BD(blr));
        e_decompose (&vT, &vL, e_vDs(&vfamax, FAMAX(blr)),
              e_vDs(&vfbmax, FBMAX(blr)), &fa[i], &fb[i]);

}
```

```
for (ssq = 0.0, i = i0; i < E_REPS-1; i++) { /* sum up the squared errors*/
    ssq += e_norm2(                          /* on steady-state boiler    */
            e_vSv(&vT,                       /* concentrations due to     */
            e_vPv(&vL,                       /* the various perturbations*/
            e_vec((fa[i]*PO4A(blr)+fb[i]*PO4B(blr))/BD(blr),
                  (fa[i]*NAA(blr)+fb[i]*NAB(blr))/BD(blr)
            )
          )
        )
    );
} if ( sqrt(ssq) > MAX_RELATIVE_ERROR(blr) * e_norm(&vT) ) {
    blr->updatestatus |= E_INDETERMINATE;  /* variability of steady-state  */
    blr->updatestatus |= E_NOTUPDATED;     /* boiler concentrations is too big*/
} if ((E_INCONSISTENT_PO4 | E_INCONSISTENT_PH) & blr->updatestatus)
    blr->updatestatus |= E_NOTUPDATED;  /* feed program not updated */
                                        /* if PO4 or pH are inconsistent*/
                                        /* with blowdown or Na leak ranges*/ if (E_NOTUPDATED & blr->updatestatus) goto nochange;

/* define the steady state feasable region in boiler conc space... */
    vV[0]   = *e_vPv(&vL, e_vPv(&vfamin, &vfbmin));
    vV[1]   = *e_vPv(&vL, e_vPv(&vfamax, &vfbmin));
    vV[2]   = *e_vPv(&vL, e_vPv(&vfamax, &vfbmax));
    vV[3]   = *e_vPv(&vL, e_vPv(&vfamin, &vfbmax));
    vV[4]   = vV[0];
/* ... and the current point */
    vP   = *e_vec(PO4(blr), e_na(PO4(blr),PH(blr), BDTEMP(blr), NH3(blr)));

/* compute the steady-state feed rate, defined to be the point within the
   feasable region that is closest to the target wedge, and, secondarily, if
   the feasable region and target wedge overlap, closest to the target point.*/ if ((NVW=e_intersect_regions(vVW, vW, NW, vV, NV)) > 0) {
    /*regions intersect */
    if (e_within_region(&vT, vVW, NVW))
        vSS = vT;
    else {                               /* target not in feasable region*/
        vX[0] = vX[1] = vT;
        vSS = *e_region2region(vVW, NVW, vX, 1);
        blr->updatestatus |= E_POINT_UNMAINTAINABLE;
```

```
            }
        }
        else {                                       /* regions are disjoint*/
            blr->updatestatus |= E_POINT_UNMAINTAINABLE;
            blr->updatestatus |= E_BOX_UNMAINTAINABLE;
            vSS = *e_region2region(vV, NV, vW, NW);
        }
    blr->dt[0] = blr->dt[1] = 0.0;      /* set default feed program to */
    vF[0] = vF[1] = vF[2] = vSS;        /* steady state feed rates */
    }
    /* Adjust na/po4 ratio (stage 1 of feed program) */ if (E_FALSE==e_within_region(&vP, vW, NW)) {    /* if already in the box */
        int i = 0, j = 0;                           /* no stage 1 adjustment required */
        E_LOGICAL region_unreachable = E_TRUE;
        for (i=0; i < NV; i++) {
            if (!e_vEv(&vP, &vV[i]) &&
                e_perimetercrossings(vX, vW, NW, &vP, &vV[i]) > 1) {
                for (j=0; j < 2; j++) {
                    if (e_between(&vP, &vX[j], &vV[i])) {
                        if (region_unreachable) {
                            vminV = vV[i];
                            vminW = vX[j];
                            region_unreachable = E_FALSE;
                        }
                        else if (e_norm(e_vSv(&vV[i],&vX[j]))*e_norm(e_vSv(&vminV,&vP)) >
                            e_norm(e_vSv(&vminV,&vminW))*e_norm(e_vSv(&vV[i],&vP))) {
                            vminV = vV[i];
                            vminW = vX[j];
                        }
                    }
                }
            }
        }
        for (i=0; i < NW; i++) {
            if (!e_vEv(&vP, &vW[i]) &&
                e_perimetercrossings(vX, vV, NV, &vP, &vW[i]) > 1) {
                for (j=0; j < 2; j++) {
                    if (e_between(&vP, &vW[i], &vX[j])) {
                        if (region_unreachable) {
                            vminV = vX[j];
                            vminW = vW[i];
                            region_unreachable = E_FALSE;
                        }
                        else if (e_norm(e_vSv(&vX[j],&vW[i]))*e_norm(e_vSv(&vminV, &vP)) >
```

```
                    e_norm(e_vSv(&vminV,&vminW)) *e_norm(e_vSv(&vX[i],&vP)))}
                vminV = vX[i];
                vminW = vW[i];
            }
        }
    }
}
if (region_unreachable==E_TRUE ||
        (e_norm(e_vSv(&vminV,&vminW)) <=
        2.0*DBL_MIN*e_norm(e_vSv(&vminV, &vP))))
    blr->updatestatus |= E_BOX_UNREACHABLE;
else {
    blr->dt[0] = - (M(blr)/BD(blr)) *
        log(e_norm(e_vSv(&vminV,&vminW))/e_norm(e_vSv(&vminV, &vP)));
    vF[0] = vminV;
    vP  =      vminW;
    if (DT(blr,0) > MAX_OUTOFBOX_ADJUSTMENT(blr)) {
        blr->updatestatus |= E_OUTOFBOX_TOOLONG;
    }
}
        }
    }
?
/* Stage 2: move to the setpoint po4 and NA/po4 ratio if you can */ if (!e_vEv(&vP, &vT)) {
    if (e_perimetercrossings(vX, vV, NV, &vP, &vT) <= 1)
        blr->updatestatus |= E_POINT_UNREACHABLE;
    else {
        int i = 0;
        E_LOGICAL point_unreachable = E_TRUE;
        for (i=0; i < 2; i++) {
            if (e_between(&vP, &vT, &vX[i])) {
                if (point_unreachable) {
                    vminV = vX[i];
                    point_unreachable = E_FALSE;
                }
                else if (e_norm(e_vSv(&vX[i],&vT))*e_norm(e_vSv(&vminV, &vP)) >
                         e_norm(e_vSv(&vminV,&vT))*e_norm(e_vSv(&vX[i],&vP)))
                    vminV = vX[i];
            }
        }
        if (E_TRUE==point_unreachable ||
            e_norm(e_vSv(&vminV,&vT)) <= 2.0*DBL_MIN*e_norm(e_vSv(&vminV, &vP)))
            blr->updatestatus |= E_POINT_UNREACHABLE;
        else {
```

```c
        blr->dt[1] = - (M(blr)/BD(blr)) *
            log(e_norm(e_vSv(&vminV,&vT))/e_norm(e_vSv(&vminV, &vP)));
        vF[1] = vminV;
      }
    }
  } for (i=0; i < 3; i++) { /* determine feed rates needed to attain feed points */
    e_decompose(&vF[i], &vL, e_vDs(&vfamax,blr->famax),
            e_vDs(&vfbmax,blr->fbmax), &blr->fa[i], &blr->fb[i]);
    blr->fa[i] = e_forceinrange(blr->fa[i],blr->famin,blr->famax);/*fixes up*/
    blr->fb[i] = e_forceinrange(blr->fb[i],blr->fbmin,blr->fbmax);/*roundoff*/
  } if (T(blr) - LASTT(blr) > MAX_SAMPLE_INTERVAL(blr))
    blr->updatestatus |= E_SAMPLEINTERVAL_TOOLONG;

blr->lastt       = blr->t;      /* make prev current values last values */
  blr->lastpo4     = blr->po4;
  blr->lastnh3     = blr->nh3;
  blr->lastph      = blr->ph;
  blr->lastbdtemp  = blr->bdtemp;

nochange:              /* if we jump to here, feed program not updated*/ return(blr->updatestatus);

}

?
const E_BOILER *e_undefined_boiler(void) {
  static const E_BOILER E_UNDEFINED_BOILER = {
E_NAN,E_NAN,E_NAN,E_NAN,E_NAN,E_NAN,E_NAN,E_NAN,E_NAN,E_NAN,E_NAN,E_NAN,
E_NAN,E_NAN,E_NAN,E_NAN,E_NAN,E_NAN,E_NAN,E_NAN,E_NAN,E_NAN,E_NAN,E_NAN,E_NAN,
E_NAN,E_NAN,E_NAN,E_NAN,E_NAN,E_NAN,E_NAN,E_NAN,E_NAN,E_NAN,E_NAN,E_NAN,E_NAN,
E_NAN,E_NAN,E_NAN,E_NAN,E_NAN,E_NAN,E_NAN,E_NAN,E_NAN,E_NAN,E_NAN,E_NAN,E_NAN,
{0.0,0.0},{E_NAN,E_NAN,E_NAN},{E_NAN,E_NAN,E_NAN},
{0.0,0.0},{E_NAN,E_NAN,E_NAN},{E_NAN,E_NAN,E_NAN},
{{0.0,0.0}, {0.0,0.0}, {0.0,0.0}, {0.0,0.0}, {0.0,0.0}},
{{0.0,0.0}, {0.0,0.0}, {0.0,0.0}, {0.0,0.0}, {0.0,0.0}},
{{0.0,0.0}, {0.0,0.0}, {0.0,0.0}, {0.0,0.0}, {0.0,0.0}},
{{0.0,0.0}, {0.0,0.0}, {0.0,0.0}, {0.0,0.0}, {0.0,0.0}},
{{0.0,0.0}, {0.0,0.0}, {0.0,0.0}, {0.0,0.0}, {0.0,0.0}},
{{0.0,0.0}, {0.0,0.0}, {0.0,0.0}},
E_UPDATEOK, E_UPDATEOK, E_INITOK, E_FALSE};
```

```
return(&E_UNDEFINED_BOILER);
}

/* e_hpm2po4: converts hmp (expressed as % by weight) to ortho PO4 */
/* (also in % by weight) */
double e_hmp2po4(double hmp) {
   return(0.93135 * hmp);  /* conversion factor provided by SMB Aug 4 */
}
```

```c
/* macc4ssp.h */ define IDC_PASSWORD        155
define IDC_LOCKWINDOW      156
#define IDC_DATETIME        157
#define MACC4SSP_ICON       2
#define MACC4SSP_DIALOG     1
#define IDC_GROUPBOX1       101
#define IDC_BD  152
#define IDC_BDMIN           131
#define IDC_BDMAX           132
#define IDC_M    130
#define IDC_BDTEMP          127
#define IDC_DPHSETPOINT     126
#define IDC_PHSETPOINT      125
#define IDC_DPH  124
#define IDC_PH   123
#define IDC_MAXPO4          120
#define IDC_MINPO4          119
#define IDC_PO4SETPOINT     118
#define IDC_DPO4            117
#define IDC_PO4 116
#define IDC_SPGA            146
#define IDC_SPGB            114
#define IDC_PO4B            112
#define IDC_FBDEF           111
#define IDC_FBMAX           110
#define IDC_FBMIN           109
#define IDC_RATIOB          107
#define IDC_RATIOA          106
#define IDC_PO4A            105
#define IDC_FADEF           104
#define IDC_STATUSFLAGS     151
#define IDC_POINTNAMES      154
#define IDC_START           121
#define IDC_SIMULATESSP     147
#define IDC_NH3ENABLED      162
#define IDC_NH3TEXT         163
define IDC_NH3  164 define IDC_AFEED           200
define IDC_BFEED           201
```

```
#define IDC_FAMAX            103
#define IDC_FAMIN            102
#define IDC_GROUPBOX5        129
#define IDC_MESSAGELINE      145
#define IDC_LOGTOFILE        113
#define IDC_GROUPBOX6        148
#define IDC_ENGINE9          144
#define IDC_ENGINE8          143
#define IDC_ENGINE7          142
#define IDC_ENGINE6          141
#define IDC_ENGINE5          140
#define IDC_ENGINE4          139
#define IDC_ENGINE3          138
#define IDC_ENGINE2          137
#define IDC_ENGINE1          136
#define IDC_ENGINE0          135
#define IDC_STOP             122
#define IDC_UNDO             204
#define IDC_REINIT           203
#define IDC_UPDATE           202
#define IDC_LOCALINPUT       158
#define IDC_FORECASTTIME            149
#define IDC_FORECAST         150
#define IDC_GROUPBOX4        -1
#define IDC_GROUPBOX3        115
#define IDC_GROUPBOX2        108
#define IDC_FWFLOW           128
#define IDC_FWNA             161
#define IDC_MAXFWNA          160
define IDC_MINFWNA          159 define IDC_AFEED   200        /* SSP communication id's */
define IDC_BFEED   201        /*(IDC_PH, IDC_PO4, and IDC_BDTEMP also used)*/
#define IDC_FLAG1   205
#define IDC_FLAG2   206
#define IDC_FLAG3   207
#define IDC_FLAG4   208
#define IDC_FLAG5   209
#define IDC_FLAG6   210
#define IDC_FLAG7   211
#define IDC_FLAG8   212
#define IDC_FLAG9   213
#define IDC_FLAG10  214
#define IDC_FLAG11  215
```

```
#define IDC_FLAG12  216
define IDC_RATIO   217 define IDC_T   300             /* E_BOILER field ids that do not have */
define IDC_NAPO4RATIO  301     /* a control associated with them */
#define IDC_MINNAPO4RATIO  302
#define IDC_MAXNAPO4RATIO  303
#define IDC_MAX_SAMPLE_INTERVAL  304
#define IDC_MAX_OUTOFBOX_ADJUSTMENT  305
#define IDC_MAX_RELATIVE_ERROR  306
#define IDC_BEPS  307
#define IDC_FDT  308
#define IDC_LASTT  309
#define IDC_LASTBDTEMP  310
#define IDC_LASTPO4  311
#define IDC_LASTPH  312
#define IDC_B4LASTT  313
#define IDC_B4LASTBDTEMP  314
#define IDC_B4LASTPO4  315
#define IDC_B4LASTPH  316
#define IDC_LASTBD  319
#define IDC_LASTL  320
#define IDC_DT1  321
#define IDC_DT2  322
#define IDC_FA1  323
#define IDC_FA2  324
#define IDC_FA3  325
#define IDC_FB1  326
#define IDC_FB2  327
#define IDC_FB3  328
#define IDC_LASTDT1  329
#define IDC_LASTDT2  330
#define IDC_LASTFA1  331
#define IDC_LASTFA2  332
#define IDC_LASTFA3  333
#define IDC_LASTFB1  334
#define IDC_LASTFB2  335
#define IDC_LASTFB3  336
#define IDC_UPDATESTATUS  337
#define IDC_LASTUPDATESTATUS  338
#define IDC_INITSTATUS  339
#define IDC_UNDOABLE  340
#define IDC_LASTNH3  341
#define IDC_B4LASTNH3  342
```

```
/* misc/MACC4SSP specific/state/control/error ids */
#define IDC_CURRENTENGINEID 401
#define IDC_RUNNING 402
#define IDC_FLAGSUPTODATE 403
#define IDC_ACTIONSUPTODATE 404
#define IDC_SCIERR 405
#define IDC_PIDSCIERR 406
#define IDC_ACTION 407
#define IDC_CHECKSUM 408
#define IDC_LOADFORM 409
#define IDC_LASTEVENTTIME 410
#define IDC_EVENTID 411
#define IDC_STARTTIME 412
#define IDC_LAUNCH 413
#define IDC_CLOSE 414
```

```
/************************************************************* macc4ssp.rc produced by Borland Resource Workshop

*************************************************************/ define IDC_PASSWORD    155
define IDC_FWNA        161
#define IDC_MAXFWNA     160
#define IDC_MINFWNA     159
#define IDC_LOCKWINDOW  156
#define IDC_DATETIME    157
#define MACC4SSP_ICON   2
#include <windows.h>
#define MACC4SSP_DIALOG 1
#define IDC_GROUPBOX1   101
#define IDC_BD          152
#define IDC_BDMIN       131
#define IDC_BDMAX       132
#define IDC_M           130
#define IDC_BDTEMP      127
#define IDC_DPHSETPOINT 126
#define IDC_PHSETPOINT  125
#define IDC_DPH         124
#define IDC_PH          123
#define IDC_MAXPO4      120
#define IDC_MINPO4      119
#define IDC_PO4SETPOINT 118
#define IDC_DPO4        117
#define IDC_PO4         116
#define IDC_NH3TEXT     163
#define IDC_NH3         164
#define IDC_SPGA        146
#define IDC_SPGB        114
#define IDC_PO4B        112
#define IDC_FBDEF       111
#define IDC_FBMAX       110
#define IDC_FBMIN       109
#define IDC_RATIOB      107
#define IDC_RATIOA      106
#define IDC_PO4A        105
#define IDC_FADEF       104
```

```
#define  IDC_STATUSFLAGS?151
#define  IDC_POINTNAMES?154
#define  IDC_NH3UNDERLINE?165
#define  IDC_START?121
#define  IDC_SIMULATESSP?147
#define  IDC_AFEED?200
#define  IDC_BFEED?201
#define  IDC_FAMAX?103
#define  IDC_FAMIN?102
#define  IDC_GROUPBOX5?129
#define  IDC_MESSAGELINE?145
#define  IDC_LOGTOFILE?113
#define  IDC_NH3ENABLED?162
#define  IDC_FWFLOW?128
#define  IDC_GROUPBOX6?148
#define  IDC_ENGINE9?144
#define  IDC_ENGINE8?143
#define  IDC_ENGINE7?142
#define  IDC_ENGINE6?141
#define  IDC_ENGINE5?140
#define  IDC_ENGINE4?139
#define  IDC_ENGINE3?138
#define  IDC_ENGINE2?137
#define  IDC_ENGINE1?136
#define  IDC_ENGINE0?135
#define  IDC_STOP?122
#define  IDC_UNDO?204
#define  IDC_REINIT?203
#define  IDC_UPDATE?202
#define  IDC_LOCALINPUT?158
#define  IDC_FORECASTTIME?149
#define  IDC_FORECAST?150
#define  IDC_GROUPBOX4?-1
#define  IDC_GROUPBOX3?115
#define  IDC_GROUPBOX2?108
MACC4SSP_DIALOG DIALOG 1, 1, 352, 248
STYLE WS_OVERLAPPED | WS_CAPTION | WS_SYSMENU | WS_MINIMIZEBOX
CLASS "MACC4SSP"
CAPTION "MACC4SSP Boiler0 (ERROR_NONE)"
FONT 8, "MS Sans Serif"
{
  LTEXT "Password:", -1, 4, 4, 34, 8
  EDITTEXT IDC_PASSWORD, 41, 2, 43, 12, ES_UPPERCASE | ES_PASSWORD | WS_BORDER | WS_TABSTOP
  PUSHBUTTON "Lock", IDC_LOCKWINDOW, 87, 2, 20, 12
  CONTROL "Last update:", -1, "STATIC", SS_LEFTNOWORDWRAP | WS_CHILD | WS_VISIBLE | WS_GROUP, 110, 4, 42, 8
```

```
CONTROL "24-Dec-1994 09:24:29", IDC_DATETIME, "STATIC", SS_LEFTNOWORDWRAP | WS_CHILD | WS_VISIBLE | WS_BORDER | WS_GROUP, 151, 4, 76, 9
GROUPBOX "Pump/Tank A", IDC_GROUPBOX1, 4, 14, 109, 91, BS_GROUPBOX
LTEXT "Min Feed (gpd):", -1, 12, 30, 52, 12
EDITTEXT IDC_FAMIN, 70, 28, 40, 12
CONTROL "Max Feed (gpd):", -1, "STATIC", SS_LEFTNOWORDWRAP | WS_CHILD | WS_VISIBLE | WS_GROUP, 12, 42, 52, 12
EDITTEXT IDC_FAMAX, 70, 40, 40, 12
CONTROL "Init. Feed (gpd):", -1, "STATIC", SS_LEFTNOWORDWRAP | WS_CHILD | WS_VISIBLE | WS_GROUP, 12, 54, 53, 12
EDITTEXT IDC_FADEF, 70, 52, 40, 12
LTEXT "PO4 (% by wt.):", -1, 12, 66, 53, 12
EDITTEXT IDC_PO4A, 70, 64, 40, 12
LTEXT "Na/PO4 ratio:", -1, 12, 78, 52, 12
EDITTEXT IDC_RATIOA, 70, 76, 40, 12
LTEXT "Specific Gravity:", -1, 12, 90, 55, 12
EDITTEXT IDC_SPGA, 70, 88, 40, 12
GROUPBOX "Pump/Tank B", IDC_GROUPBOX2, 118, 15, 109, 90, BS_GROUPBOX
CONTROL "Min Feed (gpd):", -1, "STATIC", SS_LEFTNOWORDWRAP | WS_CHILD | WS_VISIBLE | WS_GROUP, 127, 29, 54, 12
EDITTEXT IDC_FBMIN, 183, 28, 40, 12
CONTROL "Max Feed (gpd):", -1, "STATIC", SS_LEFTNOWORDWRAP | WS_CHILD | WS_VISIBLE | WS_GROUP, 127, 41, 54, 12
EDITTEXT IDC_FBMAX, 183, 40, 40, 12
CONTROL "Init. Feed (gpd):", -1, "STATIC", SS_LEFTNOWORDWRAP | WS_CHILD | WS_VISIBLE | WS_GROUP | WS_TABSTOP, 127, 53, 54, 12
EDITTEXT IDC_FBDEF, 183, 52, 40, 12
LTEXT "PO4 (% by wt.):", -1, 127, 64, 52, 12
EDITTEXT IDC_PO4B, 183, 64, 40, 12
LTEXT "Na/PO4 ratio:", -1, 127, 76, 49, 12
EDITTEXT IDC_RATIOB, 183, 76, 40, 12
LTEXT "Specific Gravity:", -1, 127, 88, 56, 12
EDITTEXT IDC_SPGB, 183, 88, 40, 12
GROUPBOX "Boiler Phosphate", IDC_GROUPBOX3, 4, 109, 109, 91, BS_GROUPBOX
CONTROL "Phosphate (ppm):", -1, "STATIC", SS_LEFTNOWORDWRAP | WS_CHILD | WS_VISIBLE | WS_GROUP, 10, 124, 57, 8
EDITTEXT IDC_PO4, 70, 122, 40, 12
LTEXT "Variability (ppm):", -1, 11, 136, 55, 10
EDITTEXT IDC_DPO4, 70, 134, 40, 12
LTEXT "Set Point (ppm):", -1, 10, 147, 55, 9
EDITTEXT IDC_PO4SETPOINT, 70, 146, 40, 12
LTEXT "Min (ppm):", -1, 10, 159, 54, 10
EDITTEXT IDC_MINPO4, 70, 158, 40, 12
LTEXT "Max (ppm):", -1, 10, 171, 52, 10
EDITTEXT IDC_MAXPO4, 70, 170, 40, 12
CONTROL "pH:", -1, "STATIC", SS_LEFTNOWORDWRAP | WS_CHILD | WS_VISIBLE | WS_GROUP, 128, 124, 59, 10
EDITTEXT IDC_PH, 184, 123, 40, 12
LTEXT "Variability:", -1, 128, 137, 38, 12
EDITTEXT IDC_DPH, 184, 135, 40, 12
LTEXT "Setpoint:", -1, 128, 150, 30, 10
EDITTEXT IDC_PHSETPOINT, 157, 149, 31, 13
LTEXT "+/-", -1, 188, 151, 11, 9
EDITTEXT IDC_DPHSETPOINT, 199, 149, 25, 13
```

```
EDITTEXT IDC_BDTEMP, 184, 164, 40, 12
CHECKBOX " ", IDC_NH3ENABLED, 119, 176, 9, 11, BS_AUTOCHECKBOX | WS_TABSTOP
CONTROL "NH3 (ppm)*:", IDC_NH3TEXT, "STATIC", SS_LEFTNOWORDWRAP | WS_CHILD | WS_VISIBLE | WS_GROUP, 128, 177, 50, 8
EDITTEXT IDC_NH3, 184, 176, 40, 12
CONTROL "", IDC_NH3UNDERLINE, "static", SS_BLACKFRAME | WS_CHILD | WS_VISIBLE | WS_BORDER, 128, 186, 39, 1
LTEXT "* of boiler water pH sample", -1, 120, 190, 106, 9
GROUPBOX "Other Parameters", IDC_GROUPBOX5, 231, 109, 117, 91, BS_GROUPBOX
CONTROL "BW Mass (lbs):", -1, "STATIC", SS_LEFTNOWORDWRAP | WS_CHILD | WS_VISIBLE | WS_GROUP, 240, 124, 59, 12
EDITTEXT IDC_M, 297, 122, 49, 12
CONTROL "FW Flow (lbs/hr):", -1, "STATIC", SS_LEFTNOWORDWRAP | WS_CHILD | WS_VISIBLE | WS_GROUP, 240, 136, 59, 12
EDITTEXT IDC_FWFLOW, 297, 134, 49, 12
CONTROL "Min:", -1, "STATIC", SS_LEFTNOWORDWRAP | WS_CHILD | WS_VISIBLE | WS_GROUP, 233, 160, 16, 12
CONTROL "Max:", -1, "STATIC", SS_LEFTNOWORDWRAP | WS_CHILD | WS_VISIBLE | WS_GROUP, 233, 172, 16, 12
CONTROL "Est.", -1, "STATIC", SS_LEFTNOWORDWRAP | WS_CHILD | WS_VISIBLE | WS_GROUP, 233, 184, 15, 9
CONTROL " BD (lb/hr)", -1, "STATIC", SS_LEFTNOWORDWRAP | WS_CHILD | WS_VISIBLE | WS_BORDER | WS_GROUP, 248, 150, 49, 10
EDITTEXT IDC_BDMIN, 248, 159, 49, 12
EDITTEXT IDC_BDMAX, 248, 171, 49, 12
EDITTEXT IDC_BD, 248, 183, 49, 12
LTEXT "FW Na (ppb)", -1, 297, 150, 49, 10, WS_BORDER | WS_GROUP
EDITTEXT IDC_MINFWNA, 297, 159, 49, 12
EDITTEXT IDC_MAXFWNA, 297, 171, 49, 12
EDITTEXT IDC_FWNA, 297, 183, 49, 12
CONTROL "Model Adaptive Compound Controller 4 SmartScan+ 102. Copyright (c) Nalco Labs, 1994. All rights reserved.", IDC_MESSAGELINE, "STATIC", SS_LEFTNOWORDWRAP | WS_CHILD | WS_VISIBLE | WS_BORDER | WS_GROUP, 1, 235, 348, 11
PUSHBUTTON "Boiler0", IDC_ENGINE0, 1, 217, 35, 14, WS_GROUP | WS_TABSTOP
PUSHBUTTON "Boiler1", IDC_ENGINE1, 36, 217, 35, 14
PUSHBUTTON "Boiler2", IDC_ENGINE2, 71, 217, 35, 14
PUSHBUTTON "Boiler3", IDC_ENGINE3, 106, 217, 35, 14
PUSHBUTTON "Boiler4", IDC_ENGINE4, 141, 217, 35, 14
PUSHBUTTON "Boiler5", IDC_ENGINE5, 176, 217, 35, 14
PUSHBUTTON "Boiler6", IDC_ENGINE6, 211, 217, 35, 14
PUSHBUTTON "Boiler7", IDC_ENGINE7, 246, 217, 35, 14
PUSHBUTTON "Boiler8", IDC_ENGINE8, 281, 217, 35, 14
PUSHBUTTON "Boiler9", IDC_ENGINE9, 316, 217, 35, 14
CONTROL "Point names: m0nh4ed,m0fwed,m0pH,m0PO4,m0bdtemp,m0cycide,m0cond,m0trial,m0Mtopf,_m0flag17", IDC_POINTNAMES, "STATIC", SS_LEFTNOWORDWRAP | WS_CHILD | WS_VISIBLE | WS_GROUP, 4, 204, 345, 8
PUSHBUTTON "Stop", IDC_STOP, 231, 4, 58, 14
PUSHBUTTON "Start", IDC_START, 289, 4, 59, 14
CHECKBOX "Simulate SSP", IDC_SIMULATESSP, 231, 20, 54, 14, BS_AUTOCHECKBOX | WS_TABSTOP
CHECKBOX "Local Inputs", IDC_LOCALINPUT, 295, 21, 53, 12, BS_AUTOCHECKBOX | WS_TABSTOP
PUSHBUTTON "Update", IDC_UPDATE, 231, 35, 39, 12
PUSHBUTTON "Undo", IDC_UNDO, 270, 35, 39, 12
PUSHBUTTON "Reinit", IDC_REINIT, 309, 35, 39, 12
GROUPBOX "Outputs to SmartScan+", IDC_GROUPBOX6, 231, 48, 117, 44, BS_GROUPBOX | WS_GROUP
LTEXT "Feed Rate A (gpd):", -1, 235, 59, 64, 12
```

```
LTEXT "", IDC_AFEED, 298, 59, 45, 10, WS_BORDER | WS_GROUP
LTEXT "Feed Rate B (gpd):", -1, 235, 68, 64, 12
LTEXT "", IDC_BFEED, 298, 68, 45, 10, WS_BORDER | WS_GROUP
LTEXT "Status Flags:", -1, 235, 79, 43, 8
LTEXT "", IDC_STATUSFLAGS, 292, 78, 51, 10, WS_BORDER | WS_GROUP
EDITTEXT IDC_FORECASTTIME, 231, 94, 17, 12
PUSHBUTTON "hr PO4/pH forecast", IDC_FORECAST, 248, 94, 66, 12
CHECKBOX "Logfile", IDC_LOGTOFILE, 316, 95, 32, 12, BS_AUTOCHECKBOX | WS_TABSTOP
CONTROL "", -1, "static", SS_BLACKFRAME | WS_CHILD | WS_VISIBLE, 128, 133, 11, 1
CONTROL "", -1, "static", SS_BLACKFRAME | WS_CHILD | WS_VISIBLE, 233, 192, 12, 1
CONTROL "", -1, "static", SS_BLACKFRAME | WS_CHILD | WS_VISIBLE | WS_BORDER, 11, 133, 55, 1
CONTROL "", -1, "static", SS_BLACKFRAME | WS_CHILD | WS_VISIBLE | WS_BORDER, 128, 173, 54, 1
CONTROL "Temperature (F):", -1, "STATIC", SS_LEFTNOWORDWRAP | WS_CHILD | WS_VISIBLE | WS_GROUP, 128, 165, 56, 8
GROUPBOX "Boiler pH", IDC_GROUPBOX4, 118, 109, 109, 91, BS_GROUPBOX
}

MACC4SSP_ICON ICON "macc4ssp.ico"
```

```c
/* macc4ssp.c: Model Adaptive Congruent Controller Engine for SmartScan Plus*/
/* version 1.0. Copyright (c) Betz Labs, 1994. All rights reserved. */

/* written by John Gunther, R&D Computer Applications Group, July, 1994 */
/* (extension 2760, Trevose office) */ include <windows.h>
include <string.h>
#include <time.h>
#include <stdio.h>
#include <stdlib.h>
#include <ctype.h>
#include <dos.h>
#include "scintdll.h"        /* SmartCard Interface Library */
#include "macc4.h"           /* Model Adaptive Congruent Controller, version 4*/
include "macc4ssp.h"        /* Identifiers for fields, other parameters */ define TESTING 0  /* determines the test pattern used in operator sim.*/ define WORKAROUND 0 /* used to workaround memory leak in SCIL version 1A1*/ if TESTING
define SCILERRORFRACTION 0.05 /* used during dev. to produce SCIL errors */
#else
#define SCILERRORFRACTION 0.0  /* no SCIL errors in production simulations*/
endif define ROOMTEMPERATUREDEGREESF 77.0
define UNDOINTERVAL 1.0  /* only give them 1 hour to undo */
#define M4SMODULENAME "MACC4SSP"
static HWND hmainwin = NULL;     /* handle to main (dialog) window */ define DOUBLEPRECISIONFORMAT "%.10g"    /* full precision doubles */
define FLOATPRECISIONFORMAT "%.6g"      /* full precision floats */
#define SHORTFLOATPRECISIONFORMAT "%.5g" /* helps squeeze stuff in sometimes */
#define MAXSTRING 100
define IGNORECHECKSUM -1  /* if checksum is set to this, it is ignored*/ define SIMHOURSPERREALSECOND 1.0
define SIMHOURSPEREVENT 24.0
#define SECONDSPERHOUR 3600
#define M4STIMERID 1
define DEFTIMERINTERVAL 3000    /* in milliseconds */ define NANINT -32767   /* undefined integer */
define NANFLT E_NAN    /* undefined floating point value (from macc4.h)*/
```

```
#define NANSTRING ""      /* string corresponding to undefined value */
#define NANBOOL -1         /* used with BOOLPLUS type to allow "undefined"*/
typedef enum boolplus { /* extends BOOL to include NANBOOL ("not a number") */
    BP_TRUE=TRUE, BP_FALSE=FALSE, BP_NANBOOL=NANBOOL,
} BOOLPLUS;

typedef struct simsspevent { BOOLPLUS update, undo, reinit; } SIMSSPEVENT;

SIMSSPEVENT simsspinputs[] =
{
#if TESTING
        {TRUE,  FALSE, FALSE},
        {FALSE, TRUE,  FALSE},
        {FALSE, FALSE, TRUE},
        {TRUE,  TRUE,  TRUE},
        {FALSE, TRUE,  TRUE},
        {TRUE,  FALSE, TRUE},
        {TRUE,  TRUE,  FALSE},
#endif
        {TRUE, FALSE, FALSE},
};

static SIMSSPEVENT nullevent = {FALSE, FALSE, FALSE};

#define MINENGINEID 0
#define DEFENGINEID 0
#define MAXENGINEID 9
typedef int M4SENGINEID;/* all reference to M4SENGINE objects is via this id */
typedef int M4SPARAMID; /* identifies a parameter used by the M4SENGINE    */
        /* (c.f. m4sparameters and/or macc4ssp.h for list of defined pids) */
typedef struct m4sengine { /*in memory representation of a MACC4SSP Engine */
    BOOL running;              /*is the engine running? */
    SCIError scierr;           /*1st SmartCard Interface Library error code seen */
    M4SPARAMID pidscierr;      /*identifier of parameter SCIL error involves*/
    BOOL actionsuptodate;      /*SSP action codes MACC4SSP maintains up-to-date?*/
    BOOL flagsuptodate;        /*SSP flags MACC4SSP maintains up-to-date?*/
    int checksum;              /* used to validate engine state I/O */
    BOOL badchecksum;          /* signals a corrupted INI file (invalid state)*/
    BOOL logtofile;            /* log actions to *.LOG file?*/
    BOOL simulatessp;          /* simulate SSP inputs? (for testing)*/
    BOOL localinput;           /* accept inputs locally?*/
    BOOL nh3enabled;           /* use an ammonia correction for pH's?*/
    double starttime;          /* (actual, real world) time at which run began */
    double lasteventtime;      /* time of last simulated operator input*/
    int eventid;               /* cursor into table of simulated operator inputs*/
    SIMSSPEVENT currentevent;  /* simulated or locally generated events*/
```

93

```c
        double fwflow;        /* feedwater flow--used to scale na leak */
        E_BOILER blr;         /* MACC4 controller as defined in macc4.h */
        }
M4SENGINE;
M4SENGINE m4e[MAXENGINEID+1];
static int currentengineid = DEFENGINEID;

#define xquote(x) #x
#define quote(x) xquote(x)    /* forces expansion of x before quoting it */
# define M_SAY(s) MessageBox(hmainwin,s,"Informational message",MB_OK)
# define M_BUGALERT(s) MessageBox(hmainwin,s,\
"MACC4SSP bug in file: " quote(__FILE__) " at line: " quote(__LINE__),MB_OK)
#define M_ASSERT(cond) \
if (!(cond)) MessageBox(hmainwin, "Failed assertion: " #cond,\
"Assertion Failure in File: " quote(__FILE__) " at Line: " quote(__LINE__),\
MB_ICONHAND|MB_OK)
#define M_M4SINFO(s) clearmarque(),marque(s)
#define M_M4SERROR(s) MessageBeep(0),clearmarque(),marque(s)
#define M_M4SERROR2(s) MessageBeep(0),MessageBeep(0),clearmarque(),marque(s)
#define M_M4SFATALERROR(s) \
MessageBox(hmainwin, s, "MACC4SSP fatal error--cannot continue.",\
MB_OK|MB_ICONEXCLAMATION)

/*
Initialization error message information. Index of array is integer
code as defined in the initstatus enum in macc4.h.
*/ struct initerror {char *msg; /* message to display for initstatus error*/
              M4SPARAMID field;} /*id of error related control to move to*/
initerr[] = {
    {"E_INITOK: Initialization OK", IDC_STOP},
    {"E_MISSING_T: required field t (time) has not been specified.", IDC_STOP},
    {"E_MISSING_FAMIN: required field famin has not been specified", IDC_FAMIN},
    {"E_MISSING_FAMAX: required field famax has not been specified", IDC_FAMAX},
    {"E_MISSING_FADEF: required field fadef has not been specified", IDC_FADEF},
    {"E_MISSING_PO4A: required field po4a has not been specified", IDC_PO4A},
    {"E_MISSING_RATIOA: required field ratioa has not been specified",
        IDC_RATIOA},
    {"E_MISSING_FBMIN: required field fbmin has not been specified",
        IDC_FBMIN},
    {"E_MISSING_FBMAX: required field fbmax has not been specified", IDC_FBMAX},
    {"E_MISSING_FBDEF: required field fbdef has not been specified", IDC_FBDEF},
    {"E_MISSING_PO4B: required field po4b has not been specified", IDC_PO4B},
    {"E_MISSING_RATIOB: required field ratiob has not been specified",
        IDC_RATIOB},
```

94

```
{"E_MISSING_PO4: required field po4 has not been specified", IDC_PO4},
{"E_MISSING_PH: required field ph has not been specified", IDC_PH},
{"E_MISSING_M: required field m (mass) has not been specified", IDC_M},
{"E_MISSING_BDTEMP: required field bdtemp has not been specified",
    IDC_BDTEMP},
{"E_MISSING_PO4SETPOINT: required field po4setpoint has not been specified",
    IDC_PO4SETPOINT},
    {"E_MISSING_MINPO4: required field minpo4 has not been specified",
        IDC_MINPO4},
    {"E_MISSING_MAXPO4: required field maxpo4 has not been specified",
        IDC_MAXPO4},
    {"E_MISSING_RATIOSETPOINT: neither phsetpoint nor napo4ratio were specified",
        IDC_PHSETPOINT},
{"E_BDMAX_LT_BDMIN: max blowdown rate, bdmax < min blowdown rate, bdmin",
    IDC_BDMIN},
{"E_NALEAKMAX_LT_NALEAKMIN: max Na leak, naleakmax < min Na leak, naleakmin",
    IDC_MINFWNA},
{"E_FAMAX_LE_FAMIN: max pump a flow, famax <= min pump a flow, famin",
    IDC_FAMIN},
{"E_FBMAX_LE_FBMIN: max pump b flow, fbmax <= min pump b flow, fbmin",
    IDC_FBMIN},
{"E_MINPO4_LT_MINMINPO4: lower boiler po4 control limit, minpo4 < 1 ppm",
    IDC_MINPO4},
{"E_MAXPO4_GT_MAXMAXPO4: upper boiler po4 control limit, maxpo4 > 100 ppm",
    IDC_MAXPO4},
{"E_PO4SETPOINT_LT_MINPO4: setpoint boiler po4 < lower control limit",
    IDC_PO4SETPOINT},
{"E_PO4SETPOINT_GT_MAXPO4: setpoint boiler po4 > upper control limit",
    IDC_PO4SETPOINT},
{"E_PO4A_LT_ZERO: pump a phosphate concentration < 0",
    IDC_PO4A},
{"E_PO4B_LT_ZERO: pump b phosphate concentration < 0",
    IDC_PO4B},
{"E_MINRATIO_LT_MINMINRATIO: lower Na/PO4 ratio control limit < 2.2",
    IDC_DPHSETPOINT},
{"E_MAXRATIO_GT_MAXMAXRATIO: upper Na/PO4 ratio control limit > 2.8",
    IDC_DPHSETPOINT},
{"E_RATIO_LT_MINRATIO: setpoint Na/PO4 ratio < lower control limit",
    IDC_DPHSETPOINT},
{"E_RATIO_GT_MAXRATIO: setpoint Na/PO4 ratio > upper control limit",
    IDC_DPHSETPOINT},
{"E_RATIOA_EQ_RATIOB: pump a Na/PO4 ratio = pump b Na/PO4 ratio",
    IDC_RATIOA},
{"E_MISSING_SPGA: required field spga (specific gravity) not specified",
    IDC_SPGA},
{"E_MISSING_SPGB: required field spgb (specific gravity) not specified",
    IDC_SPGB}
```

```
};

typedef enum controlsecuritylevel {
    NULL_LEVEL=0,              /* no security enforced on the control */
    MANAGERONLY_LEVEL=1,  /* access only for users who have entered password */
    OPERATORONLY_LEVEL=2,/* access only for users who have NOT entered password*/
} CONTROLSECURITYLEVEL;

typedef enum controlaccess {
    NULL_ACCESS=0,        /* unconditional access */
    STATIC_ACCESS=1,   /* control ONLY accessable when controller is stopped */
    DYNAMIC_ACCESS=2,  /* control ONLY accessable when controller is running */
    LOCAL_ACCESS=4,    /*if running, cntrl accessable only if local input checked
                          if stopped, cntrl accessable only if user is a manager */
    NH3_ACCESS=8       /* control ONLY accessible when nh3 is checked */
}
CONTROLACCESS;

typedef enum controltype {
    NULL_CONTROL,/*not a control, or a control not stored/restored to/from disk*/
    STOREDEDIT_CONTROL, /* edit control which is stored/restored to/from disk */
    STOREDCHECKBOX_CONTROL /* stored/restored to/from disk checkbox control */
}
CONTROLTYPE;

typedef struct m4sparam {
    int pid;
    char *name;
/* remaining fields only apply to parameters that are associated with
    one of the on-screen controls */
    double low;  /* for range checking of edit controls*/
    double high;
    CONTROLSECURITYLEVEL level;   /* who can access control ? */
    CONTROLACCESS access;         /* and under what conditions? */
    CONTROLTYPE type; /* stored text (edit ctrl), stored mode (checkbox)*/
} M4SPARAM;

#define SMALLNUMBER 1e-15

M4SPARAM m4sparameters[] = {
    /*misc.ids*/
{IDC_CURRENTENGINEID,"currentengineid",NANFLT,NANFLT,NULL_LEVEL,
    NULL_ACCESS,NULL_CONTROL},
{IDC_RUNNING,"running",NANFLT,NANFLT,NULL_LEVEL,NULL_ACCESS,NULL_CONTROL},
{IDC_FLAGSUPTODATE,"flagsuptodate",NANFLT,NANFLT,NULL_LEVEL,NULL_ACCESS,
    NULL_CONTROL},
```

{IDC_ACTIONSUPTODATE,"actionsuptodate",NANFLT,NANFLT,NULL_LEVEL,NULL_ACCESS,
   NULL_CONTROL},
{IDC_CHECKSUM,"checksum",NANFLT,NANFLT,NULL_LEVEL,NULL_ACCESS,NULL_CONTROL},
{IDC_LASTEVENTTIME,"lasteventtime",NANFLT,NANFLT,NULL_LEVEL,NULL_ACCESS,
   NULL_CONTROL},
{IDC_EVENTID,"eventid",NANFLT,NANFLT,NULL_LEVEL,NULL_ACCESS,NULL_CONTROL},
/*
   dialog box control ids (all parameters which are associated with a
   control must be placed between IDC_FIRSTCONTROL and IDC_LASTCONTROL)
*/
define IDC_FIRSTCONTROL IDC_FORECASTTIME
{IDC_FORECASTTIME,"forecasttime",0,999,NULL_LEVEL,DYNAMIC_ACCESS,
   STOREDEDIT_CONTROL}, /* limit to 999 so it fits in narrow 3 character field*/
{IDC_FORECAST,"forecast",NANFLT,NANFLT,NULL_LEVEL,DYNAMIC_ACCESS,
   NULL_CONTROL},
{IDC_PASSWORD,"password",NANFLT,NANFLT,OPERATORONLY_LEVEL,NULL_ACCESS,
   NULL_CONTROL},
{IDC_LOCKWINDOW,"lockwindow",NANFLT,NANFLT,MANAGERONLY_LEVEL,NULL_ACCESS,
   NULL_CONTROL},
{IDC_STARTTIME,"starttime",NANFLT,NANFLT,NULL_LEVEL,NULL_ACCESS,NULL_CONTROL},
{IDC_LOGTOFILE,"logtofile",NANFLT,NANFLT,MANAGERONLY_LEVEL,STATIC_ACCESS,
   STOREDCHECKBOX_CONTROL},
{IDC_SIMULATESSP,"simulatessp",NANFLT,NANFLT,MANAGERONLY_LEVEL,STATIC_ACCESS,
   STOREDCHECKBOX_CONTROL},
{IDC_LOCALINPUT,"localinput",NANFLT,NANFLT,MANAGERONLY_LEVEL,STATIC_ACCESS,
   STOREDCHECKBOX_CONTROL},
{IDC_MINFWNA,"minfwna",NANFLT,NANFLT,MANAGERONLY_LEVEL,STATIC_ACCESS,
   STOREDEDIT_CONTROL},
{IDC_MAXFWNA,"maxfwna",NANFLT,NANFLT,MANAGERONLY_LEVEL,STATIC_ACCESS,
   STOREDEDIT_CONTROL},
{IDC_FWFLOW,"fwflow",SMALLNUMBER,NANFLT,MANAGERONLY_LEVEL,STATIC_ACCESS,
   STOREDEDIT_CONTROL},
{IDC_BDMIN,"bdmin",SMALLNUMBER,NANFLT,MANAGERONLY_LEVEL,STATIC_ACCESS,
   STOREDEDIT_CONTROL},
{IDC_BDMAX,"bdmax",SMALLNUMBER,NANFLT,MANAGERONLY_LEVEL,STATIC_ACCESS,
   STOREDEDIT_CONTROL},
{IDC_M,"m",SMALLNUMBER,NANFLT,MANAGERONLY_LEVEL,STATIC_ACCESS,
   STOREDEDIT_CONTROL},
{IDC_DPHSETPOINT,"dphsetpoint",SMALLNUMBER,1.0,MANAGERONLY_LEVEL,STATIC_ACCESS,
   STOREDEDIT_CONTROL},
{IDC_PHSETPOINT,"phsetpoint",2,13,MANAGERONLY_LEVEL,STATIC_ACCESS,
   STOREDEDIT_CONTROL},
{IDC_DPH,"dph",SMALLNUMBER,1.0,MANAGERONLY_LEVEL,STATIC_ACCESS,
   STOREDEDIT_CONTROL},
{IDC_MAXPO4,"maxpo4",1.,1000.,MANAGERONLY_LEVEL,STATIC_ACCESS,

```
STOREDEDIT_CONTROL},
{IDC_MINPO4,"minpo4",1.,1000.,MANAGERONLY_LEVEL,STATIC_ACCESS,
  STOREDEDIT_CONTROL},
{IDC_PO4SETPOINT,"po4setpoint",1.,1000.,MANAGERONLY_LEVEL,STATIC_ACCESS,
  STOREDEDIT_CONTROL},
{IDC_DPO4,"dpo4",SMALLNUMBER,10.,MANAGERONLY_LEVEL,STATIC_ACCESS,
  STOREDEDIT_CONTROL},
{IDC_SPGA,"spga",SMALLNUMBER,NANFLT,MANAGERONLY_LEVEL,STATIC_ACCESS,
  STOREDEDIT_CONTROL},
{IDC_SPGB,"spgb",SMALLNUMBER,NANFLT,MANAGERONLY_LEVEL,STATIC_ACCESS,
  STOREDEDIT_CONTROL},
{IDC_PO4B,"po4b",0,100,MANAGERONLY_LEVEL,STATIC_ACCESS,
  STOREDEDIT_CONTROL},
{IDC_FBDEF,"fbdef",0,NANFLT,MANAGERONLY_LEVEL,STATIC_ACCESS,
  STOREDEDIT_CONTROL},
{IDC_FBMAX,"fbmax",0,NANFLT,MANAGERONLY_LEVEL,STATIC_ACCESS,
  STOREDEDIT_CONTROL},
{IDC_FBMIN,"fbmin",0,NANFLT,MANAGERONLY_LEVEL,STATIC_ACCESS,
  STOREDEDIT_CONTROL},
{IDC_RATIOB,"ratiob",0,NANFLT,MANAGERONLY_LEVEL,STATIC_ACCESS,
  STOREDEDIT_CONTROL},
{IDC_RATIOA,"ratioa",0,NANFLT,MANAGERONLY_LEVEL,STATIC_ACCESS,
  STOREDEDIT_CONTROL},
{IDC_PO4A,"po4a",0,100,MANAGERONLY_LEVEL,STATIC_ACCESS,
  STOREDEDIT_CONTROL},
{IDC_FADEF,"fadef",0,NANFLT,MANAGERONLY_LEVEL,STATIC_ACCESS,
  STOREDEDIT_CONTROL},
{IDC_FAMAX,"famax",0,NANFLT,MANAGERONLY_LEVEL,STATIC_ACCESS,
  STOREDEDIT_CONTROL},
{IDC_FAMIN,"famin",0,NANFLT,MANAGERONLY_LEVEL,STATIC_ACCESS,
  STOREDEDIT_CONTROL},
{IDC_MESSAGELINE,"messageline",NANFLT,NANFLT,NULL_LEVEL,NULL_ACCESS,
  NULL_CONTROL},
{IDC_NH3ENABLED,"nh3enabled",NANFLT,NANFLT,MANAGERONLY_LEVEL,STATIC_ACCESS,
  STOREDCHECKBOX_CONTROL},
{IDC_NH3TEXT,"nh3text",NANFLT,NANFLT,NULL_LEVEL,NH3_ACCESS,NULL_CONTROL},
{IDC_START,"START",NANFLT,NANFLT,MANAGERONLY_LEVEL,STATIC_ACCESS,
  NULL_CONTROL},
{IDC_STOP,"STOP",NANFLT,NANFLT,MANAGERONLY_LEVEL,DYNAMIC_ACCESS,
  NULL_CONTROL}, /* SSP point names (some also correspond to controls) */
/* (we use uppercase for SmartScan+ point names cause' SmartScan+ */
/* converts point names to uppercase)*/
```

```
{IDC_BDTEMP,"BDTEMP",32,212,NULL_LEVEL,LOCAL_ACCESS,
    STOREDEDIT_CONTROL},
{IDC_PO4,"PO4",SMALLNUMBER,1000.0,NULL_LEVEL,LOCAL_ACCESS,
    STOREDEDIT_CONTROL},
{IDC_NH3,"NH3",0.0,1000.0,NULL_LEVEL,LOCAL_ACCESS|NH3_ACCESS,
    STOREDEDIT_CONTROL},
{IDC_PH,"PH",1,14,NULL_LEVEL,LOCAL_ACCESS,
    STOREDEDIT_CONTROL},
{IDC_FWNA,"FWNA",NANFLT,NANFLT,MANAGERONLY_LEVEL,STATIC_ACCESS,
    STOREDEDIT_CONTROL},
{IDC_BD,"BD",SMALLNUMBER,NANFLT,MANAGERONLY_LEVEL,STATIC_ACCESS,
    STOREDEDIT_CONTROL},
{IDC_UPDATE,"UPDATE",NANFLT,NANFLT,NULL_LEVEL,LOCAL_ACCESS|DYNAMIC_ACCESS,
    NULL_CONTROL},
{IDC_REINIT,"REINIT",NANFLT,NANFLT,NULL_LEVEL,LOCAL_ACCESS|DYNAMIC_ACCESS,
    NULL_CONTROL},
{IDC_UNDO,"UNDO",NANFLT,NANFLT,NULL_LEVEL,LOCAL_ACCESS|DYNAMIC_ACCESS,
    NULL_CONTROL}, define IDC_LASTCONTROL IDC_UNDO

{IDC_AFEED,"AFEED",NANFLT,NANFLT,NULL_LEVEL,NULL_ACCESS,NULL_CONTROL},
{IDC_BFEED,"BFEED",NANFLT,NANFLT,NULL_LEVEL,NULL_ACCESS,NULL_CONTROL},
{IDC_RATIO,"RATIO",SMALLNUMBER,NANFLT,NULL_LEVEL,NULL_ACCESS,NULL_CONTROL},
{IDC_FLAG1,"FLAG1",NANFLT,NANFLT,NULL_LEVEL,NULL_ACCESS,NULL_CONTROL},
{IDC_FLAG2,"FLAG2",NANFLT,NANFLT,NULL_LEVEL,NULL_ACCESS,NULL_CONTROL},
{IDC_FLAG3,"FLAG3",NANFLT,NANFLT,NULL_LEVEL,NULL_ACCESS,NULL_CONTROL},
{IDC_FLAG4,"FLAG4",NANFLT,NANFLT,NULL_LEVEL,NULL_ACCESS,NULL_CONTROL},
{IDC_FLAG5,"FLAG5",NANFLT,NANFLT,NULL_LEVEL,NULL_ACCESS,NULL_CONTROL},
{IDC_FLAG6,"FLAG6",NANFLT,NANFLT,NULL_LEVEL,NULL_ACCESS,NULL_CONTROL},
{IDC_FLAG7,"FLAG7",NANFLT,NANFLT,NULL_LEVEL,NULL_ACCESS,NULL_CONTROL},
{IDC_FLAG8,"FLAG8",NANFLT,NANFLT,NULL_LEVEL,NULL_ACCESS,NULL_CONTROL},
{IDC_FLAG9,"FLAG9",NANFLT,NANFLT,NULL_LEVEL,NULL_ACCESS,NULL_CONTROL},
{IDC_FLAG10,"FLAG10",NANFLT,NANFLT,NULL_LEVEL,NULL_ACCESS,NULL_CONTROL},
{IDC_FLAG11,"FLAG11",NANFLT,NANFLT,NULL_LEVEL,NULL_ACCESS,NULL_CONTROL},
{IDC_FLAG12,"FLAG12",NANFLT,NANFLT,NULL_LEVEL,NULL_ACCESS,NULL_CONTROL},

/* Just E_BOILER fields */
{IDC_T,"t",NANFLT,NANFLT,NULL_LEVEL,NULL_ACCESS,NULL_CONTROL},
{IDC_NAPO4RATIO,"napo4ratio",NANFLT,NANFLT,NULL_LEVEL,NULL_ACCESS,
    NULL_CONTROL},
{IDC_MINNAPO4RATIO,"minnapo4ratio",NANFLT,NANFLT,NULL_LEVEL,NULL_ACCESS,
    NULL_CONTROL},
{IDC_MAXNAPO4RATIO,"maxnapo4ratio",NANFLT,NANFLT,NULL_LEVEL,NULL_ACCESS,
    NULL_CONTROL},
```

{IDC_MAX_SAMPLE_INTERVAL,"max_sample_interval",NANFLT,NANFLT,
  NULL_LEVEL,NULL_ACCESS,NULL_CONTROL},
{IDC_MAX_OUTOFBOX_ADJUSTMENT,"max_outofbox_adjustment",NANFLT,NANFLT,
  NULL_LEVEL,NULL_ACCESS,NULL_CONTROL},
{IDC_MAX_RELATIVE_ERROR,"max_relative_error",NANFLT,NANFLT, NULL_LEVEL,
  NULL_ACCESS,NULL_CONTROL},
{IDC_BEPS,"beps",NANFLT,NANFLT,NULL_LEVEL,NULL_ACCESS,NULL_CONTROL},
{IDC_FDT,"fdt",NANFLT,NANFLT,NULL_LEVEL,NULL_ACCESS,NULL_CONTROL},
{IDC_LASTT,"lastt",NANFLT,NANFLT,NULL_LEVEL,NULL_ACCESS,NULL_CONTROL},
{IDC_LASTBDTEMP,"lastbdtemp",NANFLT,NANFLT,NULL_LEVEL,NULL_ACCESS,
  NULL_CONTROL},
{IDC_LASTPO4,"lastpo4",NANFLT,NANFLT,NULL_LEVEL,NULL_ACCESS,NULL_CONTROL},
{IDC_LASTNH3,"lastnh3",NANFLT,NANFLT,NULL_LEVEL,NULL_ACCESS,NULL_CONTROL},
{IDC_LASTPH,"lastph",NANFLT,NANFLT,NULL_LEVEL,NULL_ACCESS,NULL_CONTROL},
{IDC_B4LASTT,"b4lastt",NANFLT,NANFLT,NULL_LEVEL,NULL_ACCESS,NULL_CONTROL},
{IDC_B4LASTBDTEMP,"b4lastbdtemp",NANFLT,NANFLT,NULL_LEVEL,NULL_ACCESS,
  NULL_CONTROL},
{IDC_B4LASTPO4,"b4lastpo4",NANFLT,NANFLT,NULL_LEVEL,NULL_ACCESS,NULL_CONTROL},
{IDC_B4LASTNH3,"b4lastnh3",NANFLT,NANFLT,NULL_LEVEL,NULL_ACCESS,NULL_CONTROL},
{IDC_B4LASTPH,"b4lastph",NANFLT,NANFLT,NULL_LEVEL,NULL_ACCESS,NULL_CONTROL},
{IDC_LASTBD,"lastbd",NANFLT,NANFLT,NULL_LEVEL,NULL_ACCESS,NULL_CONTROL},
{IDC_LASTL,"lastl",NANFLT,NANFLT,NULL_LEVEL,NULL_ACCESS,NULL_CONTROL},
{IDC_DT1,"dt1",NANFLT,NANFLT,NULL_LEVEL,NULL_ACCESS,NULL_CONTROL},
{IDC_DT2,"dt2",NANFLT,NANFLT,NULL_LEVEL,NULL_ACCESS,NULL_CONTROL},
{IDC_FA1,"fa1",NANFLT,NANFLT,NULL_LEVEL,NULL_ACCESS,NULL_CONTROL},
{IDC_FA2,"fa2",NANFLT,NANFLT,NULL_LEVEL,NULL_ACCESS,NULL_CONTROL},
{IDC_FA3,"fa3",NANFLT,NANFLT,NULL_LEVEL,NULL_ACCESS,NULL_CONTROL},
{IDC_FB1,"fb1",NANFLT,NANFLT,NULL_LEVEL,NULL_ACCESS,NULL_CONTROL},
{IDC_FB2,"fb2",NANFLT,NANFLT,NULL_LEVEL,NULL_ACCESS,NULL_CONTROL},
{IDC_FB3,"fb3",NANFLT,NANFLT,NULL_LEVEL,NULL_ACCESS,NULL_CONTROL},
{IDC_LASTDT1,"lastdt1",NANFLT,NANFLT,NULL_LEVEL,NULL_ACCESS,NULL_CONTROL},
{IDC_LASTDT2,"lastdt2",NANFLT,NANFLT,NULL_LEVEL,NULL_ACCESS,NULL_CONTROL},
{IDC_LASTFA1,"lastfa1",NANFLT,NANFLT,NULL_LEVEL,NULL_ACCESS,NULL_CONTROL},
{IDC_LASTFA2,"lastfa2",NANFLT,NANFLT,NULL_LEVEL,NULL_ACCESS,NULL_CONTROL},
{IDC_LASTFA3,"lastfa3",NANFLT,NANFLT,NULL_LEVEL,NULL_ACCESS,NULL_CONTROL},
{IDC_LASTFB1,"lastfb1",NANFLT,NANFLT,NULL_LEVEL,NULL_ACCESS,NULL_CONTROL},
{IDC_LASTFB2,"lastfb2",NANFLT,NANFLT,NULL_LEVEL,NULL_ACCESS,NULL_CONTROL},
{IDC_LASTFB3,"lastfb3",NANFLT,NANFLT,NULL_LEVEL,NULL_ACCESS,NULL_CONTROL},
{IDC_UPDATESTATUS,"updatestatus",NANFLT,NANFLT,NULL_LEVEL,NULL_ACCESS,
  NULL_CONTROL},
{IDC_LASTUPDATESTATUS,"lastupdatestatus",NANFLT,NANFLT,NULL_LEVEL,
  NULL_ACCESS,NULL_CONTROL},
{IDC_INITSTATUS,"initstatus",NANFLT,NANFLT,NULL_LEVEL,NULL_ACCESS,
  NULL_CONTROL},

100

```
{IDC_UNDOABLE,"undoable",NANFLT,NANFLT,NULL_LEVEL,NULL_ACCESS,NULL_CONTROL},
{IDC_LAUNCH,"LAUNCH",NANFLT,NANFLT,NULL_LEVEL,NULL_ACCESS,NULL_CONTROL},
{IDC_CLOSE,"CLOSE",NANFLT,NANFLT,NULL_LEVEL,NULL_ACCESS,NULL_CONTROL},
{NANINT,"NANINT",NANFLT,NANFLT,NULL_LEVEL,NULL_ACCESS,NULL_CONTROL},
};

/* pid2param: returns the parameter struct given the parameter id */
M4SPARAM *pid2param(M4SPARAMID pid) {
    int i = 0;
    for (i = 0; i < sizeof(m4sparameters)/sizeof(m4sparameters[0]); i++)
        if (m4sparameters[i].pid == pid) return(&m4sparameters[i]);
    M_BUGALERT("Bad parameter id.");
    return(&m4sparameters[i-1]);
}

/* pid2name: returns name given the pid */
char *pid2name(M4SPARAMID pid) {
    return(pid2param(pid)->name);
}
/* pid2low: return low field*/
double pid2low(M4SPARAMID pid) {
    return(pid2param(pid)->low);
}
/* pid2low: return high field*/
double pid2high(M4SPARAMID pid) {
    return(pid2param(pid)->high);
}

/* compressexponent: replaces first e0, e+0, or e-0 with e, e+, or e- */
/* Note: the extra 0 in numbers like 1e-9 introduced by sprintf's 1-09
   encoding can be a problem (it doesn't fit into the field anymore)
   So we replace e0*, e-0*, and e+0* with e*, e-*, and e+* */
char *compressexponent(char *numstring) {
    char *e = strpbrk(numstring, "eE");
    if (NULL == e)              /* no e or E in the string--leave as is */
        ;
    else if ('0' == e[1] && e[2] != '\0')    /* for example, e09 */
        lstrcpy(e+1, e+2);
    else if (('-' == e[1] || '+' == e[1]) &&
             ('0' == e[2] && e[3] != '\0') )  /* for example, e-09*/
        lstrcpy(e+2, e+3);
    return (numstring);
```

```
}

/*encodenumber: convert a number to a character string */ char *encodenumber(double x, const char *fmt) {
    static char encodeddouble[MAXSTRING+1];
    if (x == NANFLT)
       lstrcpy(encodeddouble, NANSTRING);
    else {
       sprintf(encodeddouble, fmt, x);
       compressexponent(encodeddouble);
    }
    return(encodeddouble);
}

/*encodedouble: convert a double--with full precision--to a character string */ char *encodedouble(double x) {
       return(encodenumber(x,DOUBLEPRECISIONFORMAT));
}

/* decodedouble: convert a character string to a double */ double decodedouble(char *s) {
   return ( (lstrcmp(s,NANSTRING) == 0) ? NANFLT : atof(s) );
}

/*encodefloat: convert a double to a full float precision character string */ char *encodefloat(double x) {
       return(encodenumber(x,FLOATPRECISIONFORMAT));
}

/*encodeshortfloat: convert double to less than full float precision string*/ char *encodeshortfloat(double x) {
       return(encodenumber(x,SHORTFLOATPRECISIONFORMAT));
}

/*encodeint: convert an integer to a character string */ char *encodeint(int i) {
   static char encodedint[MAXSTRING+1];
   if (NANINT == i)
     lstrcpy(encodedint,NANSTRING);
   else
```

```c
        sprintf(encodedint, "%i", i);
    return(encodedint);
}

/*decodeint: convert a character string to an integer */ int decodeint(char *s) {
    return( (lstrcmp(s, NANSTRING) == 0) ? NANINT : atoi(s) );
} char *rangeerror(M4SPARAMID pid) {
    static char rangeerrortext[MAXSTRING+1];
    M4SPARAM *param = pid2param(pid);

sprintf(rangeerrortext,
"%s must obey: %s%s", param->name,
        encodefloat(param->low), (param->low == NANFLT) ? "" : " <= ");

sprintf(rangeerrortext + lstrlen(rangeerrortext),
            "%s%s%s -- entry cleared.", param->name,
            (param->high == NANFLT) ? "" : " <= ", encodefloat(param->high));

return(rangeerrortext);
}

/* timeinhours: returns time in hours since Jan 1, 1970 */ double timeinhours(void) {
    return ( ((double) time(NULL))/SECONDSPERHOUR );
}

/* m4stimeinhours: returns the time seen (simulated or real) by engine */ double m4stimeinhours(M4SENGINEID eid) {
    return (!m4e[eid].simulatessp ?
                timeinhours() : (m4e[eid].starttime +
    (SIMHOURSPERREALSECOND*SECONDSPERHOUR*(timeinhours()-m4e[eid].starttime))));
}

/* m4sdatetime: given hours since Jan 1, 1970, returns datetime string */ char *m4sdatetime(double m4stime) {
    static char datetime[MAXSTRING+1];
    time_t t = (time_t) (m4stime * SECONDSPERHOUR); /* convert to C time format*/
    strftime(datetime,MAXSTRING,"%d-%b-%Y %X", localtime(&t));
    return(datetime);
```

}

```c
/* begin: code to perform conversions from macc4.c module's internal
   moles/hr sodium leak units to the feedwater (lbs/hr) plus feedwater Na (ppb)
   values that macc4ssp presents to the user */ define MW_NA 22.99   /* molecular weight of Na */ double lb2kg(double lb) { return((NANFLT == lb) ? NANFLT : (lb*0.45359)); }
double kg2lb(double kg) { return((NANFLT == kg) ? NANFLT : (kg/0.45359)); } double ppb2molesperkg(double ppb, double mw) {
    return ((ppb == NANFLT) ? NANFLT : (ppb*1.0e-6/mw));
} double molesperkg2ppb(double mpk, double mw) {
    return ((mpk == NANFLT) ? NANFLT : (mpk*1.0e+6*mw));
}
/* nanmult: NaN aware multiplication */
double nanmult(double x1, double x2) {
    return ((x1==NANFLT || x2==NANFLT) ? NANFLT : (x1*x2));
}
/* nandiv: NaN aware division */
double nandiv(double x1, double x2) {
    return ((x1==NANFLT || x2==NANFLT || x2==0.0) ? NANFLT : (x1/x2));
}
/* naleak2fwna: converts the Na leak units (moles/hr) used by macc4.c
   to feedwater Na (ppb) used by macc4ssp.c's user interface.
   feed water flow in lbs/hr.*/ double naleak2fwna(double naleak, double fwflow) {
    return(molesperkg2ppb(nandiv(naleak,lb2kg(fwflow)), MW_NA));
}

/* fwna2naleak: inverse of naleak2fwna (see above) */ double fwna2naleak(double fwna, double fwflow) {
    return(nanmult(ppb2molesperkg(fwna, MW_NA), lb2kg(fwflow)));
}

/*end: code to perform unit conversions */

/*fixnanint: defaulting for undefined ints */ int fixnanint(int i, int fornan) {
    return (i==NANINT ? fornan : i);
```

```c
}
double fixnandbl(double x, double fornan) {
   return (x==NANFLT ? fornan : x);
}

/* m4spath: MACC4SSP path is the directory in which the EXE is located */
/* the trailing \ is included in this path ( e.g. C:\MACC4SSP\ ) */ char *m4spath(void) {
   static char path[2*MAXSTRING+1];
   int len =
      GetModuleFileName(GetModuleHandle(M4SMODULENAME), path, 2*MAXSTRING);

for (len--; len >= 0 && path[len]!='\\'; len--) /* zap name.ext part*/
      path[len]='\0';

return(path);

}

/* ctrl2s: returns the string associated with a control (or window) */ char *ctrl2s(HWND hCtrl) {
   static char s[MAXSTRING+1];
   GetWindowText(hCtrl, s, MAXSTRING);
   return(s);
}

/* s2ctrl: copies text to the given control */ void s2ctrl(HWND hCtrl, char *s) {
   SetWindowText(hCtrl, s);
} static char marquebuf[2*MAXSTRING+1];  /* stores scrolling marque */
/* clearmarque: clears the marque */
void clearmarque(void) {
   lstrcpy(marquebuf,"");
}

/* marque: uses message line as a scrolling marque */ void marque(char *s) {
   static BOOL firsttime = TRUE;
```

```
    if (firsttime) {
       clearmarque();
       firsttime = FALSE;
    }
    lstrcat(marquebuf, s);                /* add new string to end of old one */
    if (lstrlen(marquebuf) > MAXSTRING) /*destroy older part of marque*/
       lstrcpy(marquebuf, marquebuf+lstrlen(marquebuf)-MAXSTRING);
    s2ctrl(GetDlgItem(hmainwin, IDC_MESSAGELINE),marquebuf);
    UpdateWindow(GetDlgItem(hmainwin, IDC_MESSAGELINE));
}

/* nameprefix: returns the macc4 prefix associated with a given engineid */ char *nameprefix(M4SENGINEID eid) {
    static char prefix[MAXSTRING+1];
    sprintf(prefix, "M%i", eid);
    return(prefix);
}

/* inifile: returns the name of the engine's initialization file */ char *inifile(M4SENGINEID eid) {
    return(lstrcat(lstrcat(m4spath(),nameprefix(eid)),".INI"));
}

/*m4spointname: SSP point name for engineid/paramid pair */ char *m4spointname(M4SENGINEID eid, M4SPARAMID pid) {
    static char pointname[MAXSTRING+1];
    lstrcpy(pointname, nameprefix(eid));
    return(lstrcat(pointname,pid2name(pid)));
}

/* updatechecksum: simple hash to enforce I/O consistency*/ void updatechecksum(M4SENGINEID eid, M4SPARAMID pid, char *s) {
    if (pid != IDC_CHECKSUM)
       for (; *s; s++) if (isdigit(*s)) m4e[eid].checksum += (*s - '0' + 1);
}

/* ini2s: reads a string from an initialization file. */ char *ini2s(M4SENGINEID eid,  M4SPARAMID pid) {
    static char s[MAXSTRING+1];
    GetPrivateProfileString( M4SMODULENAME, pid2name(pid),
```

106

```c
                                          NANSTRING, s, MAXSTRING, inifile(eid));
    updatechecksum(eid, pid, s);
    return(s);
}

/* s2ini: writes a string to an initialization file */ void s2ini(M4SENGINEID eid, M4SPARAMID pid, char *s) {
    if (!WritePrivateProfileString(M4SMODULENAME,pid2name(pid),s,inifile(eid)))
        M_M4SERROR("Error writing to initialization file.");
    updatechecksum(eid, pid, s);
}

/* ctrl2ini: writes contents of a control to associated INI file keyword */ void ctrl2ini(M4SENGINEID eid, M4SPARAMID pid, HWND hCtrl) {
    s2ini(eid, pid, ctrl2s(hCtrl));
}

/* ini2ctrl: reads associated ini file keyword into a control */ void ini2ctrl(HWND hCtrl, int eid, int pid) {
    s2ctrl(hCtrl, ini2s(eid,pid));
} void dbl2ini(M4SENGINEID eid, M4SPARAMID pid, double x) {
    s2ini(eid,pid,encodedouble(x));
}

/* ini2dbl: reads associated ini file keyword into a memory */ double ini2dbl(M4SENGINEID eid, M4SPARAMID pid) {
    return(decodedouble(ini2s(eid,pid)));
}

/* int2ini: writes contents of field to associated ini file keyword */ void int2ini(M4SENGINEID eid, M4SPARAMID pid, int i) {
    s2ini(eid, pid, encodeint(i));
}

/* ini2int: reads associated ini file keyword into a memory */ int ini2int(M4SENGINEID eid, M4SPARAMID  pid) {
```

```
    return(decodeint(ini2s(eid,pid)));
}

/*pointnames: returns name of points string */
char *pointnames(M4SENGINEID eid) {
    const char *pointsprefix = "Points: ";
    static char pointnamebuf[2*MAXSTRING+1];
    if (m4e[eid].localinput)
        sprintf(pointnamebuf,
"%sm%i + (afeed,bfeed,flag7,flag12)", pointsprefix, eid);
    else {
        sprintf(pointnamebuf,
"%sm%i + (afeed,bfeed,ph,po4,%sbdtemp,%supdate,undo,reinit,flag1,...,flag12)",
        pointsprefix, eid, m4e[eid].nh3enabled ? "nh3," : "",
                           m4e[eid].localinput ? "" : "bd,fwna,ratio,");
    }
    return(pointnamebuf);
}
/*getcheckboxstate: TRUE if checkbox checked, else FLASE */
BOOL getcheckboxstate(HWND hcheckboxctrl) {
    return(SendMessage(hcheckboxctrl, BM_GETCHECK, 0, 0) ? TRUE : FALSE);
}
/* setcheckboxstate: checks or unchecks a checkbox */
void setcheckboxstate(HWND hcheckboxctrl, BOOL checked) {
    SendMessage(hcheckboxctrl, BM_SETCHECK, checked, 0);
}

/* ini2dlg: loads all fields from the ini file into dialog box (main window) */
/*
    checkboxes, which indicated controller modes, are loaded into memory
    as well as into the form--this makes modes easily available (without
    disk access) later on.
*/ void ini2dlg(HWND hDlg, int eid) {
    M4SPARAM *currentctrl = pid2param(IDC_FIRSTCONTROL);
    M4SPARAM *lastctrl    = pid2param(IDC_LASTCONTROL);

#define M_INI2CHECKBOX(wheretostore,pid,default) \
    wheretostore = fixnanint(ini2int(eid,pid),default), \
    setcheckboxstate(GetDlgItem(hDlg, pid), wheretostore)

M_INI2CHECKBOX(m4e[eid].logtofile,   IDC_LOGTOFILE,   TRUE);
    M_INI2CHECKBOX(m4e[eid].simulatessp, IDC_SIMULATESSP, FALSE);
```

```
M_INI2CHECKBOX(m4e[eid].localinput,  IDC_LOCALINPUT,  FALSE);
M_INI2CHECKBOX(m4e[eid].nh3enabled,  IDC_NH3ENABLED,  FALSE);
/*make point names on form match mode of engine just loaded into form:*/
s2ctrl(GetDlgItem(hDlg, IDC_POINTNAMES), pointnames(eid));

for ( ; currentctrl <= lastctrl; currentctrl++) /*load form's edit controls*/
    if (STOREDEDIT_CONTROL == currentctrl->type)  /* with this engine's info */
        ini2ctrl(GetDlgItem(hDlg, currentctrl->pid), eid, currentctrl->pid);

}

/*
    constraininputs: constrains inputs to the control based on both
    the kinds of users who are allowed to access it as well as the
    conditions under which access to that control is allowed. This
    routine either enables or disables each control accordingly.
*/ void constraininputs(HWND hDlg, M4SENGINEID eid, BOOL windowlocked) {
    M4SPARAM *currentctrl = pid2param(IDC_FIRSTCONTROL);
    M4SPARAM *lastctrl    = pid2param(IDC_LASTCONTROL);
    BOOL localinput       = m4e[eid].localinput;
    BOOL running          = m4e[eid].running;
    BOOL nh3enabled       = m4e[eid].nh3enabled;
    BOOL userisamanager   = !windowlocked;

for ( ; currentctrl <= lastctrl; currentctrl++) {
        BOOL manageronlyctrl = MANAGERONLY_LEVEL & currentctrl->level;
```

109

```
BOOL operatoronlyctrl = OPERATORONLY_LEVEL & currentctrl->level;
BOOL staticctrl       = STATIC_ACCESS      & currentctrl->access;
BOOL dynamicctrl      = DYNAMIC_ACCESS     & currentctrl->access;
BOOL localctrl        = LOCAL_ACCESS       & currentctrl->access;
BOOL nh3ctrl          = NH3_ACCESS         & currentctrl->access;

BOOL enablectrl = TRUE;   /* enabled until proven otherwise */

/* Decide if control is enabled by a process of elimination: consider,
   in turn, each condition which could require that the control be disabled*/ if (manageronlyctrl && !userisamanager)
        enablectrl = FALSE;
    else if (operatoronlyctrl && userisamanager) /* password prompt */
        enablectrl = FALSE;    /*(managers have already entered the password)*/
    else if (nh3ctrl && !nh3enabled)
        enablectrl = FALSE;
    else if (staticctrl && running)
        enablectrl = FALSE;
    else if (dynamicctrl && !running)
        enablectrl = FALSE;
    else if (localctrl && running && !localinput)
        enablectrl = FALSE;
    else if (localctrl && !running && !userisamanager)
        enablectrl = FALSE;
/* else, since there are no objections from the authorities, control enabled*/

EnableWindow(GetDlgItem(hDlg, currentctrl->pid), enablectrl);

}
}

/* ini2engine: loads all parameters from ini file into memory */
/* returns badchecksum: TRUE implies a bad check sum/corrupted file*/

BOOL ini2engine(M4SENGINEID eid) {
    int oldchecksum = ini2int(eid, IDC_CHECKSUM);

m4e[eid].blr.po4    = ini2dbl( eid, IDC_PO4 );
    m4e[eid].blr.ph     = ini2dbl( eid, IDC_PH );
    m4e[eid].blr.bdtemp = ini2dbl( eid, IDC_BDTEMP );
    m4e[eid].blr.nh3    = ini2dbl( eid, IDC_NH3 );

m4e[eid].lasteventtime = ini2int ( eid, IDC_LASTEVENTTIME);
    m4e[eid].eventid       = ini2int ( eid, IDC_EVENTID);
```

110

```
m4e[eid].checksum = 0;   /* we don't include first few params in checksum */
                         /* cause they can legitimately change */ m4e[eid].starttime     = ini2dbl ( eid, IDC_STARTTIME);
m4e[eid].running       = fixnanint(ini2int ( eid, IDC_RUNNING),FALSE);
m4e[eid].logtofile     = fixnanint(ini2int ( eid, IDC_LOGTOFILE), TRUE);
m4e[eid].blr.t         = ini2dbl( eid, IDC_T );
m4e[eid].blr.famin     = ini2dbl( eid, IDC_FAMIN );
m4e[eid].blr.famax     = ini2dbl( eid, IDC_FAMAX );
m4e[eid].blr.fadef     = ini2dbl( eid, IDC_FADEF );
m4e[eid].blr.po4a      = ini2dbl( eid, IDC_PO4A );
m4e[eid].blr.ratioa    = ini2dbl( eid, IDC_RATIOA );
m4e[eid].blr.spga      = ini2dbl( eid, IDC_SPGA );
m4e[eid].blr.fbmin     = ini2dbl( eid, IDC_FBMIN );
m4e[eid].blr.fbmax     = ini2dbl( eid, IDC_FBMAX );
m4e[eid].blr.fbdef     = ini2dbl( eid, IDC_FBDEF );
m4e[eid].blr.po4b      = ini2dbl( eid, IDC_PO4B );
m4e[eid].blr.ratiob    = ini2dbl( eid, IDC_RATIOB );
m4e[eid].blr.spgb      = ini2dbl( eid, IDC_SPGB );
m4e[eid].blr.m         = ini2dbl( eid, IDC_M );
m4e[eid].blr.dpo4      = ini2dbl( eid, IDC_DPO4 );
m4e[eid].blr.po4setpoint = ini2dbl( eid, IDC_PO4SETPOINT );
m4e[eid].blr.minpo4    = ini2dbl( eid, IDC_MINPO4 );
m4e[eid].blr.maxpo4    = ini2dbl( eid, IDC_MAXPO4 );
m4e[eid].blr.dph       = ini2dbl( eid, IDC_DPH );
m4e[eid].blr.phsetpoint = ini2dbl( eid, IDC_PHSETPOINT );
m4e[eid].blr.dphsetpoint = ini2dbl( eid, IDC_DPHSETPOINT );
m4e[eid].blr.napo4ratio = ini2dbl( eid, IDC_NAPO4RATIO );
m4e[eid].blr.minnapo4ratio = ini2dbl( eid, IDC_MINNAPO4RATIO );
m4e[eid].blr.maxnapo4ratio = ini2dbl( eid, IDC_MAXNAPO4RATIO );
m4e[eid].blr.max_sample_interval = ini2dbl( eid, IDC_MAX_SAMPLE_INTERVAL );
m4e[eid].blr.max_outofbox_adjustment =
    ini2dbl( eid, IDC_MAX_OUTOFBOX_ADJUSTMENT );
m4e[eid].blr.max_relative_error = ini2dbl( eid, IDC_MAX_RELATIVE_ERROR );
m4e[eid].blr.beps      = ini2dbl( eid, IDC_BEPS );
m4e[eid].blr.bdmin     = ini2dbl( eid, IDC_BDMIN );
m4e[eid].blr.bdmax     = ini2dbl( eid, IDC_BDMAX );
m4e[eid].fwflow        = ini2dbl( eid, IDC_FWFLOW);
m4e[eid].blr.naleakmin = fwna2naleak(ini2dbl( eid, IDC_MINFWNA ),
                                      m4e[eid].fwflow);
m4e[eid].blr.naleakmax = fwna2naleak(ini2dbl( eid, IDC_MAXFWNA ),
                                      m4e[eid].fwflow);
m4e[eid].blr.l         = fwna2naleak(ini2dbl( eid, IDC_FWNA),
                                      m4e[eid].fwflow);
m4e[eid].blr.fdt       = ini2dbl( eid, IDC_FDT );
```

111

```
m4e[eid].blr.lastt = ini2dbl( eid, IDC_LASTT );
m4e[eid].blr.lastbdtemp = ini2dbl( eid, IDC_LASTBDTEMP );
m4e[eid].blr.lastpo4 = ini2dbl( eid, IDC_LASTPO4 );
m4e[eid].blr.lastnh3 = ini2dbl( eid, IDC_LASTNH3 );
m4e[eid].blr.lastph = ini2dbl( eid, IDC_LASTPH );
m4e[eid].blr.b4lastt = ini2dbl( eid, IDC_B4LASTT );
m4e[eid].blr.b4lastbdtemp = ini2dbl( eid, IDC_B4LASTBDTEMP );
m4e[eid].blr.b4lastpo4 = ini2dbl( eid, IDC_B4LASTPO4 );
m4e[eid].blr.b4lastnh3 = ini2dbl( eid, IDC_B4LASTNH3 );
m4e[eid].blr.b4lastph = ini2dbl( eid, IDC_B4LASTPH );
m4e[eid].blr.bd = ini2dbl( eid, IDC_BD );
m4e[eid].blr.lastl = ini2dbl( eid, IDC_LASTL );
m4e[eid].blr.lastbd = ini2dbl( eid, IDC_LASTBD );
m4e[eid].blr.dt[0] = ini2dbl( eid, IDC_DT1 );
m4e[eid].blr.dt[1] = ini2dbl( eid, IDC_DT2 );
m4e[eid].blr.fb[0] = ini2dbl( eid, IDC_FB1 );
m4e[eid].blr.fb[1] = ini2dbl( eid, IDC_FB2 );
m4e[eid].blr.fb[2] = ini2dbl( eid, IDC_FB3 );
m4e[eid].blr.fa[0] = ini2dbl( eid, IDC_FA1 );
m4e[eid].blr.fa[1] = ini2dbl( eid, IDC_FA2 );
m4e[eid].blr.fa[2] = ini2dbl( eid, IDC_FA3 );
m4e[eid].blr.lastdt[0] = ini2dbl( eid, IDC_LASTDT1 );
m4e[eid].blr.lastdt[1] = ini2dbl( eid, IDC_LASTDT2 );
m4e[eid].blr.lastfa[0] = ini2dbl( eid, IDC_LASTFA1 );
m4e[eid].blr.lastfa[1] = ini2dbl( eid, IDC_LASTFA2 );
m4e[eid].blr.lastfa[2] = ini2dbl( eid, IDC_LASTFA3 );
m4e[eid].blr.lastfb[0] = ini2dbl( eid, IDC_LASTFB1 );
m4e[eid].blr.lastfb[1] = ini2dbl( eid, IDC_LASTFB2 );
m4e[eid].blr.lastfb[2] = ini2dbl( eid, IDC_LASTFB3 );
m4e[eid].blr.updatestatus =
    fixnanint(ini2int( eid,IDC_UPDATESTATUS),E_UPDATEOK);
m4e[eid].blr.lastupdatestatus =
    fixnanint(ini2int( eid, IDC_LASTUPDATESTATUS ), E_UPDATEOK);
m4e[eid].blr.initstatus =fixnanint(ini2int( eid, IDC_INITSTATUS),!E_INITOK);
m4e[eid].blr.undoable = fixnanint(ini2int( eid, IDC_UNDOABLE), FALSE);
m4e[eid].simulatessp = fixnanint(ini2int ( eid, IDC_SIMULATESSP),FALSE);
m4e[eid].localinput = fixnanint(ini2int ( eid, IDC_LOCALINPUT),FALSE);
m4e[eid].nh3enabled = fixnanint(ini2int ( eid, IDC_NH3ENABLED),FALSE);
return (m4e[eid].badchecksum =
    (m4e[eid].running &&              /* ignore if engine not running or */
    oldchecksum != IGNORECHECKSUM &&  /* if ignore checksum is flagged */
    oldchecksum != m4e[eid].checksum));
}
```

```c
/* engine2ini: writes in memory engine representation to INI file */
void engine2ini(M4SENGINEID eid) { dbl2ini( eid, IDC_PO4, m4e[eid].blr.po4 );
  dbl2ini( eid, IDC_PH, m4e[eid].blr.ph );
  dbl2ini( eid, IDC_BDTEMP, m4e[eid].blr.bdtemp );
  dbl2ini( eid, IDC_NH3, m4e[eid].blr.nh3 );

int2ini ( eid, IDC_LASTEVENTTIME, m4e[eid].lasteventtime );
  int2ini ( eid, IDC_EVENTID, m4e[eid].eventid );

m4e[eid].checksum = 0;  /* don't include above params in checksum*/
                          /* cause they can legitimately change */ dbl2ini ( eid, IDC_STARTTIME, m4e[eid].starttime);
  int2ini ( eid, IDC_RUNNING, m4e[eid].running );
  int2ini ( eid, IDC_LOGTOFILE, m4e[eid].logtofile );
  dbl2ini( eid, IDC_T, m4e[eid].blr.t );
  dbl2ini( eid, IDC_FAMIN, m4e[eid].blr.famin );
  dbl2ini( eid, IDC_FAMAX, m4e[eid].blr.famax );
  dbl2ini( eid, IDC_FADEF, m4e[eid].blr.fadef );
  dbl2ini( eid, IDC_PO4A, m4e[eid].blr.po4a );
  dbl2ini( eid, IDC_RATIOA, m4e[eid].blr.ratioa );
  dbl2ini( eid, IDC_SPGA, m4e[eid].blr.spga );
  dbl2ini( eid, IDC_FBMIN, m4e[eid].blr.fbmin );
  dbl2ini( eid, IDC_FBMAX, m4e[eid].blr.fbmax );
  dbl2ini( eid, IDC_FBDEF, m4e[eid].blr.fbdef );
  dbl2ini( eid, IDC_PO4B, m4e[eid].blr.po4b );
  dbl2ini( eid, IDC_RATIOB, m4e[eid].blr.ratiob );
  dbl2ini( eid, IDC_SPGB, m4e[eid].blr.spgb );
  dbl2ini( eid, IDC_M, m4e[eid].blr.m );
  dbl2ini( eid, IDC_DPO4, m4e[eid].blr.dpo4 );
  dbl2ini( eid, IDC_PO4SETPOINT, m4e[eid].blr.po4setpoint );
  dbl2ini( eid, IDC_MINPO4, m4e[eid].blr.minpo4 );
  dbl2ini( eid, IDC_MAXPO4, m4e[eid].blr.maxpo4 );
  dbl2ini( eid, IDC_DPH, m4e[eid].blr.dph );
  dbl2ini( eid, IDC_PHSETPOINT, m4e[eid].blr.phsetpoint );
  dbl2ini( eid, IDC_DPHSETPOINT, m4e[eid].blr.dphsetpoint );
  dbl2ini( eid, IDC_NAPO4RATIO, m4e[eid].blr.napo4ratio );
  dbl2ini( eid, IDC_MINNAPO4RATIO, m4e[eid].blr.minnapo4ratio );
  dbl2ini( eid, IDC_MAXNAPO4RATIO, m4e[eid].blr.maxnapo4ratio );
  dbl2ini( eid, IDC_MAX_SAMPLE_INTERVAL, m4e[eid].blr.max_sample_interval );
  dbl2ini( eid, IDC_MAX_OUTOFBOX_ADJUSTMENT,
                    m4e[eid].blr.max_outofbox_adjustment );
  dbl2ini( eid, IDC_MAX_RELATIVE_ERROR, m4e[eid].blr.max_relative_error );
```

```
dbl2ini( eid, IDC_BEPS,   m4e[eid].blr.beps );
dbl2ini( eid, IDC_BDMIN,  m4e[eid].blr.bdmin );
dbl2ini( eid, IDC_BDMAX,  m4e[eid].blr.bdmax );
dbl2ini( eid, IDC_FWFLOW, m4e[eid].fwflow );
dbl2ini( eid, IDC_MINFWNA,
    decodedouble(encodefloat(
        naleak2fwna(m4e[eid].blr.naleakmin,m4e[eid].fwflow))));
dbl2ini( eid, IDC_MAXFWNA,
    decodedouble(encodefloat(
        naleak2fwna(m4e[eid].blr.naleakmax,m4e[eid].fwflow))));
dbl2ini( eid, IDC_FWNA,
    decodedouble(encodefloat(naleak2fwna(m4e[eid].blr.l,m4e[eid].fwflow))));
dbl2ini( eid, IDC_FDT,         m4e[eid].blr.fdt );
dbl2ini( eid, IDC_LASTT,       m4e[eid].blr.lastt );
dbl2ini( eid, IDC_LASTBDTEMP,  m4e[eid].blr.lastbdtemp );
dbl2ini( eid, IDC_LASTPO4,     m4e[eid].blr.lastpo4 );
dbl2ini( eid, IDC_LASTNH3,     m4e[eid].blr.lastnh3 );
dbl2ini( eid, IDC_LASTPH,      m4e[eid].blr.lastph );
dbl2ini( eid, IDC_B4LASTT,     m4e[eid].blr.b4lastt );
dbl2ini( eid, IDC_B4LASTBDTEMP, m4e[eid].blr.b4lastbdtemp );
dbl2ini( eid, IDC_B4LASTPO4,   m4e[eid].blr.b4lastpo4 );
dbl2ini( eid, IDC_B4LASTNH3,   m4e[eid].blr.b4lastnh3 );
dbl2ini( eid, IDC_B4LASTPH,    m4e[eid].blr.b4lastph );
dbl2ini( eid, IDC_BD, decodedouble(encodefloat(m4e[eid].blr.bd)) );
dbl2ini( eid, IDC_LASTL,   m4e[eid].blr.lastl );
dbl2ini( eid, IDC_LASTBD,  m4e[eid].blr.lastbd );
dbl2ini( eid, IDC_DT1,     m4e[eid].blr.dt[0] );
dbl2ini( eid, IDC_DT2,     m4e[eid].blr.dt[1] );
dbl2ini( eid, IDC_FB1,     m4e[eid].blr.fb[0] );
dbl2ini( eid, IDC_FB2,     m4e[eid].blr.fb[1] );
dbl2ini( eid, IDC_FB3,     m4e[eid].blr.fb[2] );
dbl2ini( eid, IDC_FA1,     m4e[eid].blr.fa[0] );
dbl2ini( eid, IDC_FA2,     m4e[eid].blr.fa[1] );
dbl2ini( eid, IDC_FA3,     m4e[eid].blr.fa[2] );
dbl2ini( eid, IDC_LASTDT1, m4e[eid].blr.lastdt[0] );
dbl2ini( eid, IDC_LASTDT2, m4e[eid].blr.lastdt[1] );
dbl2ini( eid, IDC_LASTFA1, m4e[eid].blr.lastfa[0] );
dbl2ini( eid, IDC_LASTFA2, m4e[eid].blr.lastfa[1] );
dbl2ini( eid, IDC_LASTFA3, m4e[eid].blr.lastfa[2] );
dbl2ini( eid, IDC_LASTFB1, m4e[eid].blr.lastfb[0] );
dbl2ini( eid, IDC_LASTFB2, m4e[eid].blr.lastfb[1] );
dbl2ini( eid, IDC_LASTFB3, m4e[eid].blr.lastfb[2] );
int2ini( eid, IDC_UPDATESTATUS,     m4e[eid].blr.updatestatus );
int2ini( eid, IDC_LASTUPDATESTATUS, m4e[eid].blr.lastupdatestatus );
int2ini( eid, IDC_INITSTATUS,       m4e[eid].blr.initstatus );
int2ini( eid, IDC_UNDOABLE,         m4e[eid].blr.undoable );
```

```
    int2ini ( eid, IDC_SIMULATESSP, m4e[eid].simulatessp );
    int2ini ( eid, IDC_LOCALINPUT, m4e[eid].localinput );
    int2ini ( eid, IDC_NH3ENABLED, m4e[eid].nh3enabled );

int2ini( eid, IDC_CHECKSUM, m4e[eid].checksum);
}

/* randscierror: generates a random SCIL error code */
SCIError randscierror(double scilerrorfraction) {
    static SCIError scierr[]={
        ERROR_DATA_TYPE_MISMATCH,
        ERROR_INVALID_PROJECT_NAME,
        ERROR_LINK_ALREADY_ESTABLISHED,
        ERROR_LINK_NOT_CURRENTLY_ESTABLISHED,
        ERROR_POINT_NAME_NOT_FOUND,
        ERROR_PROJECT_NOT_FOUND,
        ERROR_SMARTSCAN_PLUS_NOT_RUNNING,
        ERROR_SMARTCARD_TIMEOUT };

if ( rand()  <= RAND_MAX*(1.0-scilerrorfraction))
        return (ERROR_NONE);
    else {
       int nerrors = sizeof(scierr)/sizeof(scierr[0]);
       return(scierr[rand() % nerrors]);
    }
}

/*simulateoperator: simulates input from the operator at regular intervals*/
void simulateoperator(M4SENGINEID eid) {
    double t = m4stimeinhours(eid);
    if (t - m4e[eid].lasteventtime >= SIMHOURSPEREVENT) {
        if (m4e[eid].eventid <
            sizeof(simsspinputs)/sizeof(simsspinputs[0])-1) {
            m4e[eid].eventid++;
            int2ini ( eid, IDC_EVENTID, m4e[eid].eventid );
        } /* just repeat last event when we get to the end of the array*/
        m4e[eid].lasteventtime = t;
        int2ini ( eid, IDC_LASTEVENTTIME, m4e[eid].lasteventtime );
        m4e[eid].currentevent = simsspinputs[m4e[eid].eventid];
    }
    /* else robo-operator is idle */
```

```c
}
/* The following sim* functions emulate the corresponding SCIL routines:*/ void simSCInitCommLink(SCIError *err) {
    *err = randscierror(SCILERRORFRACTION);
} void simSCCutCommLink(SCIError *err) {
    *err = randscierror(SCILERRORFRACTION);
} void simSCReadDigitalPoint(const char *s,BOOL *bit,SCIError *err) {
    M4SENGINEID eid = s[1] - '0';  /* hack to pull off engine id */
                                   /* from point name prefix */ s += lstrlen(nameprefix(eid));  /* skip over the engine specific prefix*/ if (lstrcmp(s, pid2name(IDC_UPDATE))==0)
        *bit = m4e[eid].currentevent.update;
    else if (lstrcmp(s, pid2name(IDC_UNDO))==0)
        *bit = m4e[eid].currentevent.undo;
    else if (lstrcmp(s, pid2name(IDC_REINIT))==0)
        *bit = m4e[eid].currentevent.reinit;
    else {
        M_BUGALERT("Invalid digital point during simulated SSP Read.");
    }

*err = randscierror(SCILERRORFRACTION);
} void simSCReadAnalogPoint(const char *s, float *value,SCIError *err) {
    M4SENGINEID eid = s[1] - '0';  /* hack to pull off engine id */
                                   /* from point name prefix */
    s += lstrlen(nameprefix(eid));  /* skip over the engine specific prefix*/ if (lstrcmp(s, pid2name(IDC_PH))==0)
        *value = e_phmodel(&m4e[eid].blr);
    else if (lstrcmp(s, pid2name(IDC_PO4))==0)
        *value = e_po4model(&m4e[eid].blr);
    else if (lstrcmp(s, pid2name(IDC_NH3))==0)
        *value = m4e[eid].blr.nh3;
    else if (lstrcmp(s, pid2name(IDC_BDTEMP))==0)
        *value = m4e[eid].blr.bdtemp;
```

```
        else
            M_BUGALERT("Invalid analog point during simulated SSP Read.");
        *err = randscierror(SCILERRORFRACTION);
    } void simSCWriteDigitalPoint(const char *s,BOOL bit,SCIError *err) {
    M4SENGINEID eid = s[1] - '0';  /* hack to pull off engine id */
                                   /* from point name prefix */ if (eid == currentengineid) {
        char buf[MAXSTRING+1];
        s += lstrlen(nameprefix(eid));  /* skip over the engine specific prefix*/
        if (lstrcmp(s, pid2name(IDC_UPDATE))==0) {
            m4e[eid].currentevent.update = bit;
            sprintf(buf, "update=%i ", bit);
        }
        else if (lstrcmp(s, pid2name(IDC_UNDO))==0) {
            m4e[eid].currentevent.undo = bit;
            sprintf(buf, "undo=%i ", bit);
        }
        else if (lstrcmp(s, pid2name(IDC_REINIT))==0) {
            m4e[eid].currentevent.reinit = bit;
            sprintf(buf, "reinit=%i ", bit);
        }
        else if (lstrcmp(s, pid2name(IDC_FLAG1))==0)
            sprintf(buf, "flags=(%i,", bit);
        else if (lstrcmp(s, pid2name(IDC_FLAG2))==0)
            sprintf(buf, "%i,", bit);
        else if (lstrcmp(s, pid2name(IDC_FLAG3))==0)
            sprintf(buf, "%i,", bit);
        else if (lstrcmp(s, pid2name(IDC_FLAG4))==0)
            sprintf(buf, "%i,", bit);
        else if (lstrcmp(s, pid2name(IDC_FLAG5))==0)
            sprintf(buf, "%i,", bit);
        else if (lstrcmp(s, pid2name(IDC_FLAG6))==0)
            sprintf(buf, "%i,", bit);
        else if (lstrcmp(s, pid2name(IDC_FLAG7))==0)
            sprintf(buf, m4e[eid].localinput ? "flags=(%i," : "%i,", bit);
        else if (lstrcmp(s, pid2name(IDC_FLAG8))==0)
            sprintf(buf, "%i,", bit);
        else if (lstrcmp(s, pid2name(IDC_FLAG9))==0)
            sprintf(buf, "%i,", bit);
        else if (lstrcmp(s, pid2name(IDC_FLAG10))==0)
            sprintf(buf, "%i,", bit);
```

```
      else if (lstrcmp(s, pid2name(IDC_FLAG11))==0)
        sprintf(buf, "%i,", bit);
      else if (lstrcmp(s, pid2name(IDC_FLAG12))==0)
        sprintf(buf, "%i) ", bit);
      else
        sprintf(buf,"%s=%i ", s, bit);

marque(buf);
  }

*err = randscierror(SCILERRORFRACTION);

} void simSCWriteAnalogPoint(const char *s,float f,SCIError *err) {
  M4SENGINEID eid = s[1] - '0'; /* hack to pull off engine id */
                                /* from point name prefix */
  if (currentengineid == eid) {
    char buf[MAXSTRING+1];
    s += lstrlen(nameprefix(eid)); /* skip over the engine specific prefix*/
    if (lstrcmp(s, pid2name(IDC_AFEED))==0)
      sprintf(buf, "a=%.5g ", f);
    else if (lstrcmp(s, pid2name(IDC_BFEED))==0)
      sprintf(buf, "b=%.5g ", f);
    else {
#if TESTING
      sprintf(buf,"%s=%.5g ", s, f);
#else
      sprintf(buf,"");
#endif
    }
    marque(buf);
  }
  *err = randscierror(SCILERRORFRACTION);
}

/*isvalidnumber: if s is a valid number or numeric prefix, TRUE, else FALSE*/

BOOL isvalidnumber(char *s) {
  char *endofnumber = NULL;
  double value = strtod(s, &endofnumber);
  if (value <= -FLT_MAX || value >= FLT_MAX)
    return(FALSE); /* we require that number be in range of floats */
  else /* check if entire number was read by strtod */
    return(*endofnumber == '\0' ? TRUE : FALSE);
```

```
}

/* isnumericprefix: FALSE if s is not valid prefix to a number, else TRUE */
BOOL isnumericprefix(char *s) {
    s += strspn(s, " ");    /* skip leading whitespace 'cause strtod() does*/
    if (lstrcmp(s,".")==0 ||
        lstrcmp(s,"-")==0 || lstrcmp(s,"-.")==0 ||
        lstrcmp(s,"+")==0 || lstrcmp(s,"+.")==0)
        return(TRUE);  /* special cases of valid prefixes that are not numbers*/
    else
        return(isvalidnumber(s));
}

/* forcevalidnumber: truncates the string to make it a valid number. */
char *forcevalidnumber(char *s) {
    if (!isvalidnumber(s))
        lstrcpy(s, NANSTRING);
    return(s);
}

/*inrange: is x between low and high (ignores NANFLT) */
BOOL inrange(double x, double low, double high) {
    if (x == NANFLT)
        return(TRUE);
    else if ((low != NANFLT && x < low) || (high != NANFLT && x > high))
        return(FALSE);
    else
        return(TRUE);
}

/* forceinrange: forces x between low and high; ignores NANFLT */
double forceinrange(double x, double low, double high) {
    if (x == NANFLT)
        return(x);
    else if (low != NANFLT && x <= low)
        return(low);
    else if (high != NANFLT && x >= high)
        return(high);
    else
        return(x);
}

/* updatessppoints: sets flags that force MACC4SSP to update SSP
```

```
        action flags (update, undo, and reinit) and status flags */
/*(actual SSP settings are made in response to the WM_TIMER message)*/
/* (need to do this because initial settings of SSP points are often
     hard to predict in advance, at least in my experience) */
void updatessppoints(M4SENGINEID eid) {
            m4e[eid].flagsuptodate = FALSE;/*clear old flags...*/
            m4e[eid].actionsuptodate=FALSE;/*...and old actions*/
}

/*
SmartCard Interface Library (SCIL) based routines for accessing SmartScan Plus
*/

SCIError sciinit(M4SENGINEID eid) {
   SCIError err = ERROR_NONE;
#if WORKAROUND
   static BOOL initialized = FALSE;
   if (initialized) {
      m4e[eid].scierr = err;
      return(err);
   }
#endif
   if (!m4e[eid].simulatessp) SCInitCommLink(&err);
   if (ERROR_SMARTSCAN_PLUS_NOT_RUNNING == err)
     updatessppoints(eid);  /* when SSP does start up, points must be*/
                            /* in a well defined initial state */
   m4e[eid].scierr = err;   /* note that this sets the scierr field */
                            /* to ERROR_NONE if init succeeded */
#if WORKAROUND
   if (err == ERROR_NONE) initialized = TRUE;
#endif
   return(err);
}

SCIError scifini(M4SENGINEID eid) {
   SCIError err=ERROR_NONE;
#if WORKAROUND
   return(err);
#endif
   if (!m4e[eid].simulatessp) SCCutCommLink(&err);
   return(err);
}

/* maybestoreerror: remember error if the 1st seen since errors were cleared */

SCIError maybestoreerror(M4SENGINEID eid, M4SPARAMID pid, SCIError err) {
```

```
    if (m4e[eid].scierr == ERROR_NONE && err != ERROR_NONE) {
      m4e[eid].scierr = err;
      m4e[eid].pidscierr = pid;
    }
    return(err);
}
/* timedoutbefore: returns true if the system timed since errors were cleared*/

/* (5/28/94) Phil Gabler reported that he noted that Windows became
    unusable (VERY SLOW) when MACC4SSP was run on a system that had
    Smartscan Plus but no SmartCard. He also reported that
    ERROR_SMARTCARD_TIMEOUT was always showing. This routine is used to
    shortcircuit SCIL calls after the first ERROR_SMARTCARD_TIMEOUT; since
    each such timeout takes 0.5 seconds and the timer messages come in
    every 3 seconds, this gives Windows a "timeout breather" and is intended
    to correct the problem of multiple SCIL 0.5 sec timeouts adding up to
    VERY SLOW Windows response.

This routine relies on the fact that each time a WM_TIMER message comes
    in the sciinit() call is made and, if succesful, clears any old
    timeout errors stored in the scierr field.
*/
BOOL timedoutbefore(M4SENGINEID eid, SCIError *err) {
    if (m4e[eid].scierr == ERROR_SMARTCARD_TIMEOUT) {
       *err = ERROR_SMARTCARD_TIMEOUT;
       return(TRUE);
    }
    else
       return(FALSE);
}

/* scigetdouble: retrieves value associated with an engine,parameter from SSP*/
double scigetdouble(M4SENGINEID eid, M4SPARAMID pid) {
   float f;
   SCIError err = ERROR_NONE;
   if (m4e[eid].localinput)
        f = ini2dbl(eid, pid);
   else if (!timedoutbefore(eid, &err)) {
      if (m4e[eid].simulatessp)
         simSCReadAnalogPoint(m4spointname(eid,pid), &f, &err);
      else
         SCReadAnalogPoint(m4spointname(eid,pid), &f, &err);
   }
   maybestoreerror(eid, pid, err);
```

```
        if (err == ERROR_NONE)
            return(decodedouble(encodefloat(f)));
/* the curious encode/decode above is a hack to simplify numeric formatting*/
    else
        return (NANFLT);
}

/*scisetdouble: sends value to the SSP point associated with engine,parameter*/

SCIError scisetdouble(M4SENGINEID eid, M4SPARAMID pid, double x) {
    float f = x;
    SCIError err = ERROR_NONE;
    if (!timedoutbefore(eid, &err)) {
        if (m4e[eid].simulatessp)
            simSCWriteAnalogPoint(m4spointname(eid,pid), (const float) f, &err);
        else
            SCWriteAnalogPoint(m4spointname(eid,pid), (const float) f, &err);
    }
    maybestoreerror(eid, pid, err);
    return(err);
}

/* scigetbit: retrieves flag associated with an engine,parameter from SSP */

BOOLPLUS scigetbit(M4SENGINEID eid, M4SPARAMID pid) {
    BOOL bit;
    SCIError err = ERROR_NONE;

if (m4e[eid].localinput)
        bit = ini2int(eid, pid);
    else if (!timedoutbefore(eid, &err)) {
        if (m4e[eid].simulatessp)
            simSCReadDigitalPoint(m4spointname(eid,pid), &bit, &err);
        else
            SCReadDigitalPoint(m4spointname(eid,pid), &bit, &err);
    }
    maybestoreerror(eid, pid, err);
    return ( (err == ERROR_NONE) ? bit : NANBOOL );
}

/* scisetbit: sends flag to the SSP point associated with an engine,parameter*/

SCIError scisetbit(M4SENGINEID eid, M4SPARAMID pid, BOOL bit) {
    SCIError err=ERROR_NONE;
    if (!timedoutbefore(eid, &err)) {
```

122

```
      if (m4e[eid].simulatessp)
         simSCWriteDigitalPoint(m4spointname(eid,pid), bit, &err);
      else
         SCWriteDigitalPoint(m4spointname(eid,pid), bit, &err);
   }
   maybestoreerror(eid, pid, err);
   return(err);
}

/*
    scierrstr: returns the engine's error string; basically just the
    SCIL error keywords except, sometimes, point specific info is added.
*/ char *scierrstr(M4SENGINEID eid) {
   static char scierr[MAXSTRING+1];
   switch(m4e[eid].scierr) { case ERROR_NONE:
           return("ERROR_NONE");
      case ERROR_INVALID_PROJECT_NAME:
           return("ERROR_INVALID_PROJECT_NAME");
      case ERROR_PROJECT_NOT_FOUND:
           return("ERROR_PROJECT_NOT_FOUND");
      case ERROR_SMARTSCAN_PLUS_NOT_RUNNING:
           return("ERROR_SMARTSCAN_NOT_RUNNING");
      case ERROR_SMARTCARD_TIMEOUT:
           return("ERROR_SMARTCARD_TIMEOUT");

case ERROR_POINT_NAME_NOT_FOUND:   /* SCIL errors that involve points*/
           sprintf(scierr, "ERROR_%s_NOTFOUND",
                      m4spointname(eid,m4e[eid].pidscierr));
           return(scierr);
      case ERROR_DATA_TYPE_MISMATCH:
           sprintf(scierr, "ERROR_%s's_DATA_TYPE",
                      m4spointname(eid,m4e[eid].pidscierr));
           return(scierr);

/* these cases should never happen (or else it's a bug): */ case ERROR_LINK_ALREADY_ESTABLISHED:
        return("BUG_ALREADY_LINKED");
      case ERROR_LINK_NOT_CURRENTLY_ESTABLISHED:
        return("BUG_NOT_LINKED");
      default:
        return("BUG_UNRECOGNIZED_ERROR");
```

```c
    }
}

/* title: returns the title bar for the dialog box (acts as status line)*/ char *title(M4SENGINEID eid) {
    static char titlebuf[MAXSTRING+1];
    sprintf(titlebuf, "MACC4SSP Boiler%i (%s)", eid,
                    (!m4e[eid].running)    ? "STOPPED" :
                     m4e[eid].badchecksum ? "BADCHECKSUM!!!" :
                                            scierrstr(eid) );
    return(titlebuf);
}

/* getssprequest: loads data fields and returns requested action shown below: */ typedef enum ssprequest {
    NOOPSSPREQUEST,
    UPDATESSPREQUEST,
    REINITSSPREQUEST,
    UNDOSSPREQUEST,
    OUTOFRANGESSPREQUEST,
    NODATASSPREQUEST,
    AMBIGUOUSSSPREQUEST
} SSPREQUEST;

SSPREQUEST getssprequest(M4SENGINEID eid) {

BOOLPLUS update, reinit, undo;
    double ph, po4, nh3, bdtemp;

if (!m4e[eid].actionsuptodate)/* avoids reading the same action twice */
        return(NOOPSSPREQUEST);        /* if last action was not cleared*/
    else if (NANBOOL == (update = scigetbit(eid, IDC_UPDATE)) ||
             NANBOOL == (reinit = scigetbit(eid, IDC_REINIT)) ||
             NANBOOL == (undo   = scigetbit(eid, IDC_UNDO)))
        return(NOOPSSPREQUEST);/*can't read all action flags;wait til next timer*/
    else if (update + reinit + undo == 0) /* either no, ...*/
        return(NOOPSSPREQUEST);
    else if (update + reinit + undo > 1) { /* or several, actions requested */
        M_M4SERROR("Ambiguous request was ignored.");
        return(AMBIGUOUSSSPREQUEST);
    }
    else if (undo)   /* undo has no arguments (no need to read pH, PO4, etc.)*/
```

```
        return(UNDOSSPREQUEST);
    else if ( NANFLT == (ph    = scigetdouble(eid, IDC_PH)) ||
              NANFLT == (po4   = scigetdouble(eid, IDC_PO4)) ||
              (m4e[eid].nh3enabled &&
              NANFLT == (nh3   = scigetdouble(eid, IDC_NH3))) ||
              NANFLT == (bdtemp = scigetdouble(eid, IDC_BDTEMP)) )
        return(NODATASSPREQUEST); /* can't read required info; wait til next timer*/
    else {
        M_ASSERT(update+reinit==1);
/* check/display range errors on each numerical input */
        if (!inrange(ph, pid2low(IDC_PH), pid2high(IDC_PH))) {
            M_M4SERROR2(rangeerror(IDC_PH));
            return(OUTOFRANGESSPREQUEST);
        }
        else if (!inrange(po4, pid2low(IDC_PO4), pid2high(IDC_PO4))) {
            M_M4SERROR2(rangeerror(IDC_PO4));
            return(OUTOFRANGESSPREQUEST);
        }
        else if (!inrange(bdtemp, pid2low(IDC_BDTEMP), pid2high(IDC_BDTEMP))) {
            M_M4SERROR2(rangeerror(IDC_BDTEMP));
            return(OUTOFRANGESSPREQUEST);
        }
```

```
        else if (m4e[eid].nh3enabled &&
                !inrange(nh3, pid2low(IDC_NH3),pid2high(IDC_NH3))) {
            M_M4SERROR2(rangeerror(IDC_NH3));
            return(OUTOFRANGESSPREQUEST);
        }
        else {                          /* all inputs in allowed range so... */
            m4e[eid].blr.ph    = ph;    /* store data needed to service request */
            m4e[eid].blr.po4   = po4;
            if (m4e[eid].nh3enabled)
                m4e[eid].blr.nh3   = nh3;
            m4e[eid].blr.bdtemp = bdtemp;
            return(update ? UPDATESSPREQUEST : REINITSSPREQUEST);
        }
    }
}

/*encodeflags: encodes status code flags as a string */ char *encodeflags(M4SENGINEID eid) {
    static char flagtext[MAXSTRING+1];

flagtext[0] = (m4e[eid].blr.updatestatus&E_INDETERMINATE)   ? '1':'_';
    flagtext[1] = (m4e[eid].blr.updatestatus&E_BOX_UNREACHABLE) ? '2':'_';
    flagtext[2] = (m4e[eid].blr.updatestatus&E_OUTOFBOX_TOOLONG) ? '3':'_';
    flagtext[3] = (m4e[eid].blr.updatestatus&E_POINT_UNREACHABLE) ? '4':'_';
    flagtext[4] = (m4e[eid].blr.updatestatus&E_BOX_UNMAINTAINABLE) ? '5':'_';
    flagtext[5] = (m4e[eid].blr.updatestatus&E_POINT_UNMAINTAINABLE) ?'6':'_';
    flagtext[6] =
        (m4e[eid].blr.t-m4e[eid].blr.lastt>m4e[eid].blr.max_sample_interval)
        ? '7' : '_';
    flagtext[7] = (m4e[eid].blr.updatestatus & E_NOTUPDATED) ? '8':'_';
    flagtext[8] = (m4e[eid].blr.updatestatus & E_INCONSISTENT_PO4) ? '9':'_';
    flagtext[9] = (m4e[eid].blr.updatestatus & E_INCONSISTENT_PH) ? 'A':'_';
    flagtext[10] = (m4e[eid].blr.initstatus!=E_INITOK) ? 'B':'_';
    flagtext[11] = m4e[eid].badchecksum ? 'C':'_';
    flagtext[12]='\0';
    return(flagtext);
}

/* logfile: returns the name of the MACC4SSP log file for a given engine */ char *logfile(M4SENGINEID eid) {
    return(lstrcat(lstrcat(m4spath(),nameprefix(eid)),".LOG"));
}
```

```c
/* fileexists: checks if a file exists. */
BOOL fileexists(char *fname) {
    unsigned attr=0;
        return((_dos_getfileattr(fname,&attr) == 0)?TRUE:FALSE);
}

/* logaction: used to log updates, reinits, undos, STARTs, and STOPs */
void logaction(M4SENGINEID eid,
            M4SPARAMID pid)    /* indicates action: update, reinit, etc.*/
{
    int hFile = -1;
    long lastbyte = -1;

if (!m4e[eid].logtofile) /* skip if logging is disabled */
        ;
    else if (fileexists(logfile(eid)) &&
        -1 == (hFile = _lopen(logfile(eid), OF_READWRITE)))
        M_M4SERROR("Cannot open log file");
    else if (!fileexists(logfile(eid)) &&
            -1==(hFile = _lcreat(logfile(eid), 0)))
        M_M4SERROR("Cannot create log file");
    else if (-1 == (lastbyte = _llseek(hFile, 0, 2)))
        M_M4SERROR("Cannot move to end of log file");
    else { /* print out header (only if file empty) and next log file line */
        static char tobeprinted[6*MAXSTRING+1];
        if (lastbyte > 1) {   /* file not empty, assume it already has header*/
            lstrcpy(tobeprinted, "");
        }
        else {                      /* empty file, add header to it */
            sprintf(tobeprinted,
                "%-4s,%-6s,%-20s,%-14s,%-14s,"
                "%-9s,%-9s,%-9s,%-9s,%-9s,%-9s,%-9s,%-9s,%-9s,%-9s,%-9s,%-9s",
                "Sim?","Action","DateTime","HoursSince1970","flags", "pH", "PO4",
                "bdtemp","NH3", "fa1", "fa2", "fa3", "fb1", "fb2", "fb3",
                "dt1", "dt2");
        }
/* append any to be printed info to the (optional) header created above */
        sprintf(tobeprinted+lstrlen(tobeprinted),
                "\n%-4s,%-6s,%-20s,%-14f,%-14s,",
                m4e[eid].simulatessp ? "Yes" : "No", pid2name(pid),
                m4sdatetime(timeinhours()), m4e[eid].blr.t,
                encodeflags(eid));
        sprintf(tobeprinted+lstrlen(tobeprinted),
```

```
            "%-9f,%-9f,%-9f,%-9f,%-9f,%-9f,%-9f,%-9f,%-9f,%-9f,%-9f",
            m4e[eid].blr.ph, m4e[eid].blr.po4,
            m4e[eid].blr.bdtemp, fixnandbl(m4e[eid].blr.nh3,0.0),
            m4e[eid].blr.fa[0], m4e[eid].blr.fa[1],
            m4e[eid].blr.fa[2], m4e[eid].blr.fb[0], m4e[eid].blr.fb[1],
            m4e[eid].blr.fb[2], m4e[eid].blr.dt[0], m4e[eid].blr.dt[1] );
        if (_lwrite(hFile, tobeprinted, lstrlen(tobeprinted)) <= 0)
            M_M4SERROR("Cannot write to log file");
    }
    if (hFile != -1 && -1 == _lclose(hFile))
        M_M4SERROR("Cannot close log file");
}

/*maybeclearactions: clear action flags if not already cleared */

BOOL maybeclearactions(M4SENGINEID eid) {
    if (!m4e[eid].actionsuptodate) {
        if (m4e[eid].localinput) {
            int2ini(eid, IDC_UPDATE, FALSE);
            int2ini(eid, IDC_UNDO, FALSE);
            int2ini(eid, IDC_REINIT, FALSE);
            m4e[eid].actionsuptodate = TRUE;
        }
        else {
            m4e[eid].actionsuptodate =(scisetbit(eid,IDC_UPDATE,FALSE)==ERROR_NONE &&
                                      scisetbit(eid,IDC_UNDO,  FALSE)==ERROR_NONE &&
                                      scisetbit(eid,IDC_REINIT,FALSE)==ERROR_NONE);
        }
    }
    return(m4e[eid].actionsuptodate);
}

/* maybesetflags: sets flags in SSP that correspond to the updatestatus */
/* note: order in which flags are set matters due to a kludge used
    in simSCWriteDigitalPoint() */

BOOL maybesetflags(M4SENGINEID eid) {
    BOOL f1,f2,f3,f4,f5,f6,f7,f8,f9,f10,f11,f12;

#define M_BIT(eid,flag) ((m4e[eid].blr.updatestatus & (flag))!=0)

if (!m4e[eid].flagsuptodate) { /* update SSP flags if required */
        if (m4e[eid].localinput) {
            f7=(ERROR_NONE==scisetbit(eid,IDC_FLAG7,
                m4e[eid].blr.t-m4e[eid].blr.lastt>m4e[eid].blr.max_sample_interval));
```

```
            f12=(scisetbit(eid,IDC_FLAG12,m4e[eid].badchecksum)==ERROR_NONE);
            m4e[eid].flagsuptodate = (f7 && f12);
        }
        else {
            f1=(scisetbit(eid,IDC_FLAG1, M_BIT(eid,E_INDETERMINATE))==ERROR_NONE);
            f2=(scisetbit(eid,IDC_FLAG2, M_BIT(eid,E_BOX_UNREACHABLE))==ERROR_NONE);
            f3=(scisetbit(eid,IDC_FLAG3, M_BIT(eid,E_OUTOFBOX_TOOLONG))==ERROR_NONE);
            f4=(scisetbit(eid,IDC_FLAG4, M_BIT(eid,E_POINT_UNREACHABLE))
                ==ERROR_NONE);
            f5=(scisetbit(eid,IDC_FLAG5, M_BIT(eid,E_BOX_UNMAINTAINABLE))
                ==ERROR_NONE);
            f6=(scisetbit(eid,IDC_FLAG6, M_BIT(eid,E_POINT_UNMAINTAINABLE))
                ==ERROR_NONE);
            f7=(ERROR_NONE==scisetbit(eid,IDC_FLAG7,
                m4e[eid].blr.t-m4e[eid].blr.lastt>m4e[eid].blr.max_sample_interval));
            f8=(scisetbit(eid,IDC_FLAG8, M_BIT(eid,E_NOTUPDATED))==ERROR_NONE);
            f9=(scisetbit(eid,IDC_FLAG9, M_BIT(eid,E_INCONSISTENT_PO4))==ERROR_NONE);
            f10=(scisetbit(eid,IDC_FLAG10,M_BIT(eid,E_INCONSISTENT_PH))==ERROR_NONE);
            f11=(scisetbit(eid,IDC_FLAG11,m4e[eid].blr.initstatus!=E_INITOK)
                ==ERROR_NONE);
            f12=(scisetbit(eid,IDC_FLAG12,m4e[eid].badchecksum)==ERROR_NONE);
            m4e[eid].flagsuptodate = (f1 && f2 && f3 && f4 && f5 && f6 && f7 && f8 &&
                                     f9 && f10 && f11 && f12);
        }
    }
    return(m4e[eid].flagsuptodate);
}
/*setbuttontext: sets the appropriate text string for an engine's button */
/* (assumes that IDC_ENGINE0, IDC_ENGINE1, ... ids are sequential) */ void setbuttontext(HWND hDlg, M4SENGINEID eid) {
    static char buttontext[MAXSTRING+1];
    sprintf(buttontext, "%sBoiler%i%s",
        m4e[eid].running ? "*" : "", eid, m4e[eid].running ? "*" : "");
    s2ctrl(GetDlgItem(hDlg, IDC_ENGINE0+eid), buttontext);
}

/*updateform: updates those fields which change while engine is running */ void updateform(HWND hDlg, M4SENGINEID eid) { if (!m4e[eid].running) {
        s2ctrl(GetDlgItem(hDlg,IDC_DATETIME), "");
        s2ctrl(GetDlgItem(hDlg,IDC_AFEED), "");
        s2ctrl(GetDlgItem(hDlg,IDC_BFEED), "");
        s2ctrl(GetDlgItem(hDlg,IDC_STATUSFLAGS), "");
```

129

```
        }
    else  }   /* update the form from the current in-memory info */
        if (!m4e[eid].localinput) {
            s2ctrl(GetDlgItem(hDlg, IDC_PH), encodeshortfloat(m4e[eid].blr.ph));
            s2ctrl(GetDlgItem(hDlg, IDC_PO4), encodeshortfloat(m4e[eid].blr.po4));
            if (m4e[eid].nh3enabled)
                s2ctrl(GetDlgItem(hDlg, IDC_NH3), encodeshortfloat(m4e[eid].blr.nh3));
            s2ctrl(GetDlgItem(hDlg, IDC_BDTEMP),
                encodeshortfloat(m4e[eid].blr.bdtemp));
        }
        s2ctrl(GetDlgItem(hDlg, IDC_BD), encodefloat(m4e[eid].blr.bd));
        s2ctrl(GetDlgItem(hDlg, IDC_BDMIN), encodefloat(m4e[eid].blr.bdmin));
        s2ctrl(GetDlgItem(hDlg, IDC_BDMAX), encodefloat(m4e[eid].blr.bdmax));
        s2ctrl(GetDlgItem(hDlg, IDC_FWNA),
            encodefloat(naleak2fwna(m4e[eid].blr.l,m4e[eid].fwflow)));
        s2ctrl(GetDlgItem(hDlg, IDC_MINFWNA),
            encodefloat(naleak2fwna(m4e[eid].blr.naleakmin,m4e[eid].fwflow)));
        s2ctrl(GetDlgItem(hDlg, IDC_MAXFWNA),
            encodefloat(naleak2fwna(m4e[eid].blr.naleakmax,m4e[eid].fwflow)));
        s2ctrl(GetDlgItem(hDlg, IDC_DPO4), encodefloat(m4e[eid].blr.dpo4));
        s2ctrl(GetDlgItem(hDlg, IDC_DPH), encodefloat(m4e[eid].blr.dph));

/* note: macc4.c's e_init() may fill in min/max bd and naleak, dpo4 and
   dph, hence above lines to update screen to reflect such fill-ins */ s2ctrl(GetDlgItem(hDlg,IDC_DATETIME), m4sdatetime(m4e[eid].blr.lastt));
        s2ctrl(GetDlgItem(hDlg,IDC_AFEED),
            encodefloat((float) e_afeed(&m4e[eid].blr)));
        s2ctrl(GetDlgItem(hDlg,IDC_BFEED),
            encodefloat((float) e_bfeed(&m4e[eid].blr)));
        s2ctrl(GetDlgItem(hDlg,IDC_STATUSFLAGS), encodeflags(eid));

}

}

/* predictphpo4: computes and displays MACC4 predicted pH/PO4. pH is computed
   at room temperature and without ammonia (NH3=0).*/ void predictphpo4(M4SENGINEID eid,   /* id of boiler controller/model */
                  double deltat    /* number of hours into the future to look */
                 ) {
    static char predictstr[2*MAXSTRING+1];
    E_BOILER blr = m4e[eid].blr;   /*make a copy so we can change with impunity*/
```

```c
    blr.t = m4stimeinhours(eid) + deltat;
    blr.bdtemp = ROOMTEMPERATUREDEGREESF;  /* Uses room temperature and */
    blr.nh3 = 0.0;                         /* no NH3 to be compatible/comparable with */
                                           /* pH setpoint (which is so defined)      */ blr.po4 = e_po4model(&blr);  /* set current PO4, pH to model projections*/
    blr.ph  = e_phmodel(&blr);

sprintf(predictstr,
"The %s MACC4 forecast: PO4=%.5g, pH (no NH3; %g F)=%.5g Na:PO4=%.5g ",
        m4sdatetime(blr.t), blr.po4, ROOMTEMPERATUREDEGREESF,
        blr.ph, e_congruencyratio(&blr));
    clearmarque();
    marque(predictstr);  /* display the forecast */
}

/*oktostopmessage:confirmation text message for stopping a boiler controller*/
char *oktostopmessage(M4SENGINEID eid) {
    static char oktostoptext[MAXSTRING+1];
    sprintf(oktostoptext, "OK to stop MACC4SSP Boiler%i?", eid);
    return(oktostoptext);
}
/*
    closewarningmessage: warning message if they try to shut down MACC4
    while boilers are still running/being controlled */ char *closewarningmessage(int numberrunning) {
    char boilerlist[MAXSTRING+1]={0};
    static char closewarningtext[4*MAXSTRING+1];
#define M_BOILERTEXT(eid) (m4e[eid].running ? (", Boiler" #eid) : "")
    sprintf(boilerlist, "%s%s%s%s%s%s%s%s%s%s", M_BOILERTEXT(0), M_BOILERTEXT(1),
        M_BOILERTEXT(2), M_BOILERTEXT(3), M_BOILERTEXT(4), M_BOILERTEXT(5),
        M_BOILERTEXT(6), M_BOILERTEXT(7), M_BOILERTEXT(8), M_BOILERTEXT(9));
    sprintf(closewarningtext,
"%s %s still running. If you close MACC4SSP now, the chemical feed rates for "
"%s will not be updated until you re-launch MACC4SSP. Unless MACC4SSP is "
"re-launched promptly, this could result in poor chemical control.",
        boilerlist+2, (numberrunning > 1) ? "are" : "is",
        (numberrunning > 1) ? "these boilers" : "this boiler");

return(closewarningtext);
}

/* setfocusnextboiler: sets focus to the next boiler's selection button*/
/* (assumes boiler selection button id's are sequential) */
```

```
void setfocusnextboilerbutton(HWND hDlg, M4SENGINEID eid) {
    SetFocus(GetDlgItem(hDlg,IDC_ENGINE0+(eid+1)%(MAXENGINEID+1)));
}

/* WndProc: handles all messages Windows sends to our main window/dialog box */ long FAR PASCAL WndProc(HWND hDlg, WORD message, WORD wParam, LONG lParam)
{
    static int  numberrunning = 0;
    static BOOL windowlocked  = TRUE;

HWND hCtrl    = LOWORD(lParam);   /* parse messages to controls */
    int  ctrlmsg  = HIWORD(lParam);
    int  eid      = 0;

switch(message) { case WM_CREATE:
/*
   Note that SSP need not be running at this point; if SSP communications are
   down for an extended period we "ride the clutch" (c.f WM_TIMER
   case) until SSP communications are restored  and sciinit()==ERROR_NONE.
*/
            for (numberrunning = 0, eid = MINENGINEID; eid <= MAXENGINEID; eid++){
                m4e[eid].running=fixnanint(ini2int(eid,IDC_RUNNING),FALSE);
                if (m4e[eid].running) {
                    numberrunning++;
                    if (ini2engine(eid)) { /* bad checksum -- alert them */
                        M_M4SERROR(
"BAD CHECKSUM! Cannot restore state of a running engine!");
                    }
                    logaction(eid, IDC_LAUNCH);
                    m4e[eid].currentevent = nullevent;
                    updatessppoints(eid);/*brings SSP points to well defined state*/
                }
            }
/* current engine id is always stored in the default engine's INI file */
            currentengineid=fixnanint(ini2int(DEFENGINEID,IDC_CURRENTENGINEID),
                                              DEFENGINEID);
            M_ASSERT(currentengineid >= MINENGINEID);
            M_ASSERT(currentengineid <= MAXENGINEID);
            if (currentengineid < MINENGINEID || currentengineid > MAXENGINEID)
                currentengineid = DEFENGINEID;   /* defensive programming */
```

132

```
        windowlocked = TRUE;   /* user must enter password to change/close */ break;

case WM_SETFOCUS:
     if (windowlocked)
        SetFocus(GetDlgItem(hDlg, IDC_PASSWORD));
     break;

case WM_COMMAND:

switch(wParam) { case IDC_LOGTOFILE: /* record change in log status in ini file*/ m4e[currentengineid].logtofile = getcheckboxstate(hCtrl);
           int2ini(currentengineid, IDC_LOGTOFILE,
                        m4e[currentengineid].logtofile);

break;

case IDC_SIMULATESSP:

m4e[currentengineid].simulatessp = getcheckboxstate(hCtrl);
           int2ini(currentengineid, IDC_SIMULATESSP,
                       m4e[currentengineid].simulatessp);
         break;

case IDC_LOCALINPUT:

m4e[currentengineid].localinput = getcheckboxstate(hCtrl);
            int2ini(currentengineid, IDC_LOCALINPUT,
                      m4e[currentengineid].localinput);
        constraininputs(hDlg, currentengineid, windowlocked);
     s2ctrl(GetDlgItem(hDlg, IDC_POINTNAMES),pointnames(currentengineid));

break;

case IDC_NH3ENABLED:

m4e[currentengineid].nh3enabled = getcheckboxstate(hCtrl);
            int2ini(currentengineid, IDC_NH3ENABLED,
                      m4e[currentengineid].nh3enabled);
     if (!m4e[currentengineid].nh3enabled) {       /*if NH3 not used*/
        s2ini(currentengineid, IDC_NH3, NANSTRING);   /*clear in INI file*/
        s2ctrl(GetDlgItem(hDlg, IDC_NH3), NANSTRING);/*as well as on form*/
```

133

```
        }
    constraininputs(hDlg, currentengineid, windowlocked);
  s2ctrl(GetDlgItem(hDlg, IDC_POINTNAMES),pointnames(currentengineid));

break;

case IDC_UPDATE:
case IDC_UNDO:
case IDC_REINIT:
    M_ASSERT(m4e[currentengineid].localinput);
    int2ini(currentengineid, wParam, TRUE);
    SendMessage(hDlg, WM_TIMER, M4STIMERID, NULL);
    break;

case IDC_LOCKWINDOW:
    windowlocked = TRUE;
  s2ctrl(GetDlgItem(hDlg, IDC_PASSWORD),"");    /* clear password */
    constraininputs(hDlg, currentengineid, windowlocked);
    if (windowlocked)
        SetFocus(GetDlgItem(hDlg, IDC_PASSWORD));
    break;

case IDC_PASSWORD:

if (windowlocked && lstrcmp(ctrl2s(hCtrl), "ERIC4") == 0) {
        windowlocked = FALSE;
      s2ctrl(GetDlgItem(hDlg, IDC_PASSWORD),"");    /* clear password */
        constraininputs(hDlg, currentengineid, windowlocked);
        SetFocus(hDlg);
    }
    break;

case IDC_FORECAST:

M_ASSERT(m4e[currentengineid].running);

predictphpo4(currentengineid,
  max(0.0,fixnandbl(ini2dbl(currentengineid, IDC_FORECASTTIME),0.0)));

break;

/* Numeric only entry restrictions and on-the-fly initialization file
    backup of edit control entries:

Invariants:
```

134

1) All edit control entries agree with those stored in the initialization file, except possibly changes made to the edit control that has the focus.

2) Edit controls below either contain a valid number, or have the focus (caret or text cursor) and contain a valid numeric prefix (.. -, -. are all examples of valid numeric prefixes that aren't valid numbers).

These invariants are assumed to hold initially (ini2dlg() call in IDC_LOADFORM command message, sent to main window in WinMain, guarantees this).

The first invariant is maintained by writing the final numeric value in the edit control to the initialization file when the control loses the focus, unless this edit control text has not changed.

The second invariant is maintained as changes are made to the edit controls (these changes generate EN_CHANGE messages) by the following rules:

1) Function forcenumeric() is used to either truncate or totally eliminate non-numeric entries for any changes that lead to non-numbers in those controls that do not have the focus. forcenumeric() is also applied to the control when it just loses the focus (via the EN_KILLFOCUS message).

2) When the control has the focus, the most recently validated text is remembered and the control text is restored to this value if any changes result in an entry that is not a valid numeric prefix. This is mostly intended to reject user entry errors (e.g. pressing the 'A' key).

```
*/
        case IDC_MINFWNA: case IDC_MAXFWNA: case IDC_FWNA: case IDC_BDMAX:
        case IDC_BDMIN: case IDC_M: case IDC_BDTEMP: case IDC_DPHSETPOINT:
        case IDC_PHSETPOINT: case IDC_DPH: case IDC_PH: case IDC_MAXPO4:
          case IDC_MINPO4: case IDC_PO4SETPOINT: case IDC_DPO4:
          case IDC_PO4: case IDC_SPGA: case IDC_SPGB: case IDC_PO4B:
          case IDC_FBDEF: case IDC_FBMAX: case IDC_FBMIN: case IDC_RATIOB:
            case IDC_RATIOA: case IDC_PO4A: case IDC_FADEF:
            case IDC_FAMAX: case IDC_FAMIN:  case IDC_BD:
          case IDC_FORECASTTIME: case IDC_FWFLOW: case IDC_NH3:

switch(ctrlmsg) {
            static HWND currentctrl = NULL;   /* handle to control in focus*/
            static BOOL ctrlchanged = FALSE;  /* did control in focus change?*/
            static char lasttext[MAXSTRING+1]; /* contains last valid entry */
                                              /* in current control */
```

```
        case EN_SETFOCUS:          /* entering the edit control */
                ctrlchanged = FALSE;
                currentctrl = hCtrl;
            lstrcpy(lasttext,ctrl2s(hCtrl));  /* assumes what is in there*/
            break;                             /* is a valid number */ case EN_CHANGE:            /* contents of edit control changed*/ if (hCtrl != currentctrl) { /* if not in focus, force numeric*/
                    if (!isvalidnumber(ctrl2s(hCtrl))) {
                        s2ctrl(hCtrl, NANSTRING);
                        s2ini(currentengineid, wParam, NANSTRING);
                        M_M4SERROR(
 "Attempt to place a non-number in a numeric field--entry cleared.");
                        }
                    else if (!inrange(decodedouble(ctrl2s(hCtrl)),
                                            pid2low(wParam),
                                            pid2high(wParam))) {
                        s2ctrl(hCtrl, NANSTRING);
                        s2ini(currentengineid, wParam, NANSTRING);
                        M_M4SERROR(rangeerror(wParam));
                        }
                    }
            else if (!isnumericprefix(ctrl2s(hCtrl))) {/*in focus&invalid*/
                    long lastpt = SendMessage(hCtrl, EM_GETSEL, 0, 0);
/*next line assumes single character insertion caused last text change*/
/*(otherwise the location of point will be unintuitive--no great harm)*/
                    lastpt = MAKELONG(max(LOWORD(lastpt)-1,0),
                                            max(HIWORD(lastpt)-1,0));
                    s2ctrl(hCtrl,lasttext); /* restore previously validated text*/
                    SendMessage(hCtrl, EM_SETSEL, 0, lastpt); /* and position */
                    M_M4SERROR("Numeric input required.");
                    }
            else { /* valid new input: remember that control changed*/
                    ctrlchanged = TRUE;
                    lstrcpy(lasttext,ctrl2s(hCtrl)); /* store validated input*/
                    } break;

case EN_KILLFOCUS:         /* exiting the edit control */ if (ctrlchanged) {
                    if (!isvalidnumber(ctrl2s(hCtrl))) {
                        s2ctrl(hCtrl, "");
                        M_M4SERROR("Incomplete numeric entry cleared.");
```

```
                }
                else if (!inrange(decodedouble(ctrl2s(hCtrl)),
                                    pid2low(wParam),
                                    pid2high(wParam))) {
                    s2ctrl(hCtrl, NANSTRING);
                    M_M4SERROR(rangeerror(wParam));
                }
                ctrl2ini(currentengineid, wParam, hCtrl);/* save the change*/
            }                                            /* in the INI file*/ currentctrl = NULL;
            break;

default:
            break;

} break;

case IDC_LOADFORM: /* Use in lieu of WM_INITDIALOG--there's no dlgproc*/
        for (eid=MINENGINEID; eid <= MAXENGINEID; eid++)
            setbuttontext(hDlg, eid);
        wParam = IDC_ENGINE0 + currentengineid;
        /* no break -- emulates clicking current engine's button */
    case IDC_ENGINE0:
    case IDC_ENGINE1: case IDC_ENGINE2: case IDC_ENGINE3:
    case IDC_ENGINE4: case IDC_ENGINE5: case IDC_ENGINE6:
    case IDC_ENGINE7: case IDC_ENGINE8: case IDC_ENGINE9:
        /* next line assumes that above ids are sequential */
        currentengineid = wParam - IDC_ENGINE0;
        M_ASSERT(currentengineid >= MINENGINEID);
        M_ASSERT(currentengineid <= MAXENGINEID);
        int2ini(DEFENGINEID, IDC_CURRENTENGINEID, currentengineid);
        ini2dlg(hDlg, currentengineid);  /* load form from INI file */
        updateform(hDlg, currentengineid);
        SetWindowText(hDlg, title(currentengineid));
        constraininputs(hDlg, currentengineid, windowlocked);
/* allow for quickly reviewing each configuration in turn via the space bar:*/
        setfocusnextboilerbutton(hDlg, currentengineid);

break;

case IDC_START:

M_ASSERT(!m4e[currentengineid].running);
```

137

```
            m4e[currentengineid].blr = *e_undefined_boiler();
            ini2engine(currentengineid);
            m4e[currentengineid].starttime = timeinhours();
            m4e[currentengineid].lasteventtime =
             m4e[currentengineid].blr.t = m4stimeinhours(currentengineid);
            m4e[currentengineid].eventid = 0;
            if ( NANFLT == m4e[currentengineid].fwflow ) {
            M_M4SERROR("Feedwater flow rate must be specified.");
               SetFocus(GetDlgItem(hDlg, IDC_FWFLOW));
            }
            else if ( m4e[currentengineid].nh3enabled &&
                      NANFLT == m4e[currentengineid].blr.nh3 ) {
            M_M4SERROR("Ammonia must either be specified or disabled.");
               SetFocus(GetDlgItem(hDlg, IDC_NH3));
            }
            else if (E_INITOK != e_init( &m4e[currentengineid].blr ) ) {
            M_M4SERROR(initerr[m4e[currentengineid].blr.initstatus].msg);
            SetFocus(GetDlgItem(hDlg, /* position to error related field */
                       initerr[m4e[currentengineid].blr.initstatus].field));
            }
            else {
               m4e[currentengineid].running = TRUE;
               constraininputs(hDlg, currentengineid, windowlocked);
               SetFocus(GetDlgItem(hDlg,IDC_STOP));
               updatessppoints(currentengineid);
               m4e[currentengineid].scierr = ERROR_NONE;
         m4e[currentengineid].currentevent = nullevent;
               engine2ini(currentengineid);
               logaction(currentengineid, IDC_START);
               SetWindowText(hDlg, title(currentengineid));
               setbuttontext(hDlg, currentengineid);
               clearmarque();
               M_M4SINFO("");
               numberrunning++;
            }
            break;

case IDC_STOP:

M_ASSERT(m4e[currentengineid].running);
         if (IDOK== MessageBox(hDlg, oktostopmessage(currentengineid),
                                    "MACC4SSP Confirmation",
                              MB_OKCANCEL|MB_ICONQUESTION)) {
               m4e[currentengineid].running = FALSE;
               constraininputs(hDlg, currentengineid, windowlocked);
               SetFocus(GetDlgItem(hDlg,IDC_START));
```

```
            int2ini(currentengineid,IDC_RUNNING, m4e[currentengineid].running);
                logaction(currentengineid, IDC_STOP);
                updateform(hDlg, currentengineid);
                SetWindowText(hDlg, title(currentengineid));
                setbuttontext(hDlg, currentengineid);
                numberrunning--;
            }
            break;
        }
        break;

case WM_TIMER:

if (numberrunning > 0) {
            for (eid=MINENGINEID; eid<=MAXENGINEID; eid++) {
                if (m4e[eid].running) {
                    SCIError sciiniterr = sciinit(eid);
                    if (ERROR_NONE==sciiniterr && !m4e[eid].badchecksum) {
                    /*link to SmartCard inititialized OK and engine is running and
                    we don't have a bad checksum (==> undefined controller state) */ m4e[eid].blr.t = m4stimeinhours(eid);  /* update current time */ if (m4e[eid].simulatessp && !m4e[eid].localinput)
                            simulateoperator(eid); /* simulate operator updates, etc. */ switch (getssprequest(eid)) {
                                HCURSOR holdcursor;

case NOOPSSPREQUEST:      /* no action requested */
                                    break;

case UNDOSSPREQUEST:
                                    holdcursor = SetCursor(LoadCursor(NULL,IDC_WAIT));
                                    if (E_INITOK != m4e[eid].blr.initstatus ||
                                    m4stimeinhours(eid) > m4e[eid].blr.lastt+UNDOINTERVAL ||
                                        !e_undo(&m4e[eid].blr))
                                        M_M4SERROR("Could not UNDO");
                                    updatessppoints(eid);
                                    engine2ini(eid);
                                    logaction(eid, IDC_UNDO);
                                    SetCursor(holdcursor);
                                    break;

case UPDATESSPREQUEST:
```

```
        holdcursor = SetCursor(LoadCursor(NULL,IDC_WAIT));
        if (E_INITOK == m4e[eid].blr.initstatus)
            if (e_update(&m4e[eid].blr) & E_NOTUPDATED)
                M_M4SERROR("Update failed.");
            else if (m4e[eid].blr.updatestatus != E_UPDATEOK)
                M_M4SERROR("Update warning--check flags.");

updatessppoints(eid);
        engine2ini(eid);
        logaction(eid, IDC_UPDATE);
        SetCursor(holdcursor);

break;

case REINITSSPREQUEST:

holdcursor = SetCursor(LoadCursor(NULL,IDC_WAIT));
        m4e[eid].blr.bd = E_NAN;  /* set bd, no leak to their */
        m4e[eid].blr.l  = E_NAN;  /* MACC4 determined defaults*/
            if (e_init(&m4e[eid].blr)!=E_INITOK)
                M_M4SERROR("REINIT Failed.");
            updatessppoints(eid);
            engine2ini(eid);
            logaction(eid, IDC_REINIT);
            SetCursor(holdcursor);

break;

case NODATASSPREQUEST:
        M_M4SERROR(
        "Could not read required data to service request.");
        /* no break */
    case OUTOFRANGESSPREQUEST: /* numeric parameters out of range*/
    case AMBIGUOUSSSPREQUEST:  /* multiple requests--clear them */
        m4e[eid].actionsuptodate = FALSE;

break;

}
    if (E_INITOK == m4e[eid].blr.initstatus) {
    scisetdouble(eid,IDC_AFEED,e_afeed(&m4e[eid].blr));/*set feed*/
    scisetdouble(eid,IDC_BFEED,e_bfeed(&m4e[eid].blr));/*pumps */
        if (!m4e[eid].localinput) {
            scisetdouble(eid,IDC_BD, m4e[eid].blr.bd);
            scisetdouble(eid,IDC_FWNA,
                naleak2fwna(m4e[eid].blr.l,m4e[eid].fwflow));
```

140

```
                    scisetdouble(eid,IDC_RATIO,
                        e_congruencyratio(&m4e[eid].blr));
                }
            }
            maybeclearactions(eid);  /* clear action flags */
        }
        if (ERROR_NONE == sciiniterr) {
            maybesetflags(eid);    /* service flag setting requests */
            scifini(eid);          /* close link to SSP */
        }
    }  /* end of "if running" */
}      /* end of looping over each engine id */
if (m4e[currentengineid].running) {  /* make form reflect any changes*/
    updateform(hDlg, currentengineid);  /* due to operator inputs/actions */
    SetWindowText(hDlg, title(currentengineid));
}
return(0);

case WM_CLOSE:

if (windowlocked) {  /* cannot close locked window */
    M_M4SERROR("You must enter the password before closing MACC4SSP");
    return(0);
}
else if (numberrunning > 0 &&
    IDOK != MessageBox(hDlg, closewarningmessage(numberrunning),
            "MACC4SSP Warning", MB_OKCANCEL|MB_ICONHAND))
    return(0);   /* short circuit close */
else {  /* log the user's CLOSE action for each running boiler */
    for (eid=MINENGINEID; eid <= MAXENGINEID; eid++)
        if (m4e[eid].running)
            logaction(eid, IDC_CLOSE);
    /* fall through to ordinary Windows WM_CLOSE */
}
break;

case WM_DESTROY:
    KillTimer(hDlg, M4STIMERID);
    PostQuitMessage(0);
    return(0);

default:
    break;
```

141

```c
    }
    return DefWindowProc (hDlg, message, wParam, lParam);
}

/* WinMain: uses a dialog box as the main window as per the HEXCALC example*/
/* program from Petzold's book "Programming Windows" (Microsoft Press)    */ int PASCAL WinMain(HINSTANCE hInstance, HINSTANCE hPrevInstance,
                   LPSTR lpszCmdLine, int nCmdShow)
{
    MSG msg;
    WNDCLASS wndclass;
    HCURSOR holdcursor;
    hmainwin = NULL;

lpszCmdLine = lpszCmdLine; /* to supress compiler warning */ if (hPrevInstance)
    {
      M_M4SFATALERROR("MACC4SSP already running; switch to MACC4SSP instead.");
        return (0);
    }
    else
    {   /* register the class used by our dialog box/main window */
        wndclass.style = CS_HREDRAW | CS_VREDRAW;
        wndclass.lpfnWndProc = (WNDPROC) WndProc;
        wndclass.cbClsExtra = 0;
        wndclass.cbWndExtra = DLGWINDOWEXTRA;
        wndclass.hInstance = hInstance;
      wndclass.hIcon = LoadIcon(hInstance, MAKEINTRESOURCE(MACC4SSP_ICON));
        wndclass.hCursor = LoadCursor(NULL,IDC_ARROW);
        wndclass.hbrBackground = COLOR_WINDOW+1;
        wndclass.lpszMenuName = NULL;
        wndclass.lpszClassName = M4SMODULENAME;

RegisterClass(&wndclass);
    } holdcursor = SetCursor(LoadCursor(NULL,IDC_WAIT));
    hmainwin=CreateDialog(hInstance, MAKEINTRESOURCE(MACC4SSP_DIALOG), 0, NULL);
    SetCursor(holdcursor);
```

```
    if (hmainwin == NULL) {
      M_M4SFATALERROR("MACC4SSP fatal error: cannot create main window.");
      return(0);
    }
    else if (!SetTimer(hmainwin, M4STIMERID, DEFTIMERINTERVAL, NULL)) {
      M_M4SFATALERROR("MACC4SSP fatal error: cannot create Windows timer");
      return(0);
    }
    else {

ShowWindow(hmainwin, nCmdShow);
      SendMessage(hmainwin, WM_COMMAND, IDC_LOADFORM, 0); /* loads dlg box */
/* cannot do this in WM_CREATE because Windows creates dialog box controls*/
/* AFTER it sends WM_CREATE; plays the role WM_INITDIALOG usually would */
/* if we were using an ordinary DlgProc (we are using a WndProc instead)*/ while (GetMessage(&msg, NULL, 0, 0))
        if (!IsDialogMessage(hmainwin, &msg))
        {
          TranslateMessage(&msg);
          DispatchMessage(&msg);
        } return (msg.wParam);

}
}
```

We claim:

1. An automatic control system for controlling at least two interdependent chemicals in the fluid of a continuously stirred tank reactor system having an effluent flow, said control system comprising input means for receipt of fluid parameters and control means responsive to said input means, said control means using non-proportional control for automatically minimizing the time that said at least two interdependent chemicals in the fluid spend outside of a target region, and away from a setpoint, of said at least two interdependent chemicals in the fluid without controlling said effluent flow.

2. The control system of claim 1 wherein said continuously stirred tank reactor system is an industrial boiler having a boiler fluid and said effluent flow is a blowdown flow.

3. The control system of claim 2 wherein one of said fluid parameters comprises the pH of the boiler fluid and wherein said input means input means comprises means for determining the pH value of the fluid.

4. The control system of claim 3 wherein said means for determining the pH value of the fluid provides an on-line measurement of the pH value of the fluid.

5. The control system of claim 3 wherein said control means comprises a first feedstream and a second feedstream for feeding first and second fluid treatment materials, respectively, to the boiler fluid at respectively determined feed rates for achieving and maintaining said target region, said first material comprising a mixture of sodium and phosphate having a first predetermined sodium-to-phosphate ratio and said second material comprising a mixture of sodium and phosphate having a second predetermined sodium-to-phosphate ratio.

6. The control system of claim 5 wherein a second of said fluid parameters comprises the phosphate concentration of the boiler fluid and wherein said input means further comprises means for determining the phosphate concentration of the boiler fluid.

7. The control system of claim 6 wherein said means for determining the phosphate concentration of the boiler fluid provides an on-line measurement of the phosphate concentration of the boiler fluid.

8. The control system of claim 6 wherein said target region comprises a desired predetermined ratio of the sodium concentration in the boiler fluid to the phosphate concentration in the boiler fluid.

9. The control system of claim 8 wherein said target region has an upper ratio control limit, a lower ratio control limit, an upper phosphate control limit and a lower phosphate control limit, said limits forming a closed region, said target region having target region vertices.

10. The control system of claim 9 wherein said control means further comprises an adaptive controller, said adaptive controller comprising a model of the industrial boiler for determining said respectively determined feed rates of said first and second fluid treatment materials.

11. The control system of claim 10 wherein said adaptive controller comprises means for accounting for dead time of the boiler during boiler operation.

12. The control system of claim 10 wherein said adaptive controller further comprises means for updating said model responsive to said input means.

13. The control system of claim 12 wherein said input means comprises a blowdown flowmeter for providing an on-line measurement of the blowdown flow.

14. The control system of claim 12 wherein said adaptive controller further comprises means for calculating the blowdown flow.

15. The control system of claim 14 wherein said adaptive controller further comprises means for calculating the sodium concentration in the boiler fluid.

16. The control system of claim 15 wherein said input means further comprises means for measuring ammonia in the boiler fluid and wherein said means for calculating the sodium concentration in the boiler fluid accounts for the ammonia in the boiler fluid.

17. The control system of claim 16 wherein said adaptive controller further comprises means for determining a feedwater contaminant ingress.

18. The control system of claim 15 wherein said adaptive controller further comprises means for determining a feedwater contaminant ingress.

19. The control system of claim 18 wherein said means for calculating the blowdown flow and said means for calculating a feedwater contaminant ingress are based on a series of phosphate and pH measurements in an industrial boiler system using small sample intervals.

20. The control system of claim 18 wherein said adaptive controller further comprises means for developing a pumpable region that defines a first range of steady state boiler fluid sodium and phosphate concentrations that are attainable from the current boiler fluid sodium and phosphate concentrations using a second range of first feedstream feed rates and second feedstream feed rates, said pumpable region having pumpable region vertices and a pumpable region perimeter.

21. The control system of claim 20 wherein said adaptive controller further comprises means for analyzing said target region, said pumpable region, and said current boiler fluid sodium and phosphate concentrations in a boiler state space.

22. The control system of claim 21 wherein said adaptive controller comprises means for determining that said target region cannot be reached from said boiler state space by any feed program.

23. The control system of claim 22 wherein said means for determining that said target region cannot be reached warns the operator and implements a feed program that will drive said current boiler fluid concentrations towards an area of said pumpable region that is closest to said target region.

24. The control system of claim 21 wherein said means for analyzing determines an optimum feed program, said optimum feed program controlling said respectively determined feed rates of said first and second feedstreams in order to achieve said target region within the boiler fluid in the least amount of time.

25. The control system of claim 24 wherein said optimum feed program comprises first means for bringing said current boiler fluid concentrations within said target region in the least amount of time thereby establishing new boiler fluid concentrations and second means for bringing said new boiler fluid concentrations to a predetermined setpoint within said target region in the least amount of time.

26. The control system of claim 25 wherein said optimum feed program further comprises means for maintaining said respectively determined feed rates corresponding to said setpoint once said setpoint has been achieved.

27. The control system of claim 25 wherein said first means for bringing said current boiler fluid concentrations within said target region in the least amount of time comprises means for analyzing a first set of feed rate trajectories that form lines between the current boiler fluid concentrations and said pumpable region vertices, and a second set of feed rate trajectories that form lines between the current boiler fluid concentrations and said target region vertices, said second set of feed rate trajectories being projected until they intersect said pumpable region perimeter if at all, thereby defining a third set of feed rate trajectories.

28. The control system of claim 27 wherein said means for analyzing selects one feed rate trajectory from said first and said third set of feed rate trajectories that reaches said target region in the least amount of time.

29. The control system of claim 25 wherein said second means for bringing said new boiler fluid concentrations to said setpoint in the least amount of time comprises means for determining the feed rate trajectory that coincides with a line formed between said new boiler fluid concentrations and said setpoint, said feed rate trajectory being projected until it intersects said pumpable region perimeter, if at all.

30. The control system of claim 25 wherein said second means for bringing said new current boiler fluid concentrations to said setpoint in the least amount of tile comprises means for establishing a new target region around said setpoint and having new target region vertices.

31. The control system of claim 30 wherein said second means for bringing said new boiler fluid concentrations to said setpoint in the least amount of time further comprises means for analyzing a fourth set of feed rate trajectories that form lines between the new boiler fluid concentrations and said pumpable region vertices, and a fifth set of feed rate trajectories that form lines between the new boiler fluid concentrations and said new target region vertices, said fifth set of feed rate trajectories being projected until they intersect said pumpable region perimeter if at all, thereby defining an sixth set of feed rate trajectories.

32. The control system of claim 31 wherein means for analyzing selects one feed rate trajectory from said fourth and said sixth set of feed rate trajectories that reaches said new target region in the least amount of time, thereby establishing newer boiler fluid concentrations.

33. The control system of claim 32 wherein said second means further comprises means for repeating the establishment of additional target regions and corresponding feed rate trajectories based on said newer boiler fluid concentrations, said means for repeating operating until said setpoint is achieved.

34. A method for controlling at least two interdependent chemicals in the fluid of a continuously stirred tank reactor system having an effluent flow, said method comprising the steps of:
(a) establishing a mathematical model of said continuously stirred tank reactor system;
(b) monitoring the concentration of one of said at least two interdependent chemicals in the fluid, the pH of the fluid and the temperature at which the pH is measured;
(c) updating the model based on the concentration of said one of said at least two interdependent chemicals in the fluid, the pH of said fluid and the temperature at which the pH is measured;
(d) providing a feedstream of a high-pH fluid treatment material comprising a mixture of said at least two interdependent chemicals and a feedstream of a low-pH fluid treatment material comprising a mixture of said at least two interdependent chemicals for feeding to the fluid at respective feed rates; and
(e) developing an optimum feed rate program for controlling said feedstreams to automatically achieve and maintain a setpoint of said at least two interdependent chemicals in the fluid of the continuously stirred tank reactor system in the least amount of time from the current concentrations of said chemicals in the fluid.

35. The method of claim 34 wherein said step of developing an optimum feed rate program includes generating a pumpable region in a system state space that defines a first range of all steady state fluid concentrations of said at least two interdependent chemicals in the fluid that are attainable from the current concentrations of said at least two interdependent chemicals in the fluid depending on a second range of first feedstream feed rates and second feedstream feed rates, said pumpable region having pumpable region vertices and a pumpable region perimeter that corresponds to said second range of first feedstream feed rates and second feedstream feed rates.

36. The method of claim 35 wherein said step of developing an optimum feed rate program further includes:
(a) defining a new target region about said setpoint and having new target region vertices;
(b) determining the time required to drive the new concentrations of said at least two interdependent chemicals in the fluid along a fourth set of feed rate trajectories formed between the new concentrations of said at least two interdependent chemicals and said pumpable region vertices;
(c) determining the time required to drive the new concentrations of said at least two interdependent chemicals in the fluid along a fifth set of feed rate trajectories formed between the new concentrations of said at least two interdependent chemicals and said new target region vertices, said fifth set of feed rate trajectories being projected until they intersect said pumpable region perimeter if at all, thereby defining a sixth set of feed rate trajectories;
(d) selecting one feed rate trajectory from said fourth and sixth set of feed rate trajectories that requires the least amount of time to reach said new target region and then pumping said first and second feedstreams along said selected feed rate trajectory, thereby establishing newer concentrations of said at least two interdependent chemicals in the fluid;
(e) repeating steps a-d until said setpoint is achieved; and
(f) maintaining the feed rates of said first and said second feedstreams that correspond to said setpoint when said setpoint is achieved.

37. The method of claim 35 wherein said step of developing an optimum feed rate program further includes defining a target region about said setpoint of said at least two interdependent chemicals, said target region having target region vertices.

38. The method of claim 37 wherein said step of developing an optimum feed rate program further includes determining the time required to drive the current concentrations of said at least two interdependent chemicals in the fluid along a first set of feed rate trajectories formed between the current concentrations of said at least two interdependent chemicals and said pumpable region vertices.

39. The method of claim 38 wherein said step of developing an optimum feed rate program further includes determining the time required to drive the current concentrations of said at least two interdependent chemicals in the fluid along a second set of feed rate trajectories formed between the current concentrations of said at least two interdependent chemicals and said target region vertices, said second set of feed rate trajectories being projected until they intersect said pumpable region perimeter if at all, thereby defining a third set of feed rate trajectories.

40. The method of claim 39 wherein said step of developing an optimum feed rate program further includes selecting one feed rate trajectory from said first and third set of feed rate trajectories that requires the least amount of time to reach said target region and then pumping said first and second feedstreams along said selected feed rate trajectory, thereby establishing new concentrations of said at least two interdependent chemicals in the fluid.

41. The method of claim 40 wherein said step of developing an optimum feed rate program further includes determining a second feed rate trajectory that coincides with a line formed between the new concentrations of said at least two interdependent chemicals in the fluid and said setpoint, said second feed rate trajectory being projected until it intersects said pumpable region perimeter, if at all.

42. The method of claim 41 wherein said step of developing an optimum feed rate program further includes maintaining said respective feed rates of said first and second feedstreams that correspond to said setpoint when said setpoint has been achieved.

43. The method of claim 34 wherein said continuously stirred tank reactor system is an industrial boiler having a boiler fluid and said effluent flow is a blowdown flow.

44. The method of claim 43 wherein said one of said at least two interdependent chemicals is phosphate.

45. The method of claim 44 wherein said one of said at least two interdependent chemicals is sodium.

46. The method of claim 45 wherein said method further includes the step of estimating the blowdown flow.

47. The method of claim 46 wherein said method further includes the steps of calculating the phosphate concentration and the sodium concentration in the boiler fluid.

48. The method of claim 47 wherein said method further includes the step of estimating a feedwater contaminant ingress.

49. The method of claim 48 wherein said steps of estimating a blowdown flow and a feedwater contaminant ingress are based on a series of phosphate and pH measurements of the boiler fluid wherein the system uses small sample intervals.

50. The method of claim 47 wherein said step of calculating the sodium concentration includes a step for measuring ammonia in the boiler fluid and accounting for the ammonia in determining the sodium concentration.

51. The method of claim 50 wherein said method further includes the step of estimating a feedwater contaminant ingress.

52. The method of claim 43 wherein said method further includes measuring the blowdown flow to obtain blowdown flow values.

53. The method of claim 52 wherein said one of said at least two interdependent chemicals is phosphate.

54. The method of claim 53 wherein said one of said at least two interdependent chemicals is sodium.

55. The method of claim 54 wherein said method further includes the steps of calculating the phosphate concentration and the sodium concentration in the boiler fluid.

56. The method of claim 55 wherein said method further includes the step of estimating a feedwater contaminant ingress.

57. The method of claim 56 wherein said method further includes calculating a boiler phosphate mass imbalance.

58. The method of claim 54 wherein said method further includes providing on-line measurement of the pH of the boiler fluid and on-line measurement of the phosphate concentration in the boiler fluid to provide pH values and phosphate concentration values.

59. The method of claim 58 wherein said method further includes calculating a feedwater contaminant ingress.

60. The method of claim 34 wherein said method further includes a step that accounts for dead time in the continuously stirred tank reactor system.

61. A system for controlling the sodium-to-phosphate ratio and the phosphate concentration of a boiler fluid in an industrial boiler having a feedwater flow and a blowdown flow, said system comprising input means for receipt of a boiler fluid parameter and a parameter indicative of said phosphate concentration and control means responsive to said input means for automatically achieving and maintaining a predetermined fixed phosphate concentration of the boiler fluid and for automatically achieving and maintaining a predetermined desired sodium-to-phosphate ratio of the boiler fluid without controlling said blowdown flow and independent of the feedwater flow rate without the need to measure any reactant concentration in the feedwater flow.

62. The system of claim 61 wherein said boiler fluid parameter comprises the pH of the boiler fluid, the pH of the boiler fluid being defined by the sodium-to-phosphate ratio and the phosphate concentration and wherein said input means comprises a pH meter for determining the pH value of the boiler fluid and providing the pH value to said control means.

63. The system of claim 62 wherein said input means further comprises a blowdown flowmeter for monitoring the blowdown flow and providing a signal indicative of said blowdown flow, said parameter indicative of said phosphate concentration being calculated from said signal indicative of said blowdown flow.

64. The system of claim 63 wherein said control means comprises a first feedstream and a second feedstream for feeding first and second fluid treatment materials, respectively, to the boiler fluid, said first material comprising a mixture of sodium and phosphate having a first predetermined sodium-to-phosphate ratio and a first predetermined concentration of phosphate, said second material comprising a mixture of sodium and phosphate having a second predetermined sodium-to-phosphate ratio and a second predetermined concentration of phosphate.

65. The system of claim 64 wherein said first predetermined concentration of phosphate and said second predetermined concentration of phosphate are identical.

66. The system of claim 65 wherein said control means includes maintenance means for maintaining said predetermined fixed phosphate concentration in the boiler fluid, said maintenance means being arranged to deliver said first and second fluid treatment materials to the boiler fluid in proportion to the blowdown flow.

67. The system of claim 66 wherein said control means operates upon a pH setpoint, said pH setpoint being defined by the predetermined desired sodium-to-phosphate ratio and the predetermined fixed phosphate concentration, and wherein said control means further comprises comparator means for comparing the pH value of the boiler fluid with the pH setpoint.

68. The system of claim 67 wherein said maintenance means feeds a selected one but not the other of said first and second fluid treatment materials from its associated feedstream into the boiler fluid at one time, said selected one being selected depending upon whether the pH value is greater than or less than the pH setpoint.

69. The system of claim 68 wherein said input means further comprises a phosphate analyzer for determining a boiler phosphate mass imbalance.

70. A system for maintaining a fixed concentration of a fluid treatment material in the boiler water of an industrial boiler having a blowdown flow and a feedwater flow, said system comprising at least one feedstream for delivering said fluid treatment material to the boiler fluid, said at least one feedstream delivering said fluid treatment material in proportion to said blowdown flow but without controlling the blowdown flow, said system operating independent of the feedwater flow rate without the need to measure any reactant concentration in the feedwater flow.

71. A method for controlling the sodium-to-phosphate ratio and the phosphate concentration of a boiler fluid in an industrial boiler having a blowdown flow and a feedwater flow, said method comprising the steps of:

(a) selecting a predetermined fixed phosphate concentration and a predetermined desired sodium-to-phosphate ratio;

(b) monitoring a boiler fluid parameter;

(c) comparing said boiler fluid parameter with a preestablished setpoint;

(d) monitoring a parameter indicative of said phosphate concentration;

(e) providing a supply of a first sodium phosphate fluid treatment material, said first sodium phosphate fluid treatment material having a first predetermined sodium-to-phosphate ratio and a first known phosphate concentration;

(f) providing a supply of a second sodium phosphate fluid treatment material, said second sodium phosphate fluid treatment material having a second predetermined sodium-to-phosphate ratio and a second known phosphate concentration;

(g) automatically feeding said first sodium phosphate fluid treatment material to the boiler fluid when said monitored parameter is less than or equal to said pre-established setpoint and automatically feeding said second sodium phosphate fluid treatment material to the boiler fluid when said monitored parameter is greater than said pre-established setpoint, said first sodium phosphate fluid treatment material and said second sodium phosphate fluid treatment material defining a selected sodium phosphate fluid treatment material whenever one of these is being automatically fed; and (h) said selected fluid treatment material being fed, in proportion to the blowdown flow without controlling the blowdown flow and independent of the feedwater flow rate without the need to measure any reactant concentration in the feedwater flow, to the boiler fluid based on said parameter indicative of said phosphate concentration to automatically achieve and maintain said predetermined fixed phosphate concentration.

72. The method of claim 71 wherein said monitored parameter is the pH of the boiler fluid.

73. The method of claim 72 wherein said first known phosphate concentration is identical to said second known phosphate concentration.

74. A method for maintaining a fixed concentration of a fluid treatment material in the boiler fluid of an industrial boiler having a blowdown flow and a feedwater flow, said method comprising the steps of:

(a) selecting a predetermined fluid treatment material concentration for the boiler fluid;

(b) providing a supply of the predetermined fluid treatment material having a known concentration;

(c) monitoring the blowdown flow;

(d) feeding the fluid treatment material to the boiler fluid in proportion to the blowdown flow to automatically achieve and maintain the predetermined fluid treatment material concentration in the boiler fluid but without controlling the blowdown flow independent of the feedwater flow rate and without the need to measure any reactant concentration in the feedwater flow.

* * * * *